(12) United States Patent
Faust et al.

(10) Patent No.: US 10,350,315 B2
(45) Date of Patent: Jul. 16, 2019

(54) QUINOLINE-3-CARBOXAMIDE COMPOUNDS AND THEIR USE IN DIAGNOSIS

(71) Applicant: Westfaelische Wihelms-Universitaet Muenster, Muenster (DE)

(72) Inventors: Andreas Faust, Billerbeck (DE); Sven Hermann, Muenster (DE); Johannes Roth, Muenster (DE); Michael Schaefers, Havixbeck (DE); Thomas Vogl, Muenster (DE)

(73) Assignee: Westfaelische Wihelms-Universitaet Muenster, Muenster (DE)

( * ) Notice: Subject to any disclaimer, the term of this patent is extended or adjusted under 35 U.S.C. 154(b) by 0 days.

(21) Appl. No.: 15/522,536

(22) PCT Filed: Oct. 29, 2015

(86) PCT No.: PCT/IB2015/058348
§ 371 (c)(1),
(2) Date: Apr. 27, 2017

(87) PCT Pub. No.: WO2016/067238
PCT Pub. Date: May 6, 2016

(65) Prior Publication Data
US 2017/0333577 A1 Nov. 23, 2017

Related U.S. Application Data

(60) Provisional application No. 62/069,952, filed on Oct. 29, 2014.

(51) Int. Cl.
| | | |
|---|---|---|
| C07D 401/14 | (2006.01) |
| A61K 51/04 | (2006.01) |
| A61K 49/00 | (2006.01) |
| C07F 13/00 | (2006.01) |
| G01N 33/58 | (2006.01) |
| G01N 33/60 | (2006.01) |
| G01N 33/68 | (2006.01) |
| G06T 7/00 | (2017.01) |

(52) U.S. Cl.
CPC ...... *A61K 51/0474* (2013.01); *A61K 49/0002* (2013.01); *A61K 49/0032* (2013.01); *A61K 49/0036* (2013.01); *A61K 49/0043* (2013.01); *A61K 51/044* (2013.01); *C07D 401/14* (2013.01); *C07F 13/00* (2013.01); *G01N 33/582* (2013.01); *G01N 33/60* (2013.01); *G01N 33/6893* (2013.01); *G06T 7/0014* (2013.01); *G01N 2333/4727* (2013.01); *G01N 2800/7095* (2013.01); *G06T 2207/10088* (2013.01); *G06T 2207/10104* (2013.01); *G06T 2207/10108* (2013.01); *G06T 2207/10132* (2013.01)

(58) Field of Classification Search
None
See application file for complete search history.

(56) References Cited

FOREIGN PATENT DOCUMENTS

WO WO-2012151556 A2 * 11/2012 ............. A01N 65/00

OTHER PUBLICATIONS

Lewis, R. ed., Hawley's Condensed Chemical Dictionary 15th ed. New york John Wiley 2007, p. 711.*
Bjork, P., et al., (2009) "Identification of Human S100A9 as a Novel Target for Treatment of Autoimmune Disease via Binding to Quinoline-3-Carboxamides," Toxicology Letters, 79:800-812.
Gao, M., et al. (2010) "Synthesis and In Vitro Biological Evaluation of Carbon-11-Labeled Quinoline Derivatives as New Candidate PET Radioligands for Cannabinoid CB2 Receptor Imaging", Bioorganic & Medicinal Chemistry, 18:2099-2106.
Turkman, N., et al. (2010) "Synthesis and Preliminary Evaluation of [18F]-Labeled 2-Oxoquinoline Derivative for PET Imaging of Cannabinoid CB2 Receptor", Nuclear Medicine and Biology, 39:593-600.
Vogl, T., et al. (2014) "Alarmin S100A8/S100A9 as a Biomarker for Molecular Imaging of Local Inflammatory Activity", Nature Communications, 5:1-12.
Faust, A., et al. (2015) "Development and Evaluation of a Non-Peptidic Ligand forthe Molecular Imaging of Inflammatory Process Using S100A9 (MRP14) as a Novel Target", Chemical Communications, 51 :15637-15640.
Jonsson, S., et al. (2004) "Synthesis and Biological Evaluation of New 1,2-Dihydro-4-hydroxy-2-oxo-3-quinolinecarboxamides for Treatment of Autoimmune Disorders: Structure-Activity Relationship", Journal of Medicinal Chemistry, 47:2075-2088.

* cited by examiner

*Primary Examiner* — Heidi Reese
(74) *Attorney, Agent, or Firm* — Kagan Binder, PLLC

(57) ABSTRACT

The present application provides quinoline-3-carboxamide compounds covalently linked to a label for use in the diagnosis of an inflammatory disease at local site. The above mentioned compounds can be used to detect or image accumulation of S100A9 in the body of a subject at sites of inflammation, using in vivo non-invasive molecular imaging techniques for the detection of said compounds. Accordingly, labeled quinoline-3-carboxamide compounds can be applied to evaluate the risk of a subject of developing an inflammatory disease and to follow the progress of the disease.

9 Claims, 22 Drawing Sheets

A
in vivo

WT  S100A9⁻/⁻
CES271-Cy5.5

B control    inflammation

A

B exact mass [$^{99}$TcC$_{40}$H$_{47}$N$_7$O$_9$]$^+$: 868.2492
Δm = 1.357 ppm

A 0-10  10-20  20-30  60-70  80-90 min

B

A

B

QUINOLINE-3-CARBOXAMIDE COMPOUNDS AND THEIR USE IN DIAGNOSIS

CROSS REFERENCE TO RELATED APPLICATION

This application claims priority to International Application No. PCT/IB2015/058348, filed on Oct. 29, 2015, which claims the benefit of U.S. Provisional Patent Application Ser. No. 62/069,952 filed Oct. 29, 2014, entitled QUINOLINE-3-CARBOXAMIDE COMPOUNDS FOR USE IN DIAGNOSIS, the disclosures of which are incorporated herein by reference.

FIELD OF THE INVENTION

The present invention relates to quinoline-3-carboxamide compounds (Q-compounds) covalently linked to a label, and their use in diagnosis. The present invention further relates to a method of diagnosing an inflammatory disease in a subject, comprising (a) administering a quinoline-3-carboxamide covalently linked to a label, (b) detecting the administered compound using in vivo non-invasive molecular imaging techniques, thereby collecting imaging data, and (c) comparing the imaging data received in step (b) to reference imaging data. Provided is also a non-invasive method of detecting or imaging accumulation of S100A9 in the body of a subject to whom a quinoline-3-carboxamide covalently linked to a label has been pre-delivered. The present invention is further directed to the use of a quinoline-3-carboxamide covalently linked to a label for the preparation of a diagnostic composition for diagnosing an inflammatory process. A method for evaluating whether a subject may be at risk of developing an inflammatory disease associated with phagocyte and/or epithelial cell activation and S100A9 accumulation is also envisaged. The present invention also relates to a method of monitoring or evaluating the progression of an inflammatory reaction in a patient. A method of imaging an inflammatory disease associated with phagocyte and/or epithelial cell activation in a subject is further comprised by the present invention. Provided is also an in vitro method of diagnosing an inflammatory disease in a subject to whom a quinoline-3-carboxamide covalently linked to a label has been pre-delivered.

BACKGROUND OF THE INVENTION

Inflammatory reactions, autoimmune and autoinflammatory diseases, and cardiovascular diseases such as atherosclerosis or myocardial ischemia characteristically feature local inflammatory processes which initially aim for repair of injured tissue, but in effect cause damage to tissue during chronic diseases. Cells of the innate immune system, especially pro-inflammatory activated phagocytes such as macrophages or neutrophils, but also epithelial cells, play a pivotal role in many inflammatory disorders. Activated phagocytes significantly contribute to the progression of inflammatory diseases such as atherosclerosis, myocardial infarction, acute coronary syndromes, autoimmune diseases as rheumatoid arthritis, inflammatory bowel diseases, infectious diseases, tumors and others.

In various diseases at sites of inflammation, e.g. in inflammatory atherosclerotic plaques, activated phagocytes and epithelial cells express and locally secrete high levels of the S100 protein complex S100A8/S100A9, also known as calprotectin, which acts as so called alarmin or Danger Associated Molecular Pattern (DAMP) molecule with potent pro-inflammatory capacities (Vogl et al. 2007, Loser et al. 2010, Chan et al. 2012). These bind to both the extracellular matrix and receptors such as Toll-like receptor 4 (TLR4) or receptor for advanced glycation endproducts (RAGE) on the immune cell surface, thereby amplifying inflammatory reactions. A correlation between serum levels of S100A8/S100A9 and disease activity has been observed in many inflammatory diseases (Foell and Roth, 2004). Moreover, overexpressed S100A8/S100A9 reflects the disease activity in many inflammatory cardiovascular disorders. For example, in acute coronary syndrome (ACS) or atherosclerotic plaques in instable angina pectoris, S100A9 belongs to the highest of upregulated genes. Here S100A8 and S100A9 constitute 40% of neutrophilic and up to 5% of monocytic cytosolic protein (Hessian et al. 1993). $S100A9^{-/-}$ mice are protected from endotoxin-induced lethal shock and *E. Coli*-induced abdominal sepsis, indicating strong pro-inflammatory functions of these proteins. The expression of S100A9 and S100A8 is generally regarded as closely related, and the loss of S100A9 results in a functional knockout of S100A8 protein in S100A9 deficient mice.

Since both S100A8 and S100A9 proteins are actively secreted by activated cells at site of inflammation and participate in pro-inflammatory cascades, they are considered as attractive targets for non-invasive molecular imaging, especially since despite tremendous efforts in blood testing and conventional clinical imaging the monitoring of the local activity of these inflammatory processes remains unsatisfactory. Conventional imaging techniques are useful to show structural damage due to chronic inflammation, but still lack the necessary cellular and molecular specificity and sensitivity to detect inflammatory disease activity itself. In contrast, molecular imaging techniques such as single photon emission tomography (SPECT) and positron emission tomography (PET), relying on the intravenous application of radiopharmaceuticals, are capable of offering unique molecular sensitivity for preclinical and clinical studies. Thus, these technologies allow for the in vivo diagnosis of inflammatory diseases on the basis of anatomical, morphological and physiological changes and to assess efficiency of therapy.

Previously, the use of antibody-based optical probes such as Cy5.5®-labelled antibodies targeting S100A9 (anti-S100A9-Cy5.5) has been reported in disease scores in vivo and allowed for excellent correlations of signal intensity and successful imaging of inflammatory activity in various mouse models of inflammation, e.g. allergic and toxic contact dermatitis, collagen induced arthritis, and *Leishmania major* infection (Vogl et al. 2014). Using fluorescence reflectance imaging (FRI), Cy5.5®-labelled antibodies could be effectively applied for non-invasive imaging and the detection of S100A9-expression at the local site of inflammation. However, translation of this imaging strategy into patients is a challenge due to known limitations of antibody imaging.

Moreover, a novel class of non-peptidic compounds (quinoline-3-carboxamide compounds, which are also denoted as Q-compounds) having strong binding affinity against S100A9 has been identified for the treatment of autoimmune diseases (Bjork et al. 2009). Applying photoaffinity labelling, FITC-labelled quinoline-3-carboxamide compounds have been used as probes for "fishing" cells expressing S100A9 as target on their surface. The binding affinity of FITC-labelled quinoline-3-carboxamide compounds to human peripheral blood mononuclear cells (PBMC) could be demonstrated, and S100A9 as most prominent binding protein has been identified in the cell membrane applying matrix assisted laser desorption/ionization time-of-flight (MALDI-TOF). Using recombinant S100A9 and S100A8, a strong binding affinity of quinoline-3-carboxamide compounds to homodimeric S100A9 could be observed, whereas only weak binding was observed for the S100A8/S100A9 complex, and close to baseline levels for S100A8 homodimer. Thus, Björk et al. 2009 conclude that binding of quinoline-3-carboxamide compounds is more or less exclusively restricted to homodimeric S100A9 and thus, quinoline-3-carboxamide compounds have high potency in inhibiting the interaction between human and mouse S100A9 and TLR4/MD2. Accordingly, S100A9 may be a potential pharmacological target for quinoline-3-carboxamide compounds, and the use of quinoline-3-carboxamide compounds in the treatment of autoimmune/inflammatory diseases has been suggested.

Although labelled S100A9 antibodies for use in a method of diagnosing inflammatory diseases have been described in the art in mice, there exists a need for alternative compounds having high molecular specificity to S100A9 for a simple in vivo diagnosis of inflammatory diseases associated with an increased release of S100A9 in humans for use in in preclinical and clinical trials. Such compounds should be suitable to analyze molecular levels of already early stage inflammation at local site, and should be applicable for other non-invasive imaging modalities as for example single photon emission tomography (SPECT), positron emission tomography (PET), optical imaging, ultrasound and photoacoustic imaging, which offer unique molecular sensitivity. Diagnosing inflammatory diseases at already early states would be a great advantage for the prognosis of patients and appropriate treatments could be started in time. Additionally, such compounds should be suitable to evaluate the risk of a subject to develop an inflammatory disease and to monitor the progression of an inflammatory disease under different therapeutic conditions. Accordingly, there is a need in the art for compounds having high molecular sensitivity to S100A9 for the prognosis of inflammatory diseases and for monitoring the effectiveness of inflammatory disease treatment.

In sum, there is a need in the state of the art to provide new means and methods that help to diagnose inflammatory disease associated with an increased accumulation of S100A9 at local site of inflammation at molecular level. The technical problem underlying the present application is thus to comply with this need. The technical problem is solved by providing the embodiments reflected in the claims, described in the description and illustrated in the examples and figures that follow.

SUMMARY OF THE INVENTION

The present invention is, at least partly, based on the surprising finding that non-peptidic quinoline-3-carboxamide compounds covalently linked to a label are well suited for diagnostic use. In particular, the present invention demonstrates that non-peptidic quinoline-3-carboxide compounds covalently linked to a label are applicable for use in the diagnosis of an inflammatory disease associated with accumulation of S100A9 at local site of inflammation, using non-invasive molecular imaging techniques for detecting said compounds in vivo. In this regard, the inventors of the present application surprisingly found that quinoline-3-carboxamide compounds covalently linked to a label specifically bind to S100A9 and can thus be used for diagnosing inflammatory diseases with high molecular sensitivity.

This was unforeseeable, as quinoline-3-carboxamide compounds have exclusively been described in the art for therapeutic use in the treatment of autoimmune diseases, but a diagnostic approach of compounds in which substituted or unsubstituted quinoline-3-carboxiamide is covalently linked to a label has never been reported so far.

To analyze inflammatory processes at local site of inflammation, the present inventors synthesized novel non-peptidic S100A9-specific ligands having strong binding affinity against S100A9, which are well suited for use in various molecular imaging methods. In this regard, known quinoline-3-carboxide compounds were covalently linked to fluorescent, radioactive, ultrasound and/or photoacoustic labels, including inter alia Cy5.5®, $^{18}$F, $^{123}$I, $^{125}$I, $^{99}$Tc, phthalo- and naphthalocyanines. As firstly provided by the present invention, such non-peptidic quinoline-3-carboxamide compounds are well suited for use in in vivo non-invasive molecular imaging techniques such as single photon emission tomography (SPECT), position emission tomography (PET), optical imaging, magnetic resonance imaging (MRI), ultrasound or photoacoustic imaging.

In particular, an optical (fluorescent) probe based on the non-peptidic S100A9 ligand quinoline-3-carboxamide (CES271-Cy5.5) could be successfully synthesised and demonstrates high binding affinity to S100A9. Imaging experiments in mouse models showed significant accumulation of CES271-Cy5.5 at the sites of inflammatory active diseases, e.g. in mouse models of dermatitis, myocardial infarction, acute lung injury (ALI) and atherosclerosis, which was not observed in S100A9 deficient mice. In this regard, biodistribution studies of CES271-Cy5.5 in healthy Balb/c mice demonstrate a good tissue availability of the compound and an elimination mainly driven by renal excretion. Accordingly, a first optical imaging probe Cy5.5-CES271 based on non-peptidic quinoline-3-carboxamide for specific imaging of extracellularly released S100A9 protein could be developed, indicating local phagocyte activity. The specificity was confirmed by a modified S100-ELISA and the binding potency was determined as sufficient for both murine and human S100A9 for in vivo optical imaging techniques. Moreover, the Cy7-CES271 variant has been compared with the well characterized anti S100A9 antibody based tracer aS100A9-Cy5.5 by parallel injection into inflamed and control ears of a dermatitis mouse model, revealing a higly significant correlation between the Cy7-CES271 and aS100A9-Cy5.5 signal.

Moreover, the dye of Cy5.5/Cy7-CES271 could be replaced with a bisimidazoyl-unit for labelling with $^{99m}$Tc, providing the non-peptidic SPECT-tracer [$^{99m}$Tc]FEB054 as a radioactive alternative. Also here, a very good blood serum stability and a suitable blood half-life for in vivo experiments in inflammatory disease models like ear inflammation and rheumatoid arthritis could be demonstrated. Another subject of the present invention is the provision of SPECT-probe $^{99m}$Tc-FEB105 and PET-probe (1-[4-(5-ethyl-4-hydroxy-N,1-dimethyl-2-oxo-1,2-dihydroquinoline-3-carboxamido)phenyl]-4-fluoro-1-oxobutane-2-sulfonic acid) based on the non-peptidic S100A9 ligand quinoline-3-carboxamide, which can be used according the present invention as alternative imaging probes.

The analysis of early mechanisms of inflammation in response to initial danger signal using the non-peptidic quinoline-3-carboxamide compounds as described herein is however a novel approach for diagnosing and monitoring inflammatory diseases at local site. Accordingly, the phagocyte-specific S100A9-protein, one subunit of the heterodimeric S100A8/S100A9 complex is a promising target for molecular imaging of inflammatory activity in vivo. Moreover, the present disclosure prompts that the quinoline-3-carboxamide compound as provided herein can be used in prognosis of the risk of a subject to develop an inflammatory disease associated with an overexpression and accumulation of S100A9, and to monitor the progression of inflammation and the effectiveness of inflammation treatment at molecular level.

Additionally, the inventors of the present application developed a specific ELISA to analyze S100A9 binding to TLR4. When adding the novel S100A9 specific ligands of the present invention, TLR4-binding of S100A9 protein was markedly blocked, resulting in a decrease of signal given by the TLR4-S100A9 ELISA, and confirming specific binding of CES271-Cy5.5 to S100A9. Thus, non-peptidic quinoline-3-carboxamide compounds as disclosed herein may further be appropriate to specifically block the binding properties of S100A9 to TLR4.

FITC-labeled quinoline-3-carboxamide compounds have previously been described in the art as probes to identify S100A9 and for assaying the biological effect of these compounds. However, the present invention suggest for the very first time the use of novel S100A9-specific ligands based on substituted or unsubstituted quinoline-3-carboxamide covalently linked to a fluorescent, radioactive, ultrasound and/or photoacoustic labels in diagnosis of inflammatory diseases, applying in vivo non-invasive molecular imaging techniques. This was unforeseeable, since the state of the art exclusively relates to the use of Cy5.5®-labelled antibodies in non-invasive imaging methods and merely mentions the therapeutic use of FITC-labelled quinoline-3-carboxamide compounds in the treatment of autoimmune disorders while keeping the immune effector stage intact.

The present invention is at least partly based on the surprising fact that quinoline-3-carboxamide compounds covalently linked to a label are well suited for use in diagnosis of inflammatory diseases associated with an increased phagocyte and/or epithelial cell activity and an increased accumulation of S100A9. In this regard, these compounds could be successfully used for in vivo non-invasive molecular imaging in models of dermatitis, myocardial infarction and atherosclerosis. Accordingly, in one aspect, the present invention relates to a compound in which a substituted or unsubstituted quinoline-3-carboxamide is covalently linked to a label, wherein the compound is not

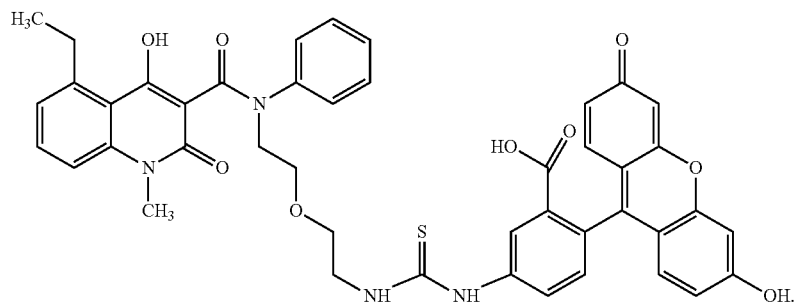 [SMILES: CCc1cccc2c1c(O)c(C(=O)N(CCOCCNC(=S)Nc1ccc(-c3c4ccc(=O)cc-4oc4cc(O)ccc34)c(C(=O)O)c1)c1ccccc1)c(=O)n2C]

In some embodiments the compound of the present invention has formula (I)

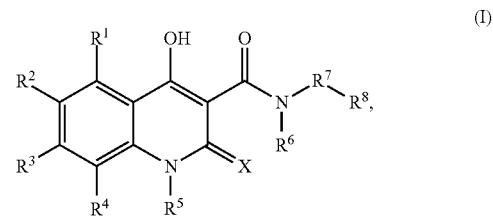

wherein $R^1$, $R^2$, $R^3$ and $R^4$ are each independently selected from the group consisting of H, optionally substituted linear or branched C1-C6 alkyl, optionally substituted linear or branched C2-C6-alkenyl, optionally substituted linear or branched C2-C6-alkynyl, optionally substituted aryl, optionally substituted heteroaryl, optionally substituted cycloalkyl, halogen, hydroxyl, amino, cyano, and optionally substituted linear or branched C1-C6 alkoxy; or each of $R^1$ and $R^2$, $R^2$ and $R^3$, and/or $R^3$ and $R^4$, together with the atoms to which they are attached, form an optionally substituted 4- to 8-membered carbocyclic or heterocyclic ring; $R^5$ is selected from the group consisting of H, optionally substituted linear or branched C1-C6 alkyl, optionally substituted linear or branched C2-C6-alkenyl, optionally substituted linear or branched C2-C6-alkynyl, optionally substituted aryl, optionally substituted heteroaryl, and optionally substituted cycloalkyl; $R^6$ is H or an optionally substituted group selected from the group consisting of aryl, heteroaryl, alkyl, cycloalkyl, alkenyl and alkynyl; $R^7$ is an optional linker; X is O or S; and $R^8$ is a label; or a salt, isomer, or tautomer thereof.

In some embodiments the label $R^8$ is a metal binding group with a metal coordinated by said binding group. The metal binding group for the metal can be any group which is able to coordinate to the metal like $^{99m}Tc$, $^{186}Re$, $^{188}Re$, $^{111}In$, $^{67}Ga$, $^{68}Ga$, $^{64}Cu$ and/or $^{89}Zr$ and at the same time bound covalently to $R^7$ or to amide nitrogen of the $CONR^6$ group of formula I. In some embodiments the binding group is a monodentate, bidentate, tridentate or polydentate binding group able to coordinate the metal at one, two, three or several coordination sites of said metal. In some embodiments the binding group is negatively or positively charged.

In some embodiments the binding group coordinates the metal together with an additional metal binding group, wherein the additional binding group is preferably not bound to the compound according to formula I. In some embodiments the additional binding group is a monodentate, bidentate, tridentate or polydentate binding group able to coordinate the metal at one, two, three or several coordination sites of said metal, preferably a bidentate binding group, more preferably bathophenanthrolinedisulfonic acid disodium salt hydrate. In some embodiments the binding group is negatively or positively charged, preferably negatively charged. In some embodiments the binding group and the metal or the binding group, the additional binding group and the metal are a SPECT label.

In some embodiments $R^3$ and $R^4$ are each H. In some embodiments $R^1$ and $R^2$ are each independently selected from the group consisting of H, Cl, —$CH_3$, —$CH_2CH_3$, —$CH_2CH_2CH_3$, and —$CH(CH_3)_2$. In some embodiments $R^1$ is —$CH_2CH_3$ and $R^2$ is H. In some embodiments $R^1$ and $R^2$, together with the atoms to which they are attached, form an optionally substituted 5- or 6-membered aryl or heteroaryl ring. In some embodiments the optionally substituted 5 or 6 membered aryl or heteroaryl ring is selected from the group consisting of

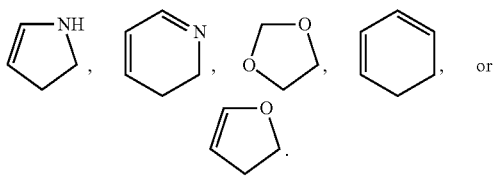

In some embodiments, $R^5$ is an optionally substituted C1-C6 alkyl. In some embodiments $R^5$ is an optionally substituted C1-C3 alkyl. In some embodiments $R^5$ is —$CH_3$, —$CH_2CH_3$, —$CH_2CH_2CH_3$, or —$CH(CH_3)_2$. In some embodiments $R^5$ is —$CH_3$. In some embodiments X is O. In some embodiments $R^6$ is an optionally substituted group selected from the group consisting of aryl, heteroaryl, and alkyl. In some embodiments $R^6$ is —$CH_3$ or phenyl. In some embodiments $R^3$ and $R^4$ are each H; $R^1$ and $R^2$ are each independently selected from the group consisting of H, Cl, —$CH_3$, —$CH_2CH_3$, —$CH_2CH_2CH_3$, and —$CH(CH_3)_2$; $R^5$ is —$CH_3$; X is O; and $R^6$ is —$CH_3$ or phenyl, preferably phenyl. In some embodiments $R^1$ is —$CH_2CH_3$ or —$CH(CH_3)_2$, and wherein $R^2$ is H. In some embodiments $R^1$ is —$CH_2CH_3$.

In some embodiments of the present invention $R^1$ and $R^2$, together with the atoms to which they are attached, form a 5 or 6 membered aryl or heteroaryl ring; wherein $R^3$ and $R^4$ are each H; $R^5$ is —$CH_3$; X is O; and $R^6$ is —$CH_3$ or phenyl, preferably phenyl. In some embodiments the 5 or 6 membered aryl or heteroaryl ring is selected from the group consisting of

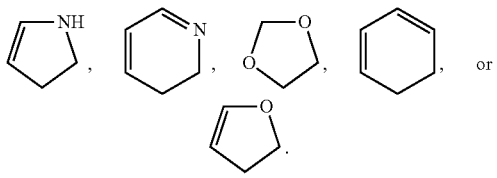

In some embodiments of the present invention, $R^7$ is a linker comprising

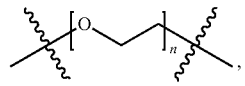

wherein n is an integer from 0 to 20. In some embodiments n is from 1 to 10. In some embodiments n is from 1 to 5. In a preferred embodiment n is 3.

In some embodiments the label of the compound according to the present invention is a positron emission tomography (PET) label. In some embodiments the label is a single photon emission tomography (SPECT) label. In some embodiments the label is an optical imaging label. In some embodiments the label is a magnetic resonance imaging (MRI) label. In some embodiments the label is an ultrasound label. In some embodiments the label is a photoacoustic label. In some embodiments the label comprises a group selected from the group consisting of $^{18}F$, $^{68}Ga$, $^{123}I$, $^{124}I$, $^{125}I$, $^{99m}Tc$, $^{111}In$, $^{67}Ga$, $^{64}Cu$, $^{11}C$, $^{89}Zr$, fluorescent dyes and absorbers.

In some embodiments the label comprises a PET label selected from the group consisting of

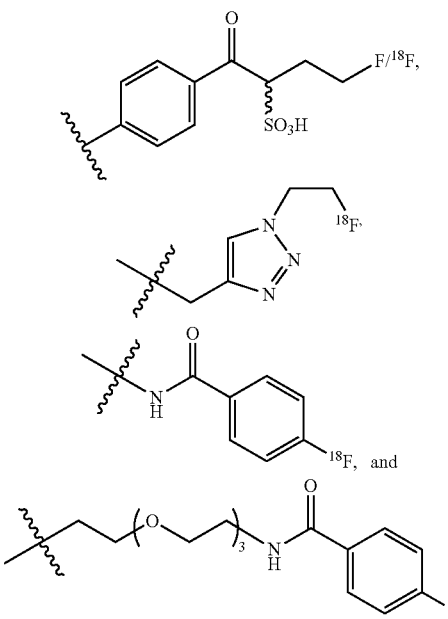

In some embodiments the PET label contains an acidic group, preferably a sulphonic acid group. In some embodiments the PET label is

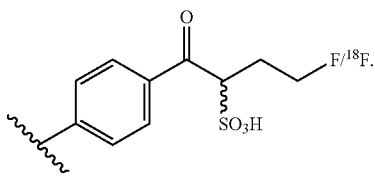

In some embodiment the compound according to the present invention has formula (III)

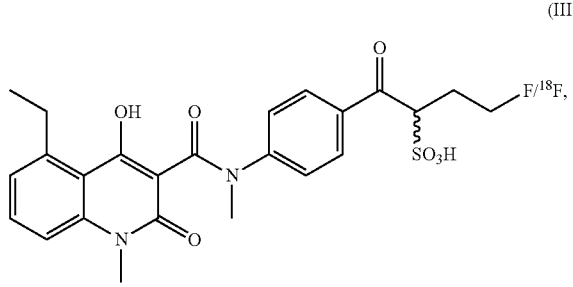

(III)

or is a salt, hydrate, isomer or tautomer thereof.

In some embodiments the label comprises a SPECT label selected from the group consisting of

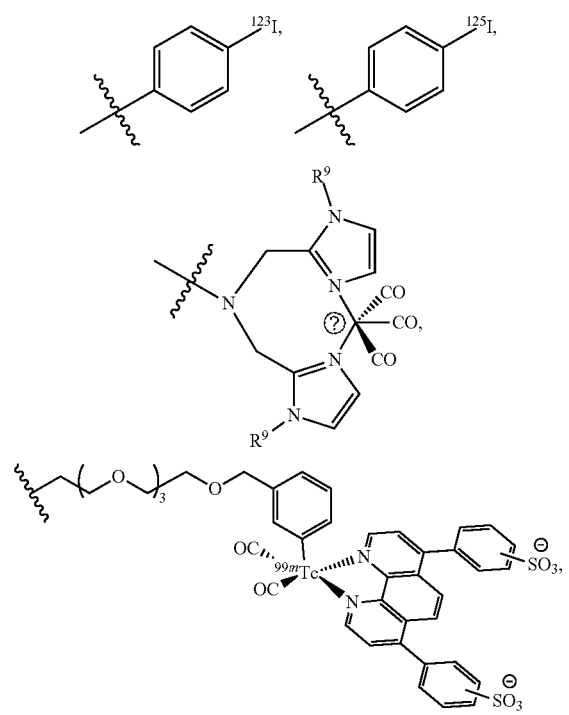

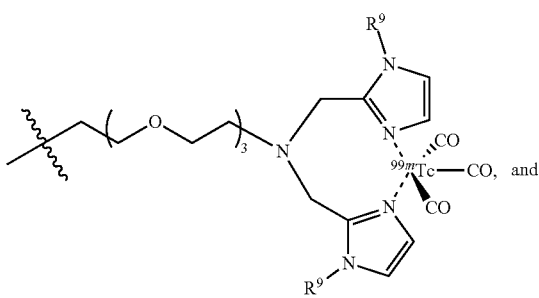

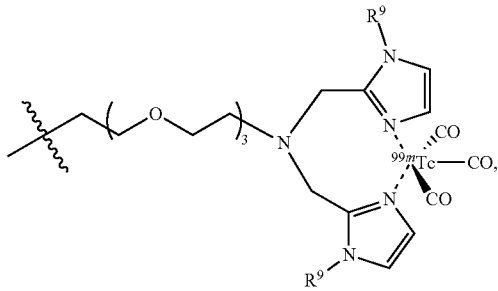

wherein each $R^9$ is independently selected from the group consisting of —$CH_3$,

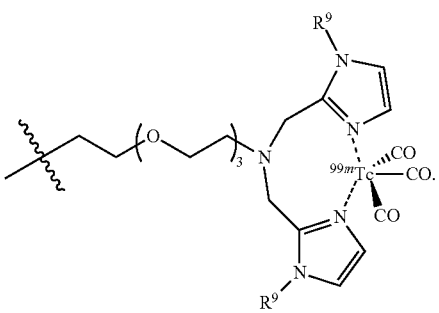

preferably wherein each $R^9$ is the same. In some embodiments $R^9$ is methyl. In some embodiments the SPECT label is negatively or positively charged, preferably negatively charged. In some embodiments the SPECT label is In some embodiment the SPECT label is

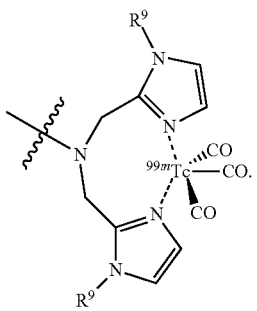

In some embodiments the SPECT label is

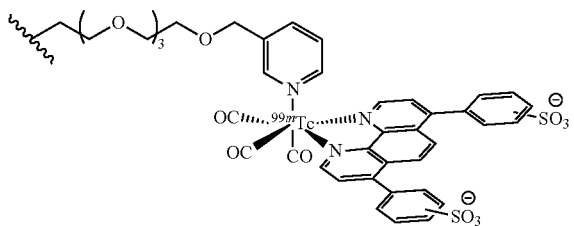

In some embodiments the SPECT label is

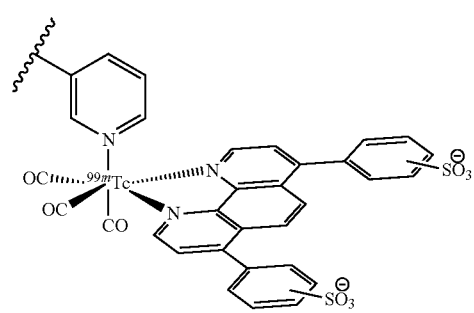

In some embodiment the SPECT label contains an acidic group, preferably a sulphonic acid group, more preferably a sulphonic acid salt. In some embodiments the SPECT label is a metal binding group with a metal coordinated by said binding group. The metal binding group for the metal can be any group which is able to coordinate to the metal like $^{99m}$Tc, $^{186}$Re, $^{188}$Re, $^{111}$In, $^{67}$Ga, $^{68}$Ga, $^{64}$Cu and/or $^{89}$Zr and at the same time bound covalently to $R^7$ or to amide nitrogen of the $CONR^6$ group of formula (I). In some embodiments the binding group is a monodentate, bidentate, tridentate or polydentate binding group able to coordinate the metal at one, two, three or several coordination sites of said metal. In some embodiments the binding group is negatively or positively charged. In some embodiment the compound according to the present invention has formula (IV):

(IV)

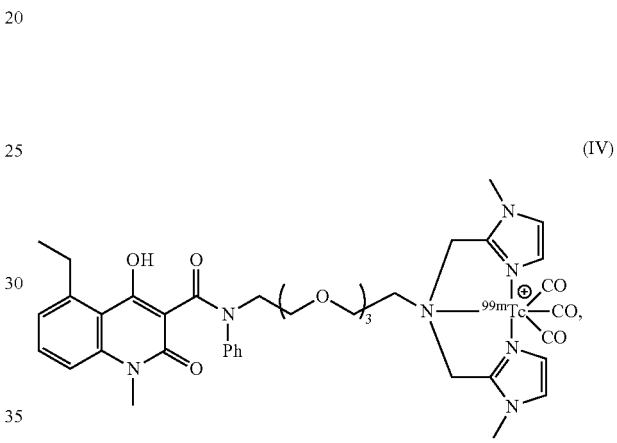

or is a salt, hydrate, isomer or tautomer thereof. In some embodiment the compound according to the present invention has formula (V)

(V)

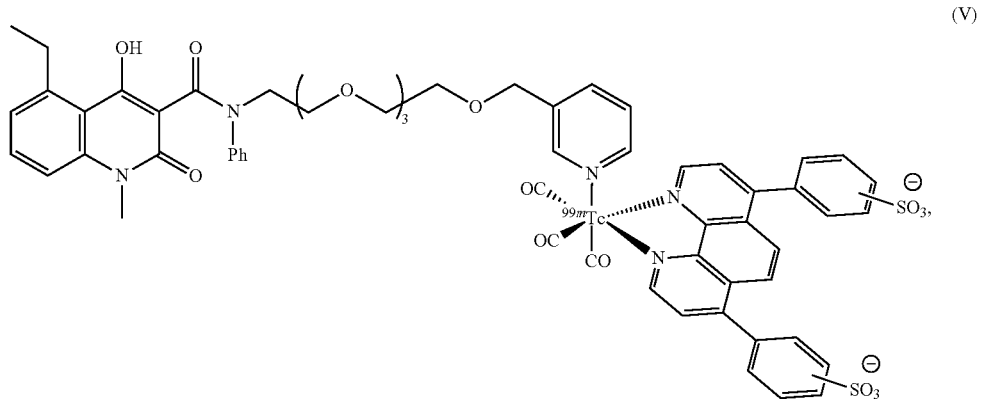

or is a salt, hydrate, isomer or tautomer thereof.

In some embodiments of the present invention, the label comprises a photoacoustic imaging label. In some embodiments the photoacoustic label is a phthalocyanine. In some embodiments the photoacoustic label is a naphthalocyanine. In some embodiments the photoacoustic label is a polymethine dye. In some embodiments the label comprises a photoacoustic imaging label which is an absorber selected from the group consisting of:

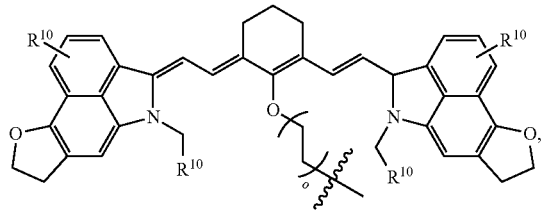

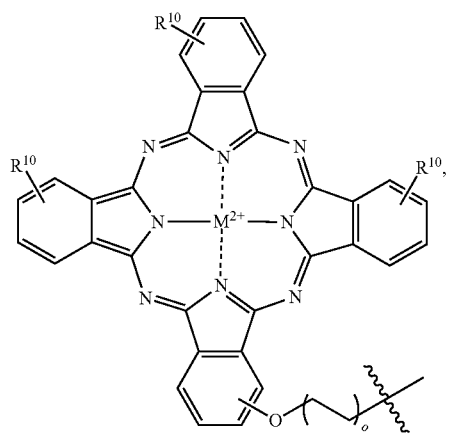

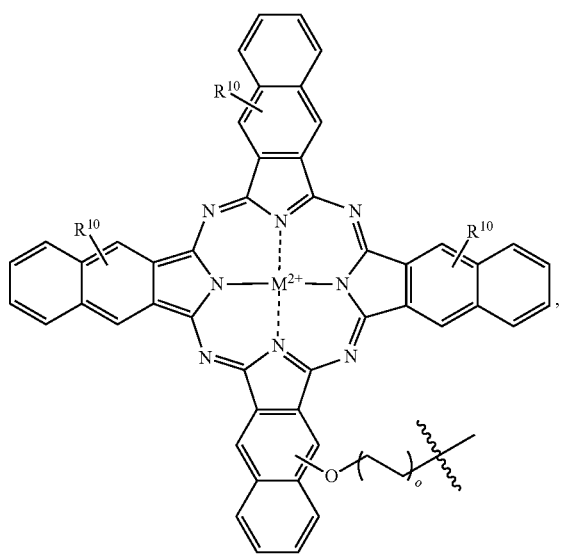

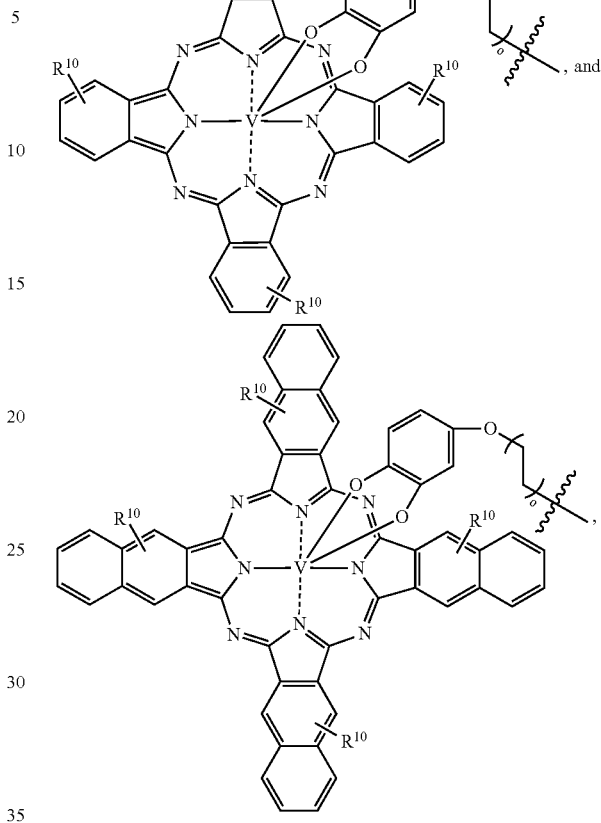

wherein each $R^{10}$ is independently selected from the group consisting of sulphonic acids, ammonium salts, and thioethers, preferably wherein each $R^{10}$ is the same; wherein o is an integer from 0 to 20, preferably from 1- to 10, more preferably from 1- to 5, most preferably o is 3; and wherein $M^{2+}$ is Fe, Cu, Ni, or V(=O).

In some embodiments the label comprises an optical imaging label. In some embodiments the optical imaging label is a dye. In some embodiments the dye is fluorescein isothiocyanate (FITC). In some embodiments the dye is 1,1'-dioctadecyl-3,3,3',3'-tetramethyl indotricarbocyanine iodide (DiR). In some embodiments the dye is a coumarin dye. In some embodiments the dye is a rhodamine dye. In some embodiments the dye is a carbopyronin dye. In some embodiments the dye is an oxazine dye. In some embodiments the dye is a fluorescein dye. In some embodiments the dye is a cyanine dye. In some embodiments the dye is_a boron-dipyrromethene (BODIPY) dye. In some embodiments the dye is a squaraine dye. In some embodiments the dye is a squaraine rotaxane dye. In some embodiments the dye is an Alexa Fluor® dye. In some embodiments the dye is a DyLight® Fluor dye. In some embodiments the dye is an ATTO® dye. In some embodiments the dye is a BODIPY® dye. In some embodiments the dye is a SETA® dye. In some embodiments the dye is a SeTau® dye. In some embodiments the dye is Alexa Fluor® 488.

In some embodiments the optical imaging label is a fluorophore. In some embodiments the fluorophore is a polymethine dye. In some embodiments the polymethine dye is a cyanine dye. In some embodiments the cyanine dye is cyanine 3. In some embodiments the cyanine dye is cyanine 3.5. In some embodiments the cyanine dye is cyanine 5. In some embodiments the cyanine dye is cyanine 5.5. In some embodiments the cyanine dye is cyanine 7.

In some embodiment the compound according to the present invention has formula (II)
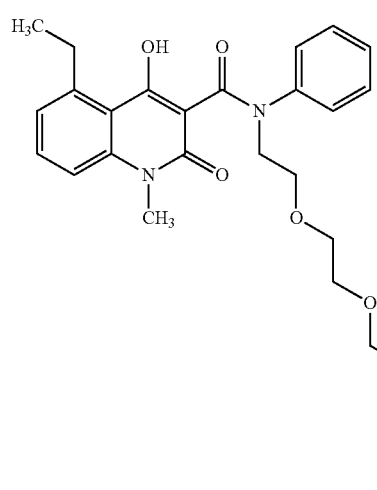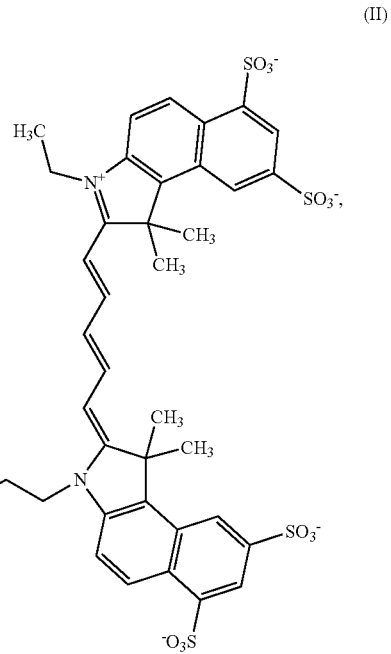
(II)
or is a salt, isomer, or tautomer thereof.
In some embodiment the compound according to the present invention has formula (VIII)
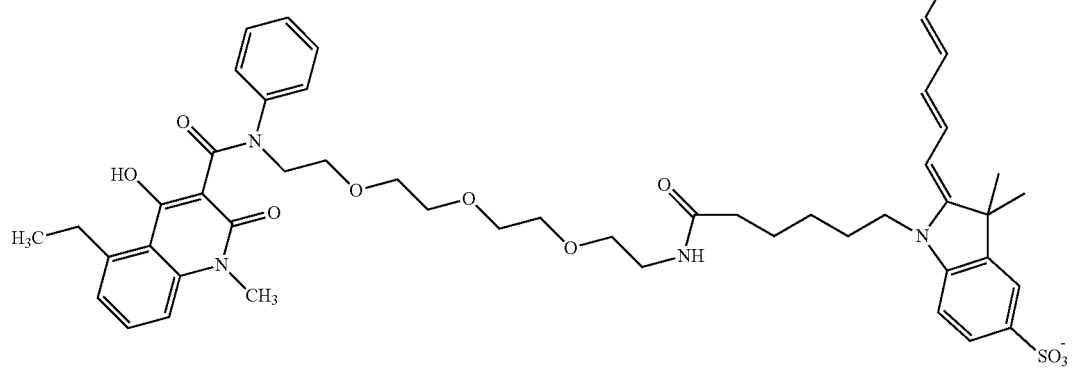
(VIII)
or is a salt, isomer, or tautomer thereof.

According to another aspect of the present invention, the compounds disclosed herein or the compound

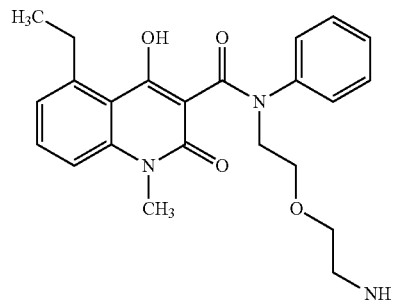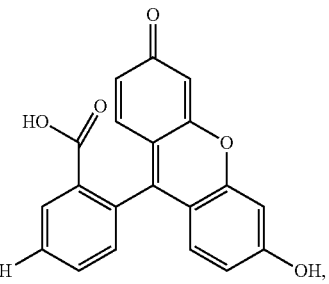

are diagnostic compounds.

In another aspect, the present invention further relates to a diagnostic composition comprising any of the compounds as described herein above and a pharmaceutically or diagnostically acceptable excipient.

According to a further aspect, the present invention provides the use of any of the compounds as disclosed herein above in a method of diagnosis. In some embodiments the diagnosis is a diagnosis of an inflammatory disease in a subject. Preferably the method of diagnosing an inflammatory disease is a non-invasive molecular imaging method. In a preferred embodiment the non-invasive molecular imaging method is an in vivo molecular imaging method. In some embodiments the non-invasive molecular imaging method is an in vitro molecular imaging method. In some embodiments the non-invasive molecular imaging method is single photon emission tomography (SPECT). In some embodiments the non-invasive molecular imaging method is positron emission tomography (PET). In some embodiments the non-invasive molecular imaging method is optical imaging. In some embodiments the non-invasive molecular imaging method is magnetic resonance imaging (MRI). In some embodiments the non-invasive molecular imaging method is ultrasound. In some embodiments the non-invasive molecular imaging method is photoacoustic imaging.

As provided herein, the inflammatory disease is associated with phagocyte and/or epithelial cell activation in said subject. In some embodiments the inflammatory disease is further associated with an overexpression and accumulation of S100A9 in said subject. In some embodiments the inflammatory disease is dermatitis, preferably irritant dermatitis (ICD). In some embodiments the inflammatory disease is atherosclerosis. In some embodiments the inflammatory disease is psoriasis. In some embodiments the inflammatory disease is an autoimmune disease. In some embodiments the inflammatory disease is arthritis. In some embodiments the inflammatory disease is allergies. In some embodiments the inflammatory disease is cardiovascular processes. In some embodiments the inflammatory disease is local and systemic infections. In some embodiments the inflammatory disease is a neuroinflammatory disease. In some embodiments the inflammatory disease is acute lung injury (ALI). In some embodiments the inflammatory disease is a tumor.

The method of diagnosis as described herein is typically a method of an early stage diagnosis. In a preferred embodiment, the inflammatory disease diagnosed by the method of the present invention is at local site.

The subject of the present invention is typically a mammal. In some embodiments the mammal is a mouse. In some embodiments the mammal is a rat. In some embodiments the mammal is a guinea pig. In some embodiments the mammal is a rabbit. In some embodiments the mammal is a cat. In some embodiments the mammal is a dog. In some embodiments the mammal is a horse. Preferably the mammal is human.

In some embodiments the method of the present invention comprises administering any of the compounds as disclosed herein above to the subject. The administration of the compound may be carried out variously. In some embodiments the administration is carried out intravenously. In some embodiments the administration is carried out subcutaneously. In some embodiments the administration is carried out intralesionally. In some embodiments the administration is carried out by application to mucous membranes. In some embodiments the administration is carried out orally. In some embodiments the administration is carried out parenterally. In some embodiments the administration is carried out intramuscularly. In some embodiments the administration is carried out intraperitoneally. In some embodiments the administration is carried out by intranasal instillation. In some embodiments the administration is carried out by implantation. In some embodiments the administration is carried out by intracavitary instillation. In some embodiments the administration is carried out by intravesical instillation. In some embodiments the administration is carried out intraocularly. In some embodiments the administration is carried out intraarterially. In some embodiments the administration is carried out transdermally. Preferably, the administration is carried out intravenously, subcutaneously, intralesionally, or by application to mucous membranes.

According to another aspect, the present invention relates to a method of diagnosing an inflammatory disease in a subject, comprising:
a) administering to said subject any of the compounds as disclosed herein above,
b) detecting the administered compound using an in vivo non-invasive molecular imaging technique, thereby collecting imaging data,
c) comparing the imaging data received in step b) to reference imaging data.

In a further aspect the present invention provides a non-invasive method of detecting or imaging accumulation of S100A9 in the body of a subject to whom any of the compounds as disclosed herein above has been pre-delivered, comprising:
a) detecting the administered compound using an in vivo non-invasive molecular imaging technique, thereby collecting imaging data, b) comparing the imaging data received in step a) to reference imaging data.

According to the methods of the present invention described herein above, an increased signal in the imaging data from the subject as compared to reference imaging data indicates the presence of an inflammatory disease in said subject, wherein no difference in the signal in the imaging data from the subject as compared to reference imaging data indicates no presence of an inflammatory disease in said subject.

According to another aspect, the present invention relates to the use of any of the compounds as disclosed herein above for the preparation of a diagnostic composition for diagnosing an inflammatory disease associated with phagocyte and/or epithelial cell activation in a subject.

In a further aspect, the present invention also provides a method for evaluating whether a subject may be at risk of developing an inflammatory disease associated with phagocyte and/or epithelial cell activation, the method comprising:
a) administering to said subject any of the compounds as disclosed herein above,
b) detecting the administered compound using an in vivo non-invasive molecular imaging technique, thereby collecting imaging data,
c) comparing the imaging data received in step b) to reference imaging data.

In this regard, a significantly increased signal in the imaging data from the subject as compared to reference imaging data indicates that said subject is at higher risk of developing an inflammatory disease associated with phagocyte and/or epithelial cell activation. On the other hand, a signal in the imaging data at a normal level as compared to reference imaging data indicates that said subject is at lower risk of developing an inflammatory disease associated with phagocyte and/or epithelial cell activation.

According to another aspect, also provided herein is a method of monitoring or evaluating the progression of an inflammatory disease associated with phagocyte and/or epithelial cell activation in a patient, the method comprising:
a) administering to said subject any of the compounds as disclosed herein above,
b) detecting the administered compound using an in vivo non-invasive molecular imaging technique, thereby collecting imaging data,
c) comparing the imaging data received in step b) to reference imaging data obtained from said patient at an earlier date, wherein the result of the comparison of c) provides an evaluation of the progression of the inflammatory disease associated with phagocyte and/or endothelial cell activation in said patient.

In this regard, a significantly increased signal in the imaging data from the patient as compared to reference imaging data obtained from said patient at an earlier date indicates a progression of the inflammatory disease associated with phagocyte and/or endothelial cell activation in said patient. On the other hand, no change in the signal of the imaging data from the patient or a decreased signal in the imaging data from the patient as compared to reference imaging data obtained from said patient at an earlier date indicates no progression or a regression of the inflammatory disease associated with phagocyte and/or endothelial cell activation in said patient.

In a further aspect, the present invention provides a method of imaging an inflammatory disease in a subject, comprising:
a) administering to said subject any of the compounds as disclosed herein above,
b) detecting the administered compound using an in vivo non-invasive molecular imaging method, thereby collecting imaging data.

Also provided herein is an in vitro method of diagnosing an inflammatory disease in a subject to whom any of the compounds as disclosed herein above has been pre-delivered, comprising:
a) analyzing a sample taken from said subject,
b) detecting said pre-delivered compound using a non-invasive molecular imaging method, thereby collecting imaging data,
c) comparing the imaging data received in step b) to reference imaging data.

According to the in vitro method described herein, an increased signal in the imaging data from the subject as compared to reference imaging data indicates the presence of an inflammatory disease in said subject, wherein no difference in the imaging signal in the imaging data from the subject as compared to reference imaging data indicates no presence of an inflammatory disease in said subject.

DETAILED DESCRIPTION OF THE INVENTION

Unless otherwise stated, the following terms used in this document, including the description and claims, have the definitions given below.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Those skilled in the art will recognize, or be able to ascertain, using not more than routine experimentation, many equivalents to the specific embodiments of the invention described herein. Such equivalents are intended to be encompassed by the present invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The present invention discloses for the first time that novel synthesized non-peptidic quinoline-3-carboxamide compounds covalently linked to a label are well suited for diagnostic use. In this regard, the present invention provides new compounds for diagnosing inflammatory diseases associated with an accumulation of S100A9 at an early stage of inflammation, using non-invasive molecular imaging techniques for the detection of said compounds. The inventors of the present application found that quinoline-3-carboxamide compounds covalently linked to various labels can specifically bind to S100A9 and thus can be used for diagnosing inflammatory diseases at local sites in vivo. This disclosure was unexpected as quinoline-3-carboxamide compounds were reported as to be useful in therapeutic approaches for the treatment of autoimmune diseases, but the applicability in diagnosis of inflammatory diseases has never been reported so far.

The present invention provides for the diagnostic use of non-peptidic quinoline-3-carboxamide compounds covalently linked to a label for the detection of local inflammatory activities and to predict disease outcome. In this regard it could be demonstrated, that S100A9 serves as a sensitive local marker for the detection of even sub-clinical disease activity in inflammatory and immunological processes, and to predict the development of disease activity. Additionally, the findings of the present invention provide novel imaging approaches and allow for monitoring of clinically relevant inflammatory and cardiovascular disorders on a molecular level.

Quinoline-3-carboxamide Compounds (Q-Compounds) and Synthesis of S100A9 Specific Ligands A known quinoline-3-carboxamide compound is the synthetic non-peptidic immunomodulator "Laquinimod" (1), which was previously selected for clinical studies in man, and has demonstrated efficacy in animal models of several autoimmune diseases, including multiple sclerosis. Phase II studies show favourable tolerability and safety based on clinical and laboratory indicators. The drug was granted a fast track review by the FDA in 2009 (Preiningerova 2009).

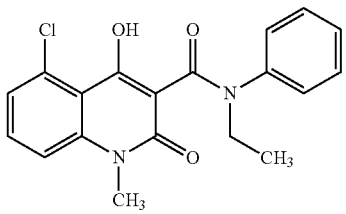

Multivariate analytical tools were used to derive the structure-activity-relationship (SAR) for the affinity of a series of quinoline-3-carboamide analogues towards S100A9, with the assumption that similar analogues bind to the same binding site in a similar binding mode (Björk 2009). Embodiments of possible quinoline-3-carboxamide compound variations are shown in FIG. 1. With regard to the first SAR studies employing a small number of ligands, the most potent ligands are based on the quinoline-3-carboxamide compounds with an ethyl group as variable "R" in the 5-position (instead of the chloride, as in Laquinimod (1) (Björk 2009). Other derivatives are possible, but ethyl is a preferred embodiment. Several different amino/aniline derivatives could be used for the amide-formation to yield a wide variety of quinoline-3-carboxamide derivatives (see synthesis section below for further detail), and significant variation at the carboxamide portion (blue section in FIG. 1) is allowable when preparing quinoline-3-carboxamide compounds as described herein. Reasonable structural variations on the quinoline motif (the red section in FIG. 1, non-limiting examples of possible variations may include those shown in the boxed portion) may also be tolerated and/or may be used to improve binding affinity to the S100A9 target.

The variable R' in FIG. 1 represents a label, linked to the quinoline-3-carboxamide compound derivative via an optional linker. When used herein, the term "label" can also be replaced by the term "tracer". In some embodiments, introduction of polyethylene glycol linker moieties and/or sulfonic acids at the label site (variable R' in FIG. 1) may be used to provide convenient pharmacokinetic behaviour of the tracer and/or the molecular imaging probe. As will be known to the person of skill in the art, any suitable known label modality, for use with any suitable imaging or detection method as described herein, are possible. By way of non-limiting example, any suitable label moiety known to the person of skill in the art for use in optical imaging (non-limiting examples may include a fluorescent label such as Cy5.5®, Cy3®, Cy3.5®, Cy5®, or Cy7®, PET (non-limiting examples may include a label having a $^{18}F$ group), SPECT (non-limiting examples may include a label having a $^{123}$I, $^{124}$I, $^{125}$I, $^{99m}$Tc, $^{186}$Re or $^{188}$Re group), or photoacoustic imaging (non-limiting examples may include an absorber such as polymethine dyes (non-limiting examples include cyanine dyes), phthalocyanines, or naphthalocyanines) may be used. Chelators may be used, including different albumin-tags and sulfonic acids bearing site chains to give optimized pharmacokinetic behaviour. Some non-limiting embodiments of possible components of R' are shown in FIG. 2. In an embodiment, suitable labels for optical imaging may include dyes such as, for example, fluorescein isothiocyanate (FITC), 1,1'-dioctadecyl-3,3,3',3'-tetramethyl indotricarbocyanine iodide (DiR), a coumarin dye, a rhodamine dye, a carbopyronin dye, an oxazine dye, a fluorescein dye, a cyanine dye, a boron-dipyrromethene (BODIPY) dye, a squaraine dye, and a squaraine rotaxane dye. Coumarin dyes, rhodamine dyes, carbopyronin dyes and oxazine dyes are, for example, commercially available under the trade name ATTO® from ATTO-TEC GmbH. Furthermore, coumarin dyes, rhodamin dyes, fluorescein dyes and cyanine dyes are, for example, commercially available under the trade name Alexa Fluor® from Molecular Probes, Inc. Coumarin dyes, rhodamin dyes, fluorescein dyes and cyanine dyes are, for example, also commercially available under the trade name DyLight® Fluor from Dyomics in collaboration with Thermo Fisher Scientific, Inc. Boron-dipyrromethene dyes are, for example commercially available under the tradename BODIPY® from Life Technologies. Squaraine dyes are, for example, commercially available under the trade name SETA® from SETA Bio-Medicals. Squaraine rotaxane dyes are, for example, commercially available under the trade name SeTau® from SETA BioMedicals. In another embodiment suitable labels for MRI may include a perfluorinated $^{19}$F label and Gd(DOTA), wherein DOTA denotes 1,4,7,10-tetraazacyclododecane-1,4,7,10-tetraacetic acetic acid and any conjugated base thereof. In a further embodiment suitable labels for ultrasound imaging may include gas filled microbubbles which are stabilized by a shell, wherein the shell may, for example, be comprised of proteins, lipids or polymers.

An exemplary synthetic route for preparing a non-limiting embodiment of a quinoline-3-carboxamide compound covalently linked to a label as provided herein is described below. It will be understood that this illustrative embodiment is provided to show a possible synthetic route for preparing a non-limiting embodiment of the present invention. It should also be understood that other synthetic routes are possible for preparing the quinoline-3-carboxamide derivatives provided herein, as will be known to the person of skill in the art. In this non-limiting embodiment, a possible synthetic route for preparing a quinoline-3-carboxamide compound having an ethyl group at the 5-position is provided. Initial SAR studies based on a small number of ligands indicated that the most potent ligands are based on the 3-quinoline carboxylic acid 8 having an ethyl group in 5-position. A synthetic route for preparing this derivative is shown in FIG. 3.

Starting from the commercially available 3-nitrophthalic acid anhydride 2, diethyl malonate was condensed and the resulting lactone 3 was treated with hydrochloric acid to give 2-acetyl-6-nitrobenzoic acid 4 (Lüthi et al. 2001). The anthranilic acid 5 was synthesized according to patent document EP2316818A1 (Jansson et al. 2011) in a two-step hydrogenation procedure and treated with phosgene to give the corresponding isatoic anhydride 6. This was N-alkylated with iodomethane to give 7, and condensed with diethyl malonate. Acidic cleavage yielded the 3-quinolinecarboxylic acid 8 intermediate (Jonsson et al. 2004).

Quinoline carboxylic acids such as intermediate 8 can then be coupled to suitable tracers to form quinoline-3-carboxamides which are covalently linked to a label as provided herein. As an illustrative non-limiting example, a possible synthetic route for preparing a quinoline-3-carboxamide compound which is linked to Cy5.5®, suitable for imaging of S100A9 by fluorescence reflectance imaging (FRI) and fluorescence mediated tomography (FMT), is described.

In this embodiment, the cyanine dye Cy5.5® label was joined to intermediate 8 through a PEG (polyethylene glycol) linker in order to avoid interactions between the Cy5.5® label and the protein. In an embodiment, it is preferred that the quinoline-3-carboxamide compound be able to interact with S100A9 free of interference by the label (in this embodiment, Cy5.5®), and so a PEG linker was used to allow a spacing between the quinoline-3-carboxamide compound and the label. While a PEG linker was used in this example, the person of skill in the art will recognize that other suitable linkers known in the art may also be used. The synthesis of this quinoline-3-carboxamide compound for optical imaging of S100A9 is outlined in FIG. 4.

As shown in FIG. 4, commercially available PEG$_4$-alcohol was dimesylated, and on one end the mesylate was substituted by an azide using sodium azide in dimethylformamide. The other mesylate moiety was exchanged by a bromide, which was then substituted by aniline, yielding the desired secondary amine 9 having an azide on the other end of the PEG chain. The key intermediate 8 was then coupled to the secondary aniline 9 by formation of an amide bond, forming intermediate 10. The azide of 10 was subsequently reduced with palladium on charcoal (hydrogen-atmosphere) to give the free amine as precursor for coupling with the cyanine dye. An activated NHS-ester derivative of Cy5.5® was added, and coupled with the free amine to produce the Cy5.5-CES271 product suitable for optical imaging of S100A9.

As a further illustrative non-limiting example, a possible synthetic route for preparing a quinoline-3-carboxamide compound which is linked to

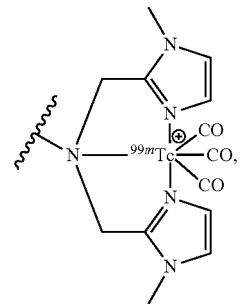

suitable for imaging of S100A9 by single photon emission tomography (SPECT), is described.

In this embodiment, the SPECT label was joined to intermediate 5-ethyl-4-hydroxy-1-methyl-2-oxo-1,2-dihydroquinoline-3-carboxylic acid through a PEG (polyethylene glycol) linker in order to avoid interactions between the SPECT label and the protein. In an embodiment, it is preferred that the quinoline-3-carboxamide compound be able to interact with S100A9 free of interference by the label, and so a PEG linker was used to allow a spacing between the quinoline-3-carboxamide compound and the label. While a PEG linker was used in this example, the person of skill in the art will recognize that other suitable linkers known in the art may also be used. The synthesis of this quinoline-3-carboxamide compound for optical imaging of S100A9 is outlined in FIGS. 9 and 10.

As shown in FIGS. 9 and 10, the 2-{2-[2-(2-azidoethoxy)ethoxy]ethan}1-amine was condensed with 1-Methyl-1H-imidazole-2-carboxaldehyde 2 to yield 2-{2-[2-(2-Azidoethoxy)ethoxy]ethoxy}-N,N-bis[(1-methyl-1H-imidazole-2-yl)methyl]ethylazide 3. The azide 3 was reduced with palladium on charcoal (hydrogen-atmosphere) to give the free amine 4. After subsequent coupling of the amine with phenyl iodate under palladium catalysis, the resulting secondary amine 5 was coupled with key intermediate 5-ethyl-4-hydroxy-1-methyl-2-oxo-1,2-dihydroquinoline-3-carboxylic acid 6 by formation of an amide bond. The resulting coupling product 7 was finally reacted with Technetium salt to yield fac-[$^{99}$mTc(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ ($^{99m}$Tc-FEB054) 9 suitable for SPECT imaging of S100A9. The corresponding Rhenium complex fac-[Re(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ 8 was used as reference compound for the precise identification of the Technetium complex (IV) as shown in FIG. 11.

As a further illustrative non-limiting example, a possible synthetic route for preparing a quinoline-3-carboxamide compound which is linked to

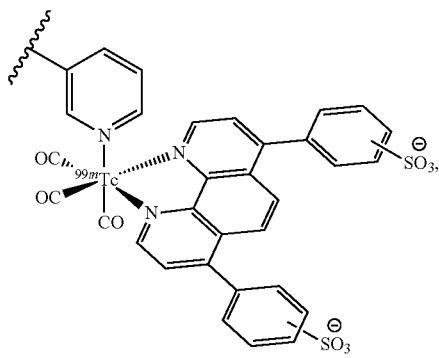

suitable for imaging of S100A9 by single photon emission tomography (SPECT), is described.

In this embodiment, the SPECT label was joined to intermediate 5-ethyl-4-hydroxy-1-methyl-2-oxo-1,2-dihydroquinoline-3-carboxylic acid through a PEG (polyethylene glycol) linker in order to avoid interactions between the SPECT label and the protein. In an embodiment, it is preferred that the quinoline-3-carboxamide compound is able to interact with S100A9 free of interference by the label, and so a PEG linker was used to allow a spacing between the quinoline-3-carboxamide compound and the label. While a PEG linker was used in this example, the person of skill in the art will recognize that other suitable linkers known in the art may also be used. The synthesis of this quinoline-3-carboxamide compound for optical imaging of S100A9 is outlined in FIG. 12.

As show in FIG. 12, the PEG azide 1 was coupled with (bromomethyl)pyridine hydrobromide 2, by forming an ether bond, followed by subsequent reduction of the azide group with triphenyl phosphine to the corresponding amine group 4. The amine was coupled with phenyl iodide under palladium catalysis to yield the corresponding secondary amine 5. The resulting secondary amine was coupled with key intermediate 5-ethyl-4-hydroxy-1-methyl-2-oxo-1,2-dihydroquinoline-3-carboxylic acid 6 by formation of an amide bond. The resulting coupling product 7 was finally reacted with Technetium salt and bathophenanthrolinedisulfonic acid disodium salt hydrate 8 to yield fac-[$^{99m}$Tc(bathophenanthrolinedisulfonic acid)(CO)$_3$(5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide)]$^-$ ($^{99m}$Tc-FEB105) 9 suitable for SPECT imaging of S100A9 (Williams et al 2007).

As a further illustrative non-limiting example, a possible synthetic route for preparing a quinoline-3-carboxamide compound which is linked to

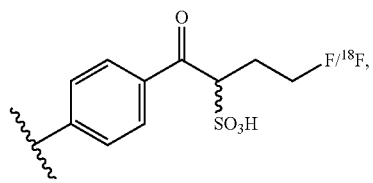

suitable for imaging of S100A9 by positron emission tomography (PET), is described.

In this embodiment, the PET label was joined to intermediate 5-ethyl-4-hydroxy-1-methyl-2-oxo-1,2-dihydroquinoline-3-carboxylic acid. In an embodiment, it is preferred that the quinoline-3-carboxamide compound is able to interact with S100A9 free of interference by the label. The synthesis of this quinoline-3-carboxamide compound for optical imaging of S100A9 is outlined in FIG. 14.

As shown in FIG. 14, the aromatic amine 1 is protected, followed by coupling with 1,3-propane sulfone. The coupling product 3 was deprotected under acidic conditions to yield the secondary amine 4. The resulting secondary amine 4 was coupled with key intermediate 5-ethyl-4-hydroxy-1-methyl-2-oxo-1,2-dihydroquinoline-3-carboxylic acid 5 by formation of an amide bond. Nucleophilic ring opening of the sulfone ring yielded 1-[4-(5-ethyl-4-hydroxy-N,1-dimethyl-2-oxo-1,2-dihydroquinoline-3-carboxamido)phenyl]-4-fluoro-1-oxobutane-2-sulfonic acid 7 (Renard et al 2012).

As used herein the term "label" in general refers to a moiety that allows detection and/or imaging. The label is not particularly limited and may include, for example, labels suitable for use in molecular imaging techniques. By way of example the label may be a label suitable for single photon emission tomography (SPECT), positron emission tomography (PET), optical imaging, ultrasound and/or photoacoustic imaging.

Suitable labels for SPECT may include an $^{123}$I, $^{124}$I, $^{125}$I and/or $^{99m}$Tc. Non-limiting examples may include:

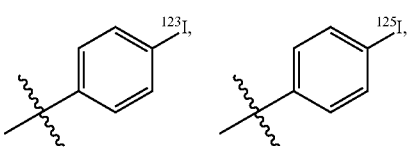

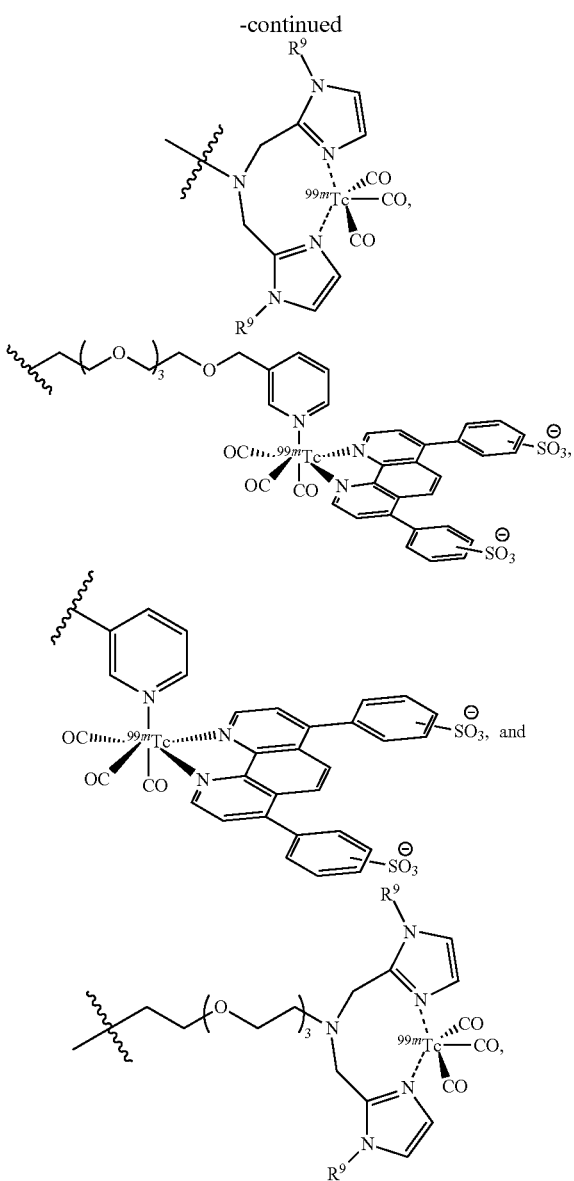

wherein each $R^9$ is independently selected from the group consisting of —$CH_3$,

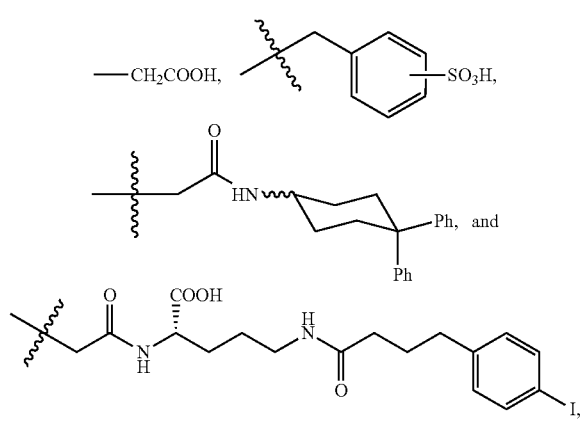

preferably wherein each $R^9$ is the same. In some embodiments $R^9$ is methyl. In some embodiments the SPECT label is negatively or positively charged, preferably negatively charged.

Suitable labels for PET may include an $^{18}F$ or a $^{68}Ga$. Non limiting examples may include:

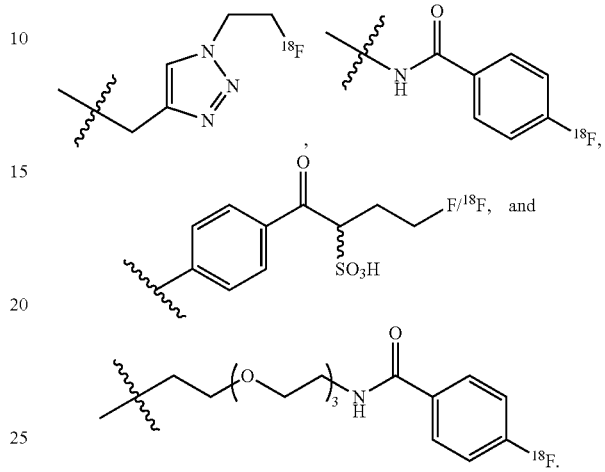

In some embodiments the PET label contains an acidic group, preferably a sulfonic acid group.

Labels for optical imaging may include any suitable fluorophore or dye known in the art. Non-limiting examples may include a cyanine dye such as cyanine 3, cyanine 3.5, cyanine 5, cyanine 5.5 and cyanine 7 or related analogues. For example, the commercially available Cy3®, Cy3.5®, Cy5®, Cy5.5®, Cy7® dyes provided by GE Healthcare may be used. Other fluorophores may include 7-amino-4-methylcoumarin (AMC), fluorescein isothiocyanate (FITC), fluorescein carboxylic acid, 5-carboxytetramethylrhodamine (TAMRA), indocyanine green, a DyLight® Fluor dye, an ATTO® dye, a BODIPY® dye, a SETA® dye, a SeTau® dye, an Alexa Fluor® dye from Invitrogen, an IRdye® dye from Li-COR Bioscience, an SRfluor® dye from Molecular Targeting Technologies, a HyLyte™ Fluor dye from Anaspec, CF™ 633 from Biotium, and an indotricarbocyanine (ITCC) dye. See, for example, B. P. Joshi, T. D. Wang, Exogenous Molecular Probes for Targeted Imaging in Cancer: Focus on Multi-modal Imaging, Cancers 2010, 2(2), 1251-1287.

The term "linear or branched C1-C6 alkyl" as used herein in general refers to a linear-chain, or branched-chain saturated hydrocarbon radical having from one to six carbon atoms, preferably having one to three carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-i-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl. In general, a numerical range such as "C1-C6 alkyl" means that the alkyl group may consist of 1 carbon atom, 2 carbon atoms, 3 carbon atoms, 4 carbon atoms, 5 carbon atoms or 6 carbon atoms.

As used herein the term "linear or branched C2-C6 alkenyl" in general denotes a linear-chain or branched-chain hydrocarbon radical having one or more carbon-carbon double-bonds and having from two to six carbon atoms. The group may be in either the cis or trans configuration about the double bond(s), and should be understood to include both isomers. Non-limiting examples include ethenyl (—CH=CH$_2$), 1-propenyl (—CH$_2$CH=CH$_2$), isopropenyl [—C(CH$_3$)=CH$_2$], butenyl, 1,3-butadienyl and the like. In general, a numerical range such as "C2-C6 alkenyl", means that the alkenyl group may consist of 2 carbon atoms, 3 carbon atoms, 4 carbon atoms, 5 carbon atoms or 6 carbon atoms.

The term "linear or branched C2-C6 alkynyl" as used herein, in general refers to a linear-chain or branched-chain hydrocarbon radical having one or more carbon-carbon triple-bonds and having from two to six carbon atoms. Non-limiting examples include ethynyl, 2-propynyl, 2-butynyl, 1,3-butadiynyl and the like. In general, a numerical range such as "C2-C6 alkynyl", means that the alkynyl group may consist of 2 carbon atoms, 3 carbon atoms, 4 carbon atoms, 5 carbon atoms or 6 carbon atoms.

As used herein, the term "aryl" in general refers to an aromatic hydrocarbon radical of six to twenty ring carbon atoms, and includes fused and non-fused aryl rings. A fused aryl ring radical may contain from two to four fused rings where the ring of attachment is an aryl ring, and the other individual rings may be alicyclic, heterocyclic, aromatic, heteroaromatic or any combination thereof. Further, the term aryl may include fused and non-fused rings containing from six to about twelve ring carbon atoms, as well as those containing from six to about ten ring carbon atoms. A non-limiting example of a single ring aryl group may include phenyl; a fused ring aryl group may include naphthyl, phenanthrenyl, anthracenyl, azulenyl; and a non-fused bi-aryl group includes biphenyl.

The term "heteroaryl" as used herein in general denotes aromatic radicals containing from five to twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl may include heteroaryl radicals having at least one heteroatom. The term heteroaryl may also include fused and non-fused heteroaryls having from five to twelve skeletal ring atoms, as well as those having from five to ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of heteroaryl group includes pyridyl, 2,3-dihydrobenzo[b][1,4]dioxinyl, 2,3,4,5-tetrahydro-1H-benzo[b]azepinyl, benzimidazolyl, quinolinyl, acridinyl, bipyridinyl, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinoiinyl, indolizinyl, isothiazolyi, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

As used herein, the term "cycloalkyl" in general denotes a saturated hydrocarbon radical ring containing from three to fifteen ring carbon atoms or from three to ten ring carbon atoms, though may include additional, non-ring carbon atoms as substituents (e.g. methylcyclopropyl).

The term "alkoxy" as used herein in general refers to an alkyl ether radical, O-alkyl, including the groups O-aliphatic and O-carbocyclyl, wherein the alkyl, aliphatic and carbocyclyl groups are as defined herein. Non-limiting examples of alkoxy radicals incude methoxy, ethoxy, n-propoxy, iso-propoxy, n-butoxy, iso-butoxy, sec-butoxy, tert-butoxy and the like.

The term "carbocyclic" or "carbocyclyl" as used herein in general refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. The term distinguishes carbocyclic from heterocyclic rings in which the ring backbone contains at least one atom which is different from carbon.

The term "heterocyclic" or "heterocyclyl" as used herein refers collectively to heteroalicyclyl and heteroaryl groups. Designations such as "4- to 8 membered heterocyclic ring" refer to the total number of atoms that are contained in the ring (i.e., a four, five, six, seven or eight membered ring, in which at least one atom is a carbon atom, at least one atom is a heteroatom and the remaining atoms are either carbon atoms or heteroatoms). For heterocycles having two or more heteroatoms, those two or more heteroatoms can be the same or different from one another. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. A non-limiting example of "heterocyclic" includes morpholine, azinyl, azetidinyl, oxetanyl, thietanyl, homopiperidinyl, piperidyl, oxepanyl, thiepanyl, oxazepinyl, diazepinyl, thiazepinyl, 1,2,3,6-tetrahydropyridinyl, 2-pyrrolinyl, 3-pyrrolinyl, pyrrolidinyl, indolinyl, 2H-pyranyl, piperazinyl, 2-oxopiperidiyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, (S,S-dioxothio)piperidinyl, 3-azabicyclo[3.1.0]hexyl, 3-azabicyclo[4.1.0]heptyl, 3H-indolyl and quinolizinyl and the like.

In the present application, where any of the above groups is indicated as "optionally substituted", said group is optionally substituted with one or more groups selected from halogen, hydroxy, C1-C6 alkyl, C3-C8 cycloalkyl, C2-C6 alkenyl, C2-C6 alkynyl, C1-C6 alkoxy, C6-C10 aryl, 5-15 membered heterocyclyl with 1-4 heteroatoms selected from N, O or S, 5-10 membered heteroaryl with 1-4 heteroatoms selected from N, O or S, mono-C1-C6 alkylamino, di-C1-C6 alkylamino, mono-C1-C6 alkylaminoacyl, di-C1-C6 alkylaminoacyl, 5-12 membered heterocyclyl-acyl with 1-3 heteroatoms selected from N, O or S, C1-C6 alkylamido, aminosulfonyl, mono-C1-C6 alkylaminosulfonyl, di-C1-C6 alkylaminosulfonyl, aminosulfinyl, mono-C1-C6 alkylaminosulfinyl, di-C1-C6 alkylaminosulfinyl, and C1-C6 alkylsulfonamido.

The linker $R^7$ is an optional linker. This means that according to one option a linker may not be present and that the quinoline-3-carboxamide may be directly connected to the label via a bond. According to another option, a linker $R^7$, which connects the quinoline-3-carboxamide and the label, may be present. In case that a linker $R^7$ is present, virtually any linker moiety (linker) $R^7$ can be used. The linker may, for example, be a straight or branched hydrocarbon based moiety. The linker can also comprise cyclic moieties. If the linking moiety is a hydrocarbon-based moiety the main chain of the linker may comprise only carbon atoms but can also contain heteroatoms such as oxygen (O), nitrogen (N) or sulfur (S) atoms. The linker may for example include a C1-C20 carbon atom chain or a polyether based chain such as polyethylene glycol based chain with —(O—CH$_2$—CH$_2$)— repeating units. In typical embodiments of hydrocarbon based linkers, the linking moiety may comprise between 1 to about 150, 1 to about 100, 1 to about 75, 1 to about 50, or 1 to about 40, or 1 to about 30, or 1 to about 20, including 2, 3, 4, 5, 6, 7, 8, 9, 10, 11, 12, 13, 14, 15, 16, 17, 18, and 19 main chain atoms.

In one preferred embodiment the linker may comprise:

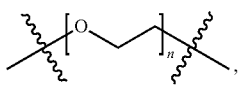

wherein n is an integer from 0 to 20, or from 1 to 10, or from 1 to 5, or wherein n is 3. Thus, for example n may be 0, 1, 2, 3, 4, 5, 6, 7, 8, 9, 10, 11, 12, 13, 14, 15, 16, 17, 18, 19, or 20.

Another subject of the present invention are processes for the preparation of the compounds of the formula I, including their salts and solvates, as outlined below, by which the compounds are obtainable. For example, in one approach for the preparation of a compound of the formula I a compound of the formula (VI), or a compound in which instead of the carboxylic acid group depicted in formula (VI) a reactive carboxylic acid derivative group is present, for example a carboxylic acid chloride group, is reacted with a compound of the formula (VII) to give a compound of the formula (I),

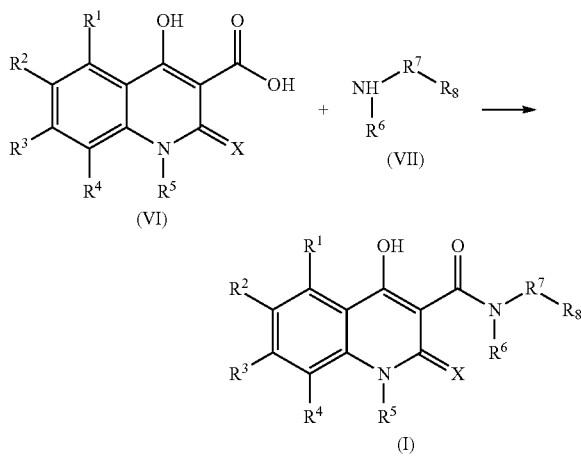

wherein R1, R2, R3, R4, R5, R6, R7, R8 and X in the compounds of the formulae (VI) and (VII) are defined as in the compounds of the formula (I). Additionally, functional groups can be present in protected form or in the form of a precursor group, which form is later converted into the final group.

The reaction of the carboxylic acids of the formula (VI) or reactive derivatives thereof with the amine of the formula (VII) to give the compounds of the formula I comprises the formation of an amide bond, and can be performed under standard conditions for such amide couplings. If a carboxylic acid of the formula (VI) is employed in the reaction, it is usually converted into a reactive derivative, which can be isolated or prepared in situ, or activated in situ by a customary amide coupling reagent. For example, the compound of the formula (VI) can be converted into a carboxylic acid chloride by treatment with thionyl chloride, oxalyl chloride or (1-chloro-2-methyl-propenyl)-dimethylamine, into a reactive ester, or into a mixed anhydride by treatment with an alkyl chloroformate like ethyl chloroformate or isobutyl chloroformate. Alternatively, the compound of formula (VI) can be activated with a reagent such as propanephosphonic anhydride, an N,N'-carbonyldiazole like N,N'-carbonyldiimidazole (CDI), a carbodiimide like N,N'-diisopropylcarbodiimide (DIC), N,N'-dicyclohexylcarbodiimide (DCC) or N-ethyl-N'-(3-dimethylaminopropyl)carbodiimide hydrochloride (EDC), a carbodiimide together with an additive like 1-hydroxybenzotriazole (HOBT) or 1-hydroxy-7-azabenzotriazole (HOAT), a uronium-based coupling reagent like O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), or a phosphonium-based coupling reagent like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromothpyrrolidinophosphonium hexafluorophosphate (PyBroP). The activation of the compound of the formula (VI) and the reaction of the activated compound of the formula (VI) or a reactive carboxylic acid derivative with the compound of the formula (VII) is generally carried out in an inert solvent, such as an ether like tetrahydrofuran (THF), dioxane or 1,2-dimethoxyethane (DME), or a hydrocarbon like toluene or a chlorinated hydrocarbon like dichloromethane or chloroform, or an amide like dimethylformamide (DMF) or N-methylpyrrolidin-2-one (NMP), for example, or a mixture of solvents, at temperatures from about 0° C. to about 60° C. in the presence of a suitable base such as a tertiary amine like triethylamine, ethyl-diisopropylamine, N-methylmorpholine or pyridine, or a basic alkaline metal compound such as an alkaline metal carbonate like sodium carbonate, potassium carbonate or cesium carbonate, for example. The carboxylic acids of the formula (VI), or compounds which instead of the carboxylic acid group depicted in formula (VI) contain a carboxylic acid derivative group, for example, a carboxylic acid chloride group, can be obtained from the corresponding esters, such as 5-ethyl-4-hydroxy-1-methyl-2-oxo-1,2-dihydroquinoline-3-carboxylic acid by saponification, as shown in FIG. 3.

Diagnostic Use

As disclosed by the present invention, quinoline-3-carboxamide compounds covalently linked to a label as disclosed elsewhere herein are well suited for use in the diagnosis of inflammatory processes because of their high binding affinity to S100A9, which is known as to be overexpressed and involved in many inflammatory disorders, such as inflammatory and cardiovascular diseases. In order to analyze the binding properties of the newly synthesized compounds to S100A9, the inventors of the present application developed a specific ELISA. When adding the novel S100A9 specific ligands of the present invention, TLR4-binding of S100A9 protein was markedly blocked, resulting in a decrease of signal given by the TLR4-S100A9 ELISA (FIG. 5). Thus, the data of the present invention confirm the binding specificity of CES271-Cy5.5 to S100A9. Accordingly, non-peptidic quinoline-3-carboxamide compounds as disclosed herein may be appropriate to specifically block the binding properties of S100A9 to TLR4.

Using FRI optical imaging and a synthesized optical probe based on the non-peptidic S100A9 ligand 3-quinolinecarboxamide coupled to Cy5.5® (CES271-Cy5.5), the present inventors could successfully demonstrate in vivo in a mouse model of contact dermatitis a high binding affinity to S100A9 (FIG. 6). Also, coinjection of 3-quinolinecarboxamide coupled to Cy7® (Cy7-CES271) and a Cy5.5-labeled anti-51009 antibody (Cy5.5-aS100A9) into inflamed and control ears revealed a highly significant correlation between the Cy7-CES271 and Cy5.5-aS100A9 signal in a mouse model of contact dermatitis (ICD), (FIG. 21). Moreover, CES271-Cy5.5 was used in myocardial infarction models, demonstrating accumulation of said compound in myocardial infarction in concordance to the presence of S100A9 shown by histological staining (FIG. 7). In atherosclerosis mouse model, FRI imaging data indicate high levels of S100A9 in high uptake areas of CES271-Cy5.5 and absence/very low level of S100A9 in low uptake areas of the labelled compound (FIG. 8). Furthermore, the binding constant of CES271-Cy5.5 to human and murine S100A9 could be determined by fluorimetric measurements (FIG. 15). Biodistribution of CES271-Cy5.5 in healthy Balb/c mice by the measurement of fluorescence intensity in various organs indicates a good tissues availability of said compound (FIG. 16). Additionally, the synthesized radioactive alternative [$^{99m}$Tc]FEB054 showed a very good blood serum stability (FIG. 17) and a suitable blood half-life. In vivo biodistribution experiments revealed a good availability of [$^{99m}$Tc] FEB054 in the blood and a predominant hepato-biliary elimination (FIG. 18). An increased accumulation of [$^{99m}$Tc] FEB054 in a mouse model of contact dermatitis (FIG. 19) and collagen induced arthritis (FIG. 20) could be demonstrated as well.

S100A9 is expressed very early in LPS-induced acute lung injury (ALI) and could serve as an imaging target for the early evaluation of similar diseases in the clinical setting. In the ALI model, S100A9 serum levels increased significantly with administered LPS dose and over time. Lungs of LPS treated mice showed significantly higher tracer levels were early on 6 h post induction CES271-Cy5.5 accumulated in the parenchyma with a ratio of up to 2.5, while the LPS-treated perfusion controls did not reveal significantly higher tracer accumulation in the parenchyma as compared to untreated animals (FIG. 22). Accordingly, CES271-Cy5.5 enables lung inflammation monitoring where perfusion based contrast agents fail.

Accordingly, the imaging data of the present invention underline the applicability of quinoline-3-carboxamide compounds covalently linked to a label in the diagnosis of inflammatory and cardiovascular diseases associated with S100A9 overexpression and accumulation at local site of inflammation.

Therefore, in one aspect, the present invention provides the use of any of the quinoline-3-carboxamide compounds covalently linked to a label as disclosed herein for use in a method of diagnosis, wherein the diagnosis is typically a diagnosis of an inflammatory disease. The term "diagnosing" or "diagnosis" when used herein means determining or detecting if a subject suffers from an inflammatory disease or disorder. However, where reference is made to "diagnosis" of an inflammatory disease, this should be taken to include both diagnosis of the disease itself, as well as susceptibility to the disease. Accordingly, the methods of diagnosis disclosed herein may also be employed as methods of providing indications useful in the diagnosis of an inflammatory disease. Typically, the inflammatory disease or disorder as described herein is associated with phagocyte and/or epithelial cell activation in said subject. This activation is accompanied by an increased expression and secretion of S100A9 by said cells, which binds to both the extracellular matrix and receptors such as TLR4 or RAGE on the immune cell surface, thereby amplifying inflammatory reactions. Thus, in a preferred embodiment, the inflammatory disease or disorder of the present invention is further associated with an overexpression and accumulation of S100A9 in said subject. The term "overexpression" is used herein to mean above the normal expression level of S100A9 protein in a particular tissue or at a local stage in said subject. The term "accumulation" when used herein refers to the enrichment of the overexpressed S100A9 protein in a particular tissue or at a local stage in said subject.

When applying the labeled quinoline-3-carboxamide compounds of the present invention for use in a method of diagnosing an inflammatory disease in a subject, in some embodiments the inflammatory disease is at local site of the inflammation. "At local site" when used herein means that S100A9 can be visualized in vivo at spatially limited areas in the tissue of a subject whereas biomarkers measured in the blood only reflect the systemic states, which is however strongly affected by factors like metabolism or blood clearance, limiting the specificity and sensitivity of these approaches. Accordingly, the compounds of the present invention in combination with the imaging techniques described elsewhere herein allow for the reliable detection of S100A9 when locally expressed during an inflammatory disease. Moreover, visualization of the compounds as disclosed herein enables the proof of local inflammation with unique sensitivity, allowing even the detection of subclinical, residual disease activity. Accordingly, in a preferred embodiment of the present invention, the inflammatory disease can be diagnosed at an early stage of inflammation. The term "early stage" as used herein encompasses, but is not limited to medical conditions in which the afflicted subject, e.g. the afflicted human subject, shows little to no perceptible exterior sign or symptoms of inflammation and the overall physical condition of said subject is apparently preserved, although some accumulation of S100A9 may be evident. Exterior signs or symptoms of inflammation include, but are not limited to classical signs of inflammation such as pain, heat, redness, rash, swelling, skin lesions or fever, which however are strongly dependent on the type of inflammatory disease and the place of occurrence in the body.

The term "disease" or "disorder" as used herein, refers to any physical state of a subject connected with incorrectly functioning organ, part, structure, or system of the body resulting from the effect of genetic or developmental errors, infection, poisons, nutritional deficiency or imbalance, toxicity, or unfavorable environmental factors, illness, sickness, or ailment. The term "disease" or "disorder" further includes any impairment of the normal physical state of the subject or one of its parts that interrupts or modifies the performance of vital functions that are typically manifested by distinguishing signs and symptoms. The term "inflammatory" or "inflammation" when used herein refers to a part of complex biological response of vascular tissues to harmful stimuli, such as pathogens, damaged cells, or irritants. In this context, inflammation is a protective response involving host cells, blood vessels, and proteins and other mediators that is intended to eliminate the initial cause of cell injury, as well as the necrotic cells and tissues resulting from the original insult, and to initiate the process of repair. Within the scope of the present invention, the inflammation described herein can be generally classified as either acute or chronic. The acute inflammation is the initial response of the body to harmful stimuli and is achieved by the increased movement of plasma and leukocytes (especially granulocytes) from the blood into the injured tissues, involving the local vascular system, the immune system, and various cells within the injured tissue. Prolonged inflammation, also known as chronic inflammation, leads to a progressive shift in the type of cells present at the site of inflammation and is characterized by simultaneous destruction and healing of the tissue from the inflammatory process. Thus, the term "Inflammatory diseases" or "inflammatory disorder" when used herein refer to any physical state of the subject of the present invention which is related to a disease or a physical reaction connected with the occurrence of inflammation in said subject. Particularly, the inflammatory disease or disorder of the present invention is preferably related to an increased phagocyte and/or epithelial cell activation and a S100A9 overexpression and accumulation in said subject.

Many inflammatory and cardiovascular diseases or disorders are known as to be associated with an increased phagocyte and/or epithelial cell activation and are within the scope of the present invention. Since these cells express and locally secrete high levels of the S100 protein complex S100A8/S100A9 which acts as so called alarmin or Danger Associated Molecular Pattern (DAMP) molecule with potent pro-inflammatory capacities, many inflammatory and cardiovascular diseases are associated with an overexpression and accumulation of S100A9 (Vogl et al. 2007, Loser et al. 2010, Chan et al. 2012). In some embodiments the inflammatory disease of the present invention is dermatitis. In some embodiments the inflammatory disease is atherosclerosis. In some embodiments the inflammatory disease is psoriasis. In some embodiments the inflammatory disease is an autoimmune disease. In some embodiments the inflammatory disease is arthritis. In some embodiments the inflammatory disease is allergies. In some embodiments the inflammatory disease is cardiovascular processes. In some embodiments the inflammatory disease is local and systemic infections. In some embodiments the inflammatory disease is a neuroinflammatory disease. In some embodiments the inflammatory disease is acute lung injury (ALI). In some embodiments the inflammatory disease is a tumor.

A subject when used herein includes mammalian and non-mammalian subjects. Preferably the subject of the present invention is a mammal, including human, domestic and farm animals, nonhuman primates, and any other animal that has mammary tissue. In some embodiment the mammal is a mouse. In some embodiment the mammal is a rat. In some embodiment the mammal is a guinea pig. In some embodiment the mammal is a rabbit. In some embodiment the mammal is a cat. In some embodiment the mammal is a dog. In some embodiment the mammal is a monkey. In some embodiment the mammal is a horse. In a most preferred embodiment the mammal of the present invention is a human. A subject also includes human and veterinary patients.

According to another aspect, the present invention provides a method of diagnosing an inflammatory disease in a subject, comprises (a) administering to said subject any of the labelled quinoline-3-carboxamide compounds described herein above, (b) detecting the administered compounds using in vivo non-invasive molecular imaging techniques, thereby collecting imaging data, and (c) comparing the imaging data received in step (b) to reference imaging data. Here, the method of diagnosing comprises an active administration of any of the compounds according to the present invention to a subject. The administration of the compound may be carried out variously. In some embodiments the compounds as disclosed herein above are administered intravenously. In some embodiments the administration of the compound is carried out orally. In some embodiments the administration is carried out parenterally. In some embodiments the administration is carried out subcutaneously. In some embodiments the administration is carried out intramuscularly. In some embodiments the administration is carried out intraperitoneally. In some embodiments the administration is carried out by intranasal instillation. In some embodiments the administration is carried out by implantation. In some embodiments the administration is carried out by intracavitary instillation. In some embodiments the administration is carried out by intravesical instillation. In some embodiments the administration is carried out intraocularly. In some embodiments the administration is carried out intraarterially. In some embodiments the administration is carried out intralesionally. In some embodiments the administration is carried out transdermally. In some embodiments the administration is carried out by application to mucous membranes. Preferably, the administration is carried out intravenously, subcutaneously, intralesionally, or by application to mucous membranes. In some embodiments, also the use of any of the compounds according to the present invention in a method of diagnosis comprises administering said compound to the subject.

According to another aspect, the present invention further provides a non-invasive method of detecting or imaging accumulation of S100A9 in the body of a subject to whom any of the labeled quinoline-3-carboxamide compounds described herein above has been pre-delivered, comprising (a) detecting the administered compound using an in vivo non-invasive molecular imaging technique, thereby collecting imaging data, and (b) comparing the imaging data received in step (a) to reference imaging data. Accordingly, the method of detecting or imaging S100A9 in the body of a subject does not comprise an active administration of any of the compounds according to the present invention, but refers to a situation, where any of the compounds according to the present invention has been pre-delivered to said subject. "Pre-delivered" includes in this regard, that the quinoline-3-carboxamide compounds covalently linked to a label have been delivered to the subject prior to the methods and uses of the present invention (and all associated embodiments), i.e. before the methods of the invention are to be carried out. The term "detecting" when used herein refers to the visualization and the qualitative analysis of the presence or absence of S100A9 in vivo using the compounds of the present invention and any of the molecular imaging techniques described elsewhere herein.

The signal in the imaging data received from the subject during the detection step as described in various aspects of the present invention can be considered as the reflected signal received from the label of the administered quinoline-3-carboxamide compound. Accordingly, when comparing the collected imaging data to reference imaging data, the method equally comprises comparing the signal received from the label of the administered compound to a detected reference signal. Thus, in particular, the methods and uses of the present invention allow the comparison and quantification of in vivo signals. The reference imaging data or the detected reference signal typically derives from a reference subject, which is a healthy subject to whom the same labelled quinoline-3-carboxamide compound of the present invention has been delivered. The term "healthy subject" when used herein refers to a subject not suffering from an inflammatory disease or disorder associated with phagocyte and/or epithelial cell activation and overexpression and accumulation of S100A9. In this regard, the collected imaging data of the subject as described herein indicate the level of S100A9 in said subject, and the reference imaging data indicate the level of S100A9 in the reference subject. Accordingly, an increased signal in the imaging data from the subject as compared to reference imaging data indicates the presence of an inflammatory disease in said subject. Alternatively, no difference in the signal in the imaging data from the subject as compared to reference imaging data indicates no presence of an inflammatory disease in said subject.

To visualize biological processes non-invasively in vivo and to be able to do quantifications, an injectable imaging agent is required. According to the present invention, quinoline-3-carboxamide compounds covalently linked to a label can be applied to visualize inflammatory processes associated with an increased accumulation of S100A9 at local site, using non-invasive molecular imaging techniques to collect imaging data. These compounds comprise a label, which can be detected highly sensitive and a ligand exhibiting high affinity towards the desired target. "Non-invasive" as used herein means that no break in the skin of a subject is created, for example, an incision, and there is no contact with the mucosa, or skin break, or internal body cavity beyond a natural or artificial body orifice.

Using different imaging labels such as SPECT labels, PET labels, optical imaging labels, ultrasound labels or photoacoustic labels, the compounds of the present invention are well suited to detect molecular level of S100A9 at local site of inflammation when applying various molecular imaging techniques. As demonstrated by the data described herein, the combination of known imaging techniques and the novel non-peptidic quinoline-3-carboxamide compounds covalently linked to a label allow for the necessary cellular and molecular specificity and sensitivity to detect inflammatory disease activity itself, and image S100A9 at molecular level in inflammatory disease models.

Various aspects of the present invention comprise the detection of labelled non-peptidic quinoline-3-carboxamide compounds using different non-invasive molecular imaging techniques. In vivo optical molecular imaging is typically performed on small animals to study the physiologic, pathologic or pharmacologic effects of various drugs or diseases. Molecular imaging can also be performed on humans, and the present invention underlines that molecular imaging provides substantial advances in diagnostic imaging. The benefits of in vivo imaging of small animals are significant because it allows processes and responses to be visualized in real-time in their native environments, and allows longitudinal studies to be performed using the same small animal over time, allowing evaluation of disease progression or response to treatment. Further, in vivo imaging of small animals reduces the number of animals required for a study, and can reduce the variance in studies where disease manifestation varies from animal to animal.

In some embodiments, the compounds of the present invention are covalently linked to a single photon emission tomography (SPECT) label, e.g. labels comprising $^{99}$mTc, $^{123}$I, or $^{125}$I, as described elsewhere herein. These labels particularly allow for the application of said compounds in SPECT imaging, a nuclear medicine tomographic imaging technique using gamma rays. SPECT is very similar to conventional nuclear medicine planar imaging using a gamma camera, but is also able to provide true 3D information. This information is typically presented as cross-sectional slices through the patient, but can be freely reformatted or manipulated as required. The technique requires delivery of a gamma-emitting radioisotope into the patient, normally through injection into the bloodstream. Most of the time, a marker radioisotope is attached to a specific ligand to create a radioligand, whose properties bind it to certain types of tissues. This marriage allows the combination of ligand and radiopharmaceutical to be carried and bound to a place of interest in the body, where the ligand concentration is seen by a gamma-camera.

In some embodiments the compounds of the present invention are covalently linked to a positron emission tomography (PET) label, e.g. a label comprising $^{18}$F, as described elsewhere herein, which allows for the use of said compounds in the non-invasive molecular imaging technique PET. PET is a nuclear medicine, functional imaging technique that produces a three-dimensional image of functional processes in the body. The system detects pairs of gamma rays emitted indirectly by a positron-emitting radionuclide (tracer), which is introduced into the body on a biologically active molecule. Three-dimensional images of tracer concentration within the body are then constructed by computer analysis. In modern PET-CT scanners, three dimensional imaging is often accomplished with the aid of a CT X-ray scan performed on the patient during the same session, in the same machine. As described in the state of the art, the biologically active molecule chosen for PET is generally fluorodeoxyglucose (FDG), an analogue of glucose, the concentrations of tracer imaged will indicate tissue metabolic activity by virtue of the regional glucose uptake. However, many other radioactive tracers can be used in PET to image the tissue concentration of many other types of molecules of interest.

In further embodiments, the quinoline-3-carboxamide compounds of the present invention are covalently linked to optical imaging labels such as dyes, e.g. FITC, DiR or Alexa Fluor® 488 as described elsewhere herein. These dyes are particularly useful in intraoperative applications such as abscess excision, tumor location and size and endoscopy. In some embodiments the compounds of the present invention are covalently linked to fluorophores, e.g. polymethine dyes. Such optical imaging labels allows for the use of quinoline-3-carboxamide compounds in optical imaging techniques. Classical optical imaging techniques rely on the use of visible, ultraviolet, and infrared light in imaging. Chemical imaging or molecular imaging involves inference from the deflection of light emitted from e.g. a laser or infrared source to structure, texture, anatomic and chemical properties of material. The skilled person is aware of different optical imaging systems applicable in combination with the compounds of the present invention. These systems are mainly divided into diffusive and ballistic imaging systems, which can all be used within the scope of the present invention.

In some embodiments, quinoline-3-carboxamide compounds may be covalently linked to an ultrasound label as disclosed elsewhere herein, which allows for the use of the non-peptidic quinoline-3-carboxamide compounds in diagnostic sonography. Ultrasonography is an ultrasound-based diagnostic imaging technique used for visualizing internal body structures including tendons, muscles, joints, vessels and internal organs for possible pathology or lesions.

In some embodiments, the quinoline-3-carboxamide compounds of the present invention are covalently linked to photoacoustic labels (absorbers) as described elsewhere herein. Photoacoustic imaging, as a hybrid biomedical imaging modality, is developed based on the photoacoustic effect. In this context photoacoustic labels with and without fluorescence properties can be applied. Generally, in photoacoustic imaging, non-ionizing laser pulses are delivered into biological tissues. When radio frequency pulses are used, the technology is referred to as thermoacoustic imaging. Some of the delivered energy will be absorbed and converted into heat, leading to transient thermoelastic expansion of the molecule ultrasonic waves and thus wideband (e.g. MHz) ultrasonic emission. The generated ultrasonic waves are then detected by ultrasonic transducers to form images. Here it is known that optical absorption is closely associated with physiological properties. As a result, the magnitude of the ultrasonic emission (i.e. photoacoustic signal), which is proportional to the local energy deposition, reveals physiologically specific optical absorption contrast. 2D or 3D images of the targeted areas can then be formed.

While it is possible to administer the compounds of the present invention as described herein above directly without any formulation to a subject, in one aspect of the present invention the compounds are preferably employed in the form of a pharmaceutical or diagnostic formulation composition, comprising a pharmaceutically or diagnostically acceptable carrier, diluent or excipient and any of the compound of the present invention. Accordingly, the present invention relates to a diagnostic composition comprising any of the quinoline-3-carboxamide compounds covalently linked to a label as described herein above and a pharmaceutically or diagnostically acceptable excipient. Moreover, the present invention relates to the use of a compound as disclosed herein above for the preparation of a diagnostic composition for diagnosing an inflammatory disease.

The term "diagnostic composition" when used herein refers to a composition comprising any one of the quinoline-3-carboxamide derivatives of the present invention and a pharmaceutically or diagnostically acceptable carrier, diluent or excipient, which can be applied for used in diagnosis. The carrier used in combination with the compound of the present invention is water-based and forms an aqueous solution. An oil-based carrier solution containing the compound of the present invention is an alternative to the aqueous carrier solution. Either aqueous or oil-based solutions further contain thickening agents to provide the composition with the viscosity of a liniment, cream, ointment, gel, or the like. Suitable thickening agents are well known to those skilled in the art. Alternative embodiments of the present invention can also use a solid carrier containing the diagnostic compound for use in diagnosis as disclosed elsewhere herein. This enables the alternative embodiment to be applied via a stick applicator, patch, or suppository. The solid carrier further contains thickening agents to provide the composition with the consistency of wax or paraffin.

Pharmaceutically or diagnostically acceptable excipients according to the present invention include, by the way of illustration and not limitation, diluent, disintegrants, binding agents, adhesives, wetting agents, polymers, lubricants, gliands, substances added to mask or counteract a disagreeable texture, taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The diagnostic compositions can additionally include preservatives, solubilizers, stabilizers, wetting agents, emulsifiers, sweeteners, colorants, flavorings, buffers, coating agents, or antioxidants. Suitable pharmaceutical and diagnostic carriers are described in Remington's Pharmaceutical Sciences, Mack Publishing Company, a standard reference text in this field. The use of the diagnostic composition of the present invention as a diagnostic kit for diagnosing inflammatory disease associated with phagocyte and/or epithelial cell activation and overexpression and accumulation of S100A9 is also encompassed by the present invention.

In a further aspect, the present invention provides a method of evaluating whether a subject may be at risk of developing an inflammatory disease associated with phagocyte and/or endothelial cell activation in a patient, comprising: (a) administering to said subject any of the compounds as disclosed herein above, (b) detecting the administered compound using an in vivo non-invasive molecular imaging technique, thereby collecting imaging data, and (c) comparing the imaging data received in step b) to reference imaging data. In this regard, the term "evaluating the risk" refers to any procedure or method used to assess whether or not a subject patient may develop an inflammatory disease associated with phagocyte and/or endothelial cell activation within a specific foreseeable period of time. Thus, a method of evaluating the risk of a subject of developing an inflammatory disease might be particularly useful when a subject has already suffered from any of the inflammatory diseases described herein and is of increased risk of recurrence of said disease. In this regard, the risk of the subject of developing said inflammatory disease can already be detected at an early stage and appropriate therapeutic measures and treatments can be started in time. The S100A9 level in said subject may be determined using any desired technique known to those skilled in the art and methods disclosed herein. A significant increased signal in the imaging data from the subject as compared to reference imaging data indicates that said subject is at higher risk of developing an inflammatory disease associated with phagocyte and/or epithelial cell activation. On the contrary, a signal in the imaging data at a normal level as compared to reference imaging data indicates that said subject is at lower risk of developing an inflammatory disease associated with phagocyte and/or epithelial cell activation.

According to another aspect, the present invention refers to a method of monitoring or evaluating the progression of an inflammatory disease or disorder associated with phagocyte and/or epithelial cell activation in a patient, the method comprising: (a) administering to said subject any of the compounds as disclosed herein above, (b) detecting the administered compound using an in vivo non-invasive molecular imaging technique, thereby collecting imaging data, and (c) comparing the imaging data received in step (b) to reference imaging data obtained from said patient at an earlier date, wherein the result of the comparison of (c) provides an evaluation of the progression of the inflammatory disease associated with phagocyte and/or epithelial cell activation in said patient. In this regards, the term "monitoring or evaluating the progression" refers to any procedure or method used in vivo to assess whether or not a patient suffering from an inflammatory disease or disorder associated with phagocyte and/or epithelial cell activation is responsive to treatment with a therapeutic compound. In this context, also tumor associated inflammation as surrogate marker for e.g. therapy response can also be assessed using any of the methods of the present invention.

In particular, a method of monitoring or evaluating the progression of an inflammatory disease or disorder relates to monitoring or evaluating the level of S100A9 in a subject at local stage prior, during and after therapy with a therapeutic compound. The term "therapeutic compound" as used herein refers to any compounds suitable to treat an inflammatory disease characterized by phagocyte and/or epithelial cell activation and overexpression and accumulation of S100A9.

As disclosed herein, a method of monitoring or evaluating the progression of an inflammatory disease or disorder might be particularly useful when treating a patient suffering from an inflammatory disease or disorder associated with phagocyte and/or epithelial cell activation with any medicament for alleviating or healing said inflammatory disease. Accordingly, the method of monitoring as described herein particularly refers to in vivo monitoring the therapeutic efficacy of a drug used in the treatment of inflammatory disorders. Hence, conclusions can be drawn during and/or after the treatment of a subject with the medicament as to whether said medicament may improve symptoms of an inflammatory disease when comparing to the physical conditions before start of treatment. Moreover, such monitoring or evaluation may help an attending physician to obtain the appropriate information to set the appropriate therapy conditions for the treatment of said inflammatory disease. A significantly increased signal in the imaging data from the subject as compared to reference imaging data obtained from said patient at an earlier date indicates a progression of the inflammatory disease associated with phagocyte and/or epithelial cell activation in said patient, whereas no change or decrease in the signal in the imaging data from the subject as compared to reference imaging data obtained from said patient at an earlier date indicates no progression or a regression of the inflammatory disease associated with phagocyte and/or epithelial cell activation in said patient.

In a further aspect, the present invention provides a method of imaging an inflammatory disease in a subject, comprising: (a) administering to said subject any of the compounds as disclosed herein above, and (b) detecting the administered compound using an in vivo non-invasive molecular imaging method, thereby collecting imaging data. The term "imaging" when used herein refers to the optical visualization of low levels of S100A9 or S100A9 accumulation at local site of inflammation under in vivo conditions, using the quinoline-3-carboxamide compounds covalently linked to a label and any of the molecular imaging techniques described elsewhere herein. Accordingly, the term "imaging" as used herein preferably means "molecular imaging". Molecular imaging is generally used to explore physiological processes in real-time in vivo and to diagnose or certain diseases due to molecular abnormalities by means of imaging techniques. Moreover, the method of imaging may also be applicable in recurrence diagnosis.

Although the compounds of the present invention are particularly useful to be applied under in vivo conditions, a use of said compounds in vitro is also within the scope of the present invention. Accordingly, the present application provides an in vitro method of diagnosing an inflammatory disease in a subject to whom any of the compound disclosed herein has been pre-delivered, comprising: (a) analyzing a sample taken from said subject, (b) detecting said pre-delivered compound using a non-invasive molecular imaging method, thereby collecting imaging data, (c) comparing the imaging data received in step (b) to reference imaging data. To this end, it is envisaged to compare the imaging data of a sample from a subject to whom the compound of the present invention has been pre-delivered to imaging data of a reference sample taken from a reference subject. Here, an increased signal in the imaging data from the subject as compared to reference imaging data indicates the presence of an inflammatory disease in said subject, whereas no difference in the imaging signal in the imaging data from the subject as compared to reference imaging data indicates no presence of an inflammatory disease in said subject. In this context, a sample may be analyzed that has been obtained from the subject of the present invention. The sample may be any biological sample taken from said subject and being appropriate to diagnose an inflammatory disease associated with phagocyte and/or epithelial cell activation in said subject. Non-limiting examples of useful samples may include blood samples, tissues samples, body fluid samples, skin samples or any other samples known to those skilled in the art for use in in vitro diagnosis.

(A): Quality control via Co-injection. Chromatogram of the free ligand and the corresponding Re-complex (red line) and of $^{99m}$Tc-FEB054 (blue line) performed by gradient-HPLC using a Knauer system with a K-500 pump, a K-501 pump, a K-2000 UV detector, a NaI(TI) Scintibloc 51 SP51 γ-detector and a reversed phase C$_{18}$ column (ACE-126-2510, 10 mm×250 mm). Eluent A: water (0.1% TFA). Eluent B: Methanol (0.1% TFA). Gradient from 70% A to 0% A over 30 minutes, holding for 8 minutes and back to 70% A over 5 minutes at a flow rate of 5.5 ml min$^{-1}$, detection at λ=254 nm.

(B): Mass analysis for product identification ($^{99m}$Tc-FEB054) on trace level: ESI-HR-MS System: Thermo Fisher Scientific (Bremen, Deutschland), Exactive; scan range: m/z 98-2000; resolution: Ultra High (100000@1 Hz); AGC target: balanced; maximum inject time: 1000 ms. Parameter: Sheath gas flow rate: 40; Aux gas flow rate: 5; Sweep gas flow rate: 0; Spray voltage in |kV|: 3.8; Capillary temp in ° C.: 300; Capillary voltage in V: 50 (pos), −87.5 (neg); Tube lens voltage in V: 90 (pos), −130 (neg); Skimmer voltage: 22 (pos), −30 (neg).

Figure 12:
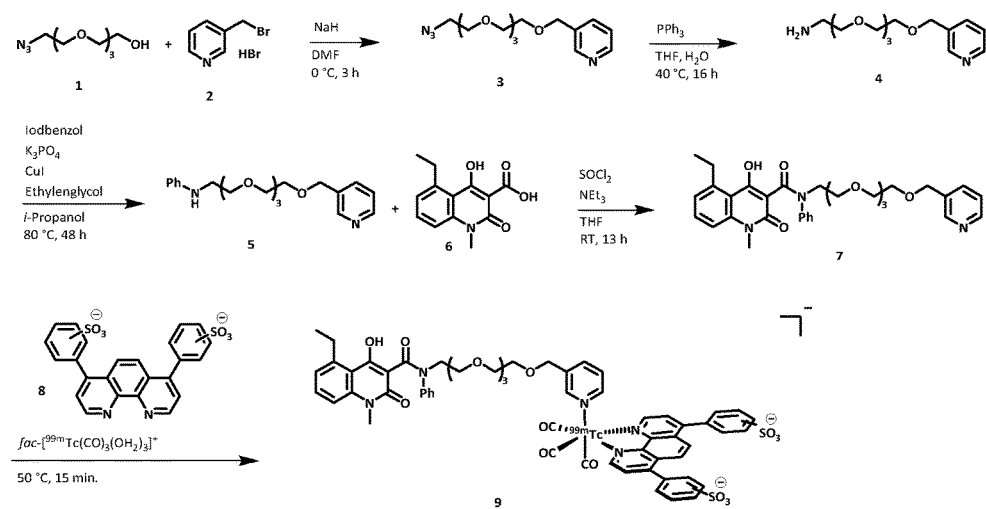

FIG. 12: Overview of the synthesis of fac-[$^{99m}$Tc(bathophenanthrolinedisulfonic acid)(CO)$_3$(5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide)]$^-$ ($^{99m}$Tc-FEB105) as a S100A9 ligand for single photon emission tomography (SPECT).

Figure 13:
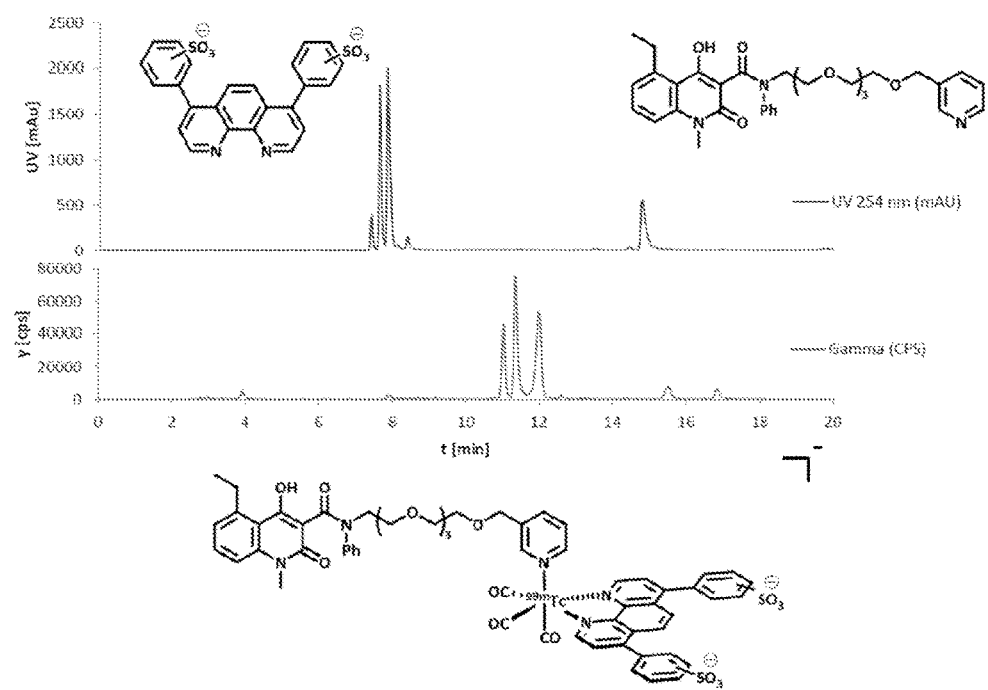

FIG. 13: Characterisation of fac-[$^{99m}$Tc(bathophenanthrolinedisulfonic acid)(CO)$_3$(5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide)]$^-$ ($^{99m}$Tc-FEB105). Chromatogram of the UV and gamma channel. The UV channel shows the signal given by the co ligand with a retention time around 8 minutes. At a retention time of 14.8 minutes, the signal given by Precursor can be observed. In the gamma channel, three peaks with retention times between 11 and 12 minutes are caused by $^{99m}$Tc-FEB105.

Figure 14:
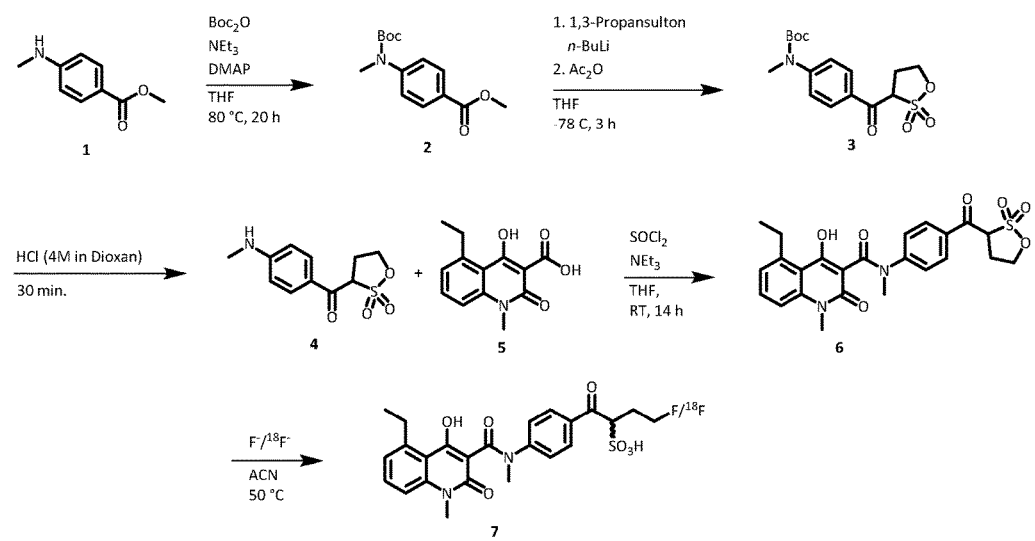

FIG. 14: Overview of the synthesis of 1-[4-(5-ethyl-4-hydroxy-N,1-dimethyl-2-oxo-1,2-dihydroquinoline-3-carboxamido)phenyl]-4-fluoro-1-oxobutane-2-sulfonic acid as a S100A9 ligand for positron emission tomography (PET).

Figure 15:
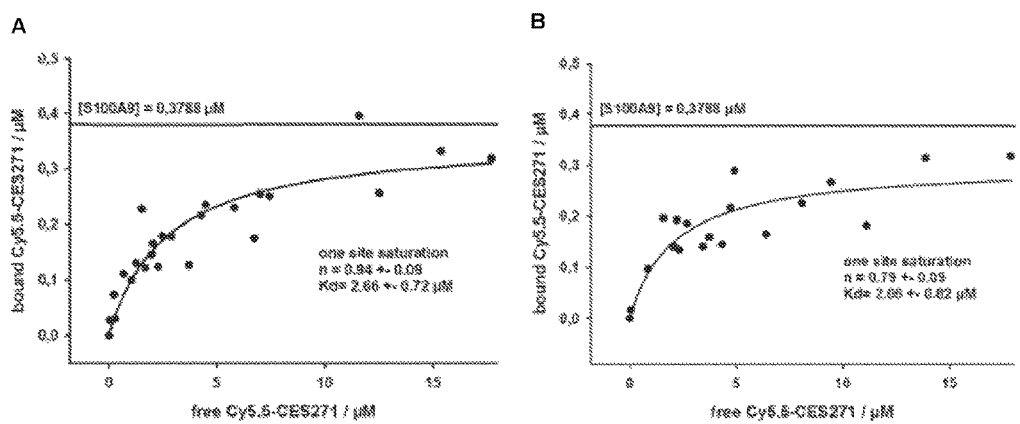

FIG. 15: Binding of Cy5.5-CES271 to human and murine S100A9. Estimation of the binding constant of Cy5.5-CES271 to human (A) and murine (B) S100A9. The constant was calculated using the one site saturation regression model. Each dot represents the mean value of four independent experiments.

Figure 16:
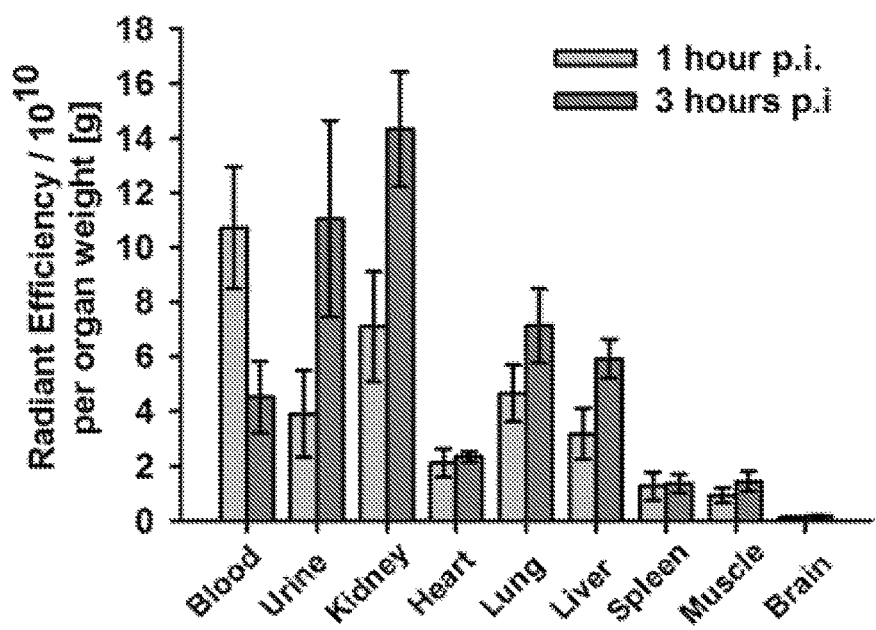

FIG. 16: Biodistribution of Cy5.5-CES271 in healthy Balb/c mice. The tracer was intravenously injected at a dose of 2 nmol per mouse. The tracer accumulation was measured 1 and 3 h post injection (n=5 for each time point Data shows a decrease of tracer concentration in the blood between 1 h and 3 h post injection, while in the same time interval the tracer concentration in the urine increases significantly, reflecting renal tracer elimination. Kidney, liver and lung present with higher tracer concentrations at 3 h post injection, which can be partly related to tracer metabolization. In other tissues analysed (heart, spleen, muscle, brain) tracer concentrations are at the same level when comparing 1 h and 3 h post injection time points.

Figure 17:
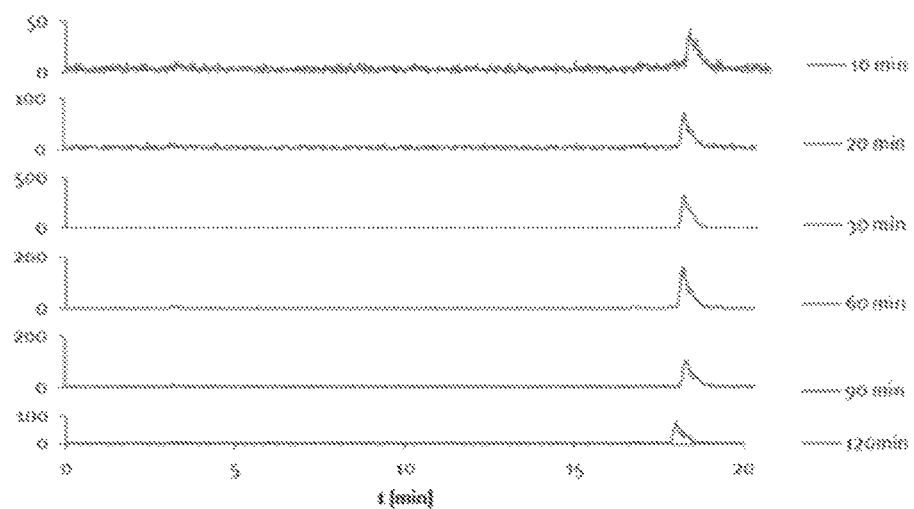

FIG. 17: Human serum blood stability of [$^{99m}$Tc]FEB054. In human blood serum stability tests, no decomposition was observed over a period of 120 min. Blood serum stability was tested in freshly prepared human blood serum at 37° C. Samples were taken after 10, 20, 30, 60, 90 and 120 minutes and analysed using a gradient HPLC system. 5 MBq of [$^{99m}$Tc]FEB054 in 20 μL PBS buffer was added to 200 μL of a freshly prepared human blood serum sample and incubated at 37° C. After 10, 20, 30, 60, 90 and 120 minutes, 20 μL were separated and diluted with 50 μL dichloromethane and 50 μL methanol. After centrifugation, 10 μL of the solution were analyzed via gradient-HPLC using a Knauer system with two Smartline 1000 pumps, Smartline UV detector 2500 (Herbert Knauer GmbH), a GabiStar γ-detector (Raytest lsotopenmessgeräte GmbH) and a reversed phase C$_{18}$ column (Nucleosil 100-5 C-18 column 4.6 mm×250 mm). Eluent A: water (0.1% TFA). Eluent B: Methanol (0.1% TFA). Gradient from 70% A to 0% A over 15 minutes, holding for minutes and back to 70% A over 5 minutes at a flow rate of 5.5 ml min$^{-1}$, detection at λ=254 nm.

Figure 18:
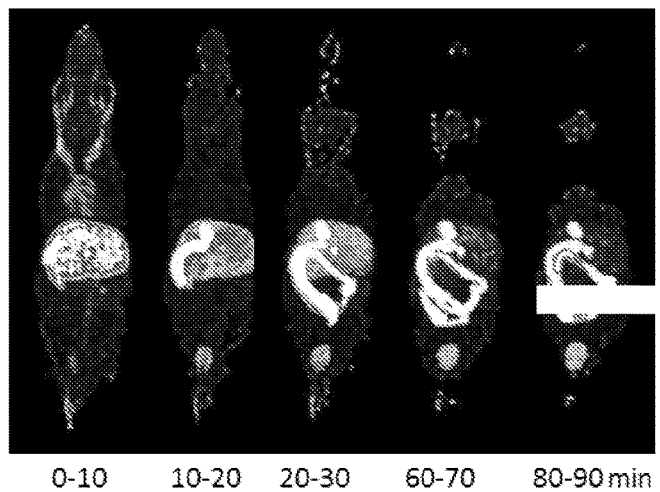
Figure 18:
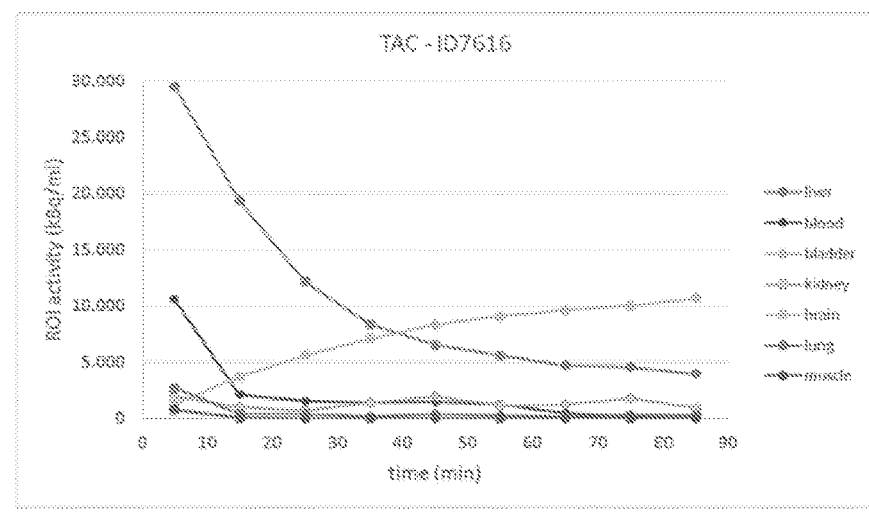

FIG. 18: Biodistribution (A) and elimination (B) of [$^{99m}$Tc]FEB054 in healthy Balb/c mice. The tracer was intravenously injected at a dose of 62 MBq per mouse. The tracer accumulation and elimination was measured 0-90 min post injection. In vivo biodistribution experiments show a good tracer availability in the blood in the first 10 minutes and predominant hepato-biliary elimination within 20 min resulting in intensive accumulation of the tracer in the liver and intestines.

Figure 19:
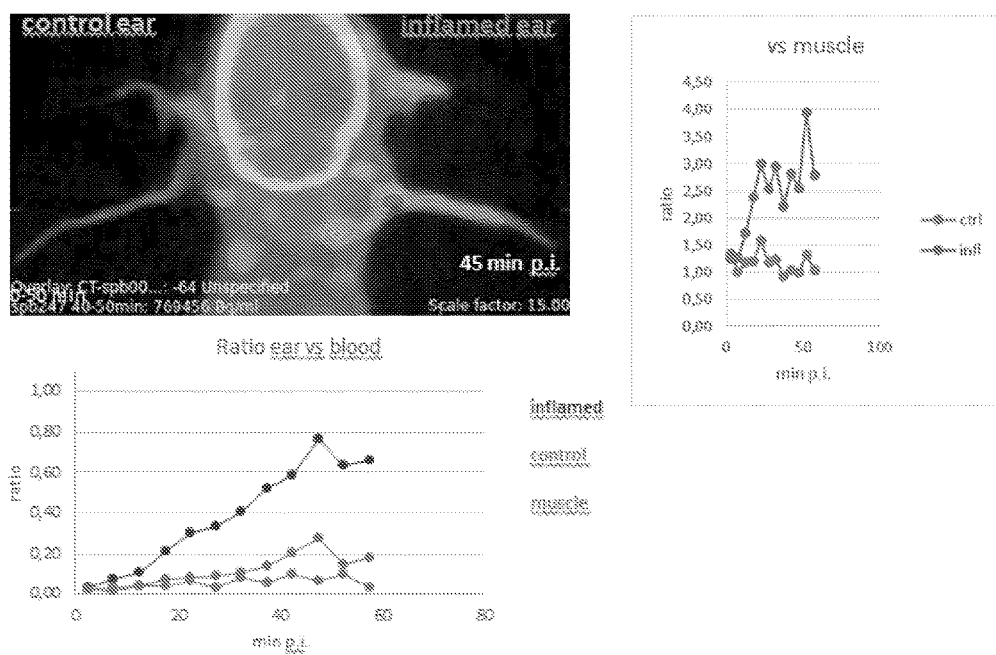

FIG. 19: Accumulation of [$^{99m}$Tc]FEB054 in the inflamed ear and muscle in a mouse model of contact dermatitis (ICD). The tracer was intravenously in a mouse model of contact dermatitis of the left ear in WT mice (=inflamed, right hand side) at a dose of 66 MBq per mouse and measured 0-60 min post injection. The given image example 45 minutes post injection reveals a higher tracer uptake in the inflamed ear as compared to the healthy control ear.

Quantitative image analysis shows increasing uptake ratios of tracer in the inflamed ear versus blood and muscle, respectively.

Figure 20:
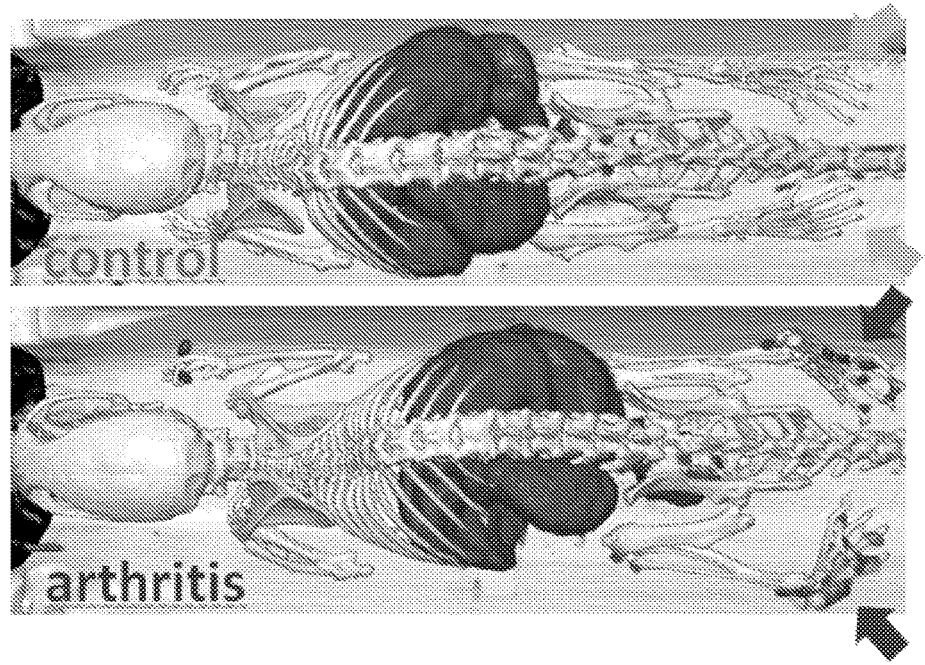

FIG. 20: Accumulation of [$^{99m}$Tc]FEB054 in a mouse model of collagen induced arthritis. The tracer was intravenously injected at a dose of 55 MBq per mouse. The upper image shows a SPECT/CT-scan of a healthy control mouse, the lower image a SPECT/CT scan of an arthritis mouse. The tracer distribution was measured in vivo 60 min post injection using SPECT/CT. The volume rendered images (CT: grey-white color scale, [$^{99m}$Tc]FEB054-SPECT: red color scale) of two representative mice show tracer accumulation in the inflamed joints of the hind limbs in the arthritis mouse (red arrows) in clear contrast to the hind limbs of a healthy control mouse (green arrows). Besides this mouse model specific finding, SPECT images show intensive tracer accumulation in liver, intestines, kidneys and the urinary bladder.

Figure 21:
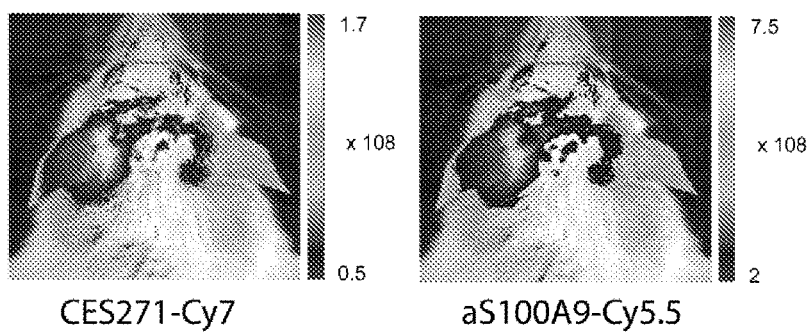
Figure 21:
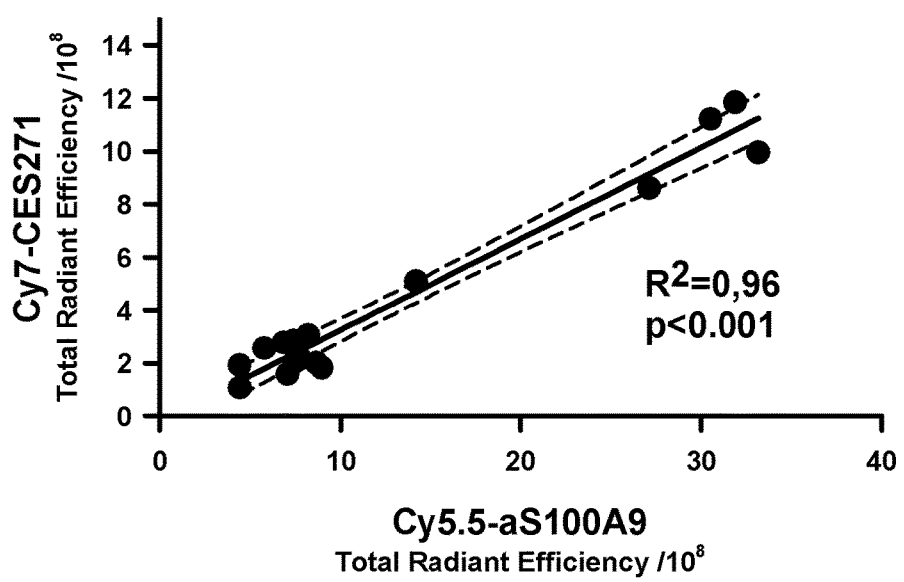

FIG. 21: FRI images of Cy5.5-CES271 and Cy7-CES271 in a mouse model of contact dermatitis (ICD). (A) Representative Fluorescence Reflectance images of a Cy7-CES271 and Cy5.5-aS100A9 coinjected animal. The left panel shows the signal recorded in the Cy7 channel, representing the Cy7-CES271 accumulation. The right panel shows the Cy5.5-aS100A9 accumulation. (B) Comparison of the Total Radiant Efficiency in inflamed and control ears reveals highly significant correlation between the Cy7-CES271 and Cy5.5-aS100A9 signal ($R^2$=0.96; n=8; p<0.001).

Figure 22:
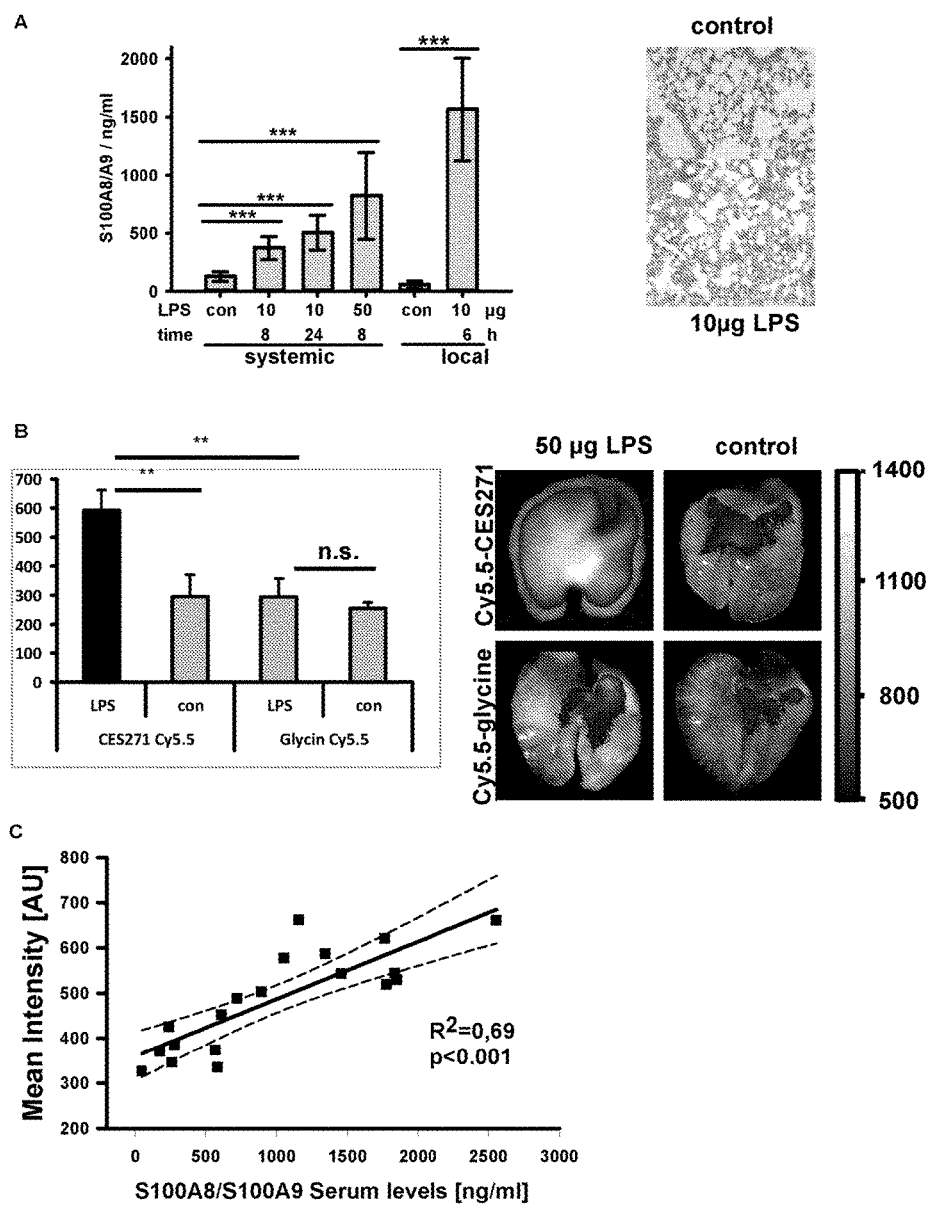

FIG. 22: Accumulation of Cy5.5-CES271 in a mouse model of acute lung inflammation (ALI). (A) At different time points after the intranasal application of either 10 pg or 50 pg LPS the local and systemic levels of S100A8/S100A9 are compared to control animals. Exemplary paraffin sections of inflamed and healthy lung tissue, taken at 8 h after LPS (10 pg) application were stained for S100A9-expression. Histological data of control (upper image) and lung inflammation (lower image) confirmed local expression of these proteins. (B) The comparison of the tracer accumulation in explanted mice lungs 3 h and 6 h after intranasal application of 50 pg LPS and parallel tracer injection is displayed. 50 pg LPS treated mice injected with glycine saturated Cy5.5 served as perfusion controls. (C) S100A8/S100A9 serum levels of LPS treated and control animals are correlated with the measured Mean Fluorescence Intensity over the lungs ($R^2$=0.69; n=19; p<0.001).

EXAMPLES

The following examples illustrate the invention. These examples should not be construed as to limit the scope of this invention. The examples are included for purposes of illustration and the present invention is limited only by the claims. The person of skill in the art will understand that other synthetic routes and variations to the quinoline-3-carboxamide compound, linker, and/or label described below are possible and within the scope of the present disclosure.

Experimental Details for the Synthesis of Cy5.5-CES271

Diethyl 2-(4-nitro-3-oxo-3H-isobenzofuran-1-ylidene)malonate

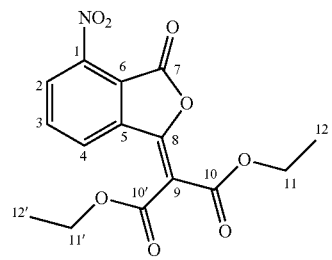 [SMILES: CCOC(=O)C(C(=O)OCC)=C1OC(=O)c2c1cccc2[N+](=O)[O-]]

To diethyl malonate (152 mL, 160 g, 1 mol), acetic anhydride (480 mL, 519 g, 5.1 mol) and triethylamine (137 mL, 99.2 g, 0.98 mol) was added at 35° C. under slight cooling (temperature should be maintained between 35 and 40° C.) 3-nitrophthalic acid anhydride (193.1 g, 1 mol). After stirring for 2 h at 40° C. and cooling to room temperature, the mixture was poured onto crushed ice (1.4 kg) and hydrochloric acid (32% w/v; 186 mL). After stirring for 30 min, the solvent was decanted and the residue suspended with 360 mL acetone. The precipitate was isolated by suction, washed with cold acetone and dried in vacuo. Yield: 293.2 g (0.87 mol; 87%)

mp.: 169° C. (acetone)

$^1$H NMR (600 MHz, chloroform-d)

δ [ppm]=9.01 (dd, $^3J_{H,H}$=8.1 Hz, $^4J_{H,H}$=0.8 Hz, 1H, 2-CH), 8.11 (dd, $^3J_{H,H}$=7.9 Hz, $^4J_{H,H}$=0.8 Hz, 1H, 4-CH), 7.98 (m, 1H, 3-CH), 4.40, 4.38 (q, $^3J_{H,H}$=7.1 Hz, 4H, 11-CH, 11'-CH), 1.37, 1.36 (t, $^3J_{H,H}$7.1 Hz, 6H, 12-CH, 12'-CH).

$^{13}$C NMR (151 MHz, chloroform-d)

δ [ppm]=162.8, 162.3 (s, C-10, C-10'), 158.5 (s, C-8), 152.5 (s, C-7), 146.9 (s, C-1), 138.2 (s, C-5), 136.5 (d, C-3), 131.7 (d, C-2), 127.6 (d, C-4), 118.5 (s, C-6), 112.0 (s, C-9), 62.7 (t, C-11, C-11'), 14.1, 14.1 (q, C-12, C-12').

MS (ESI$^+$): m/z=

358.0536; calculated [C$_{15}$H$_{13}$NO$_8$]Na$^+$ ([M+Na])$^+$): 358.0533.

390.0797; calculated [C$_{15}$H$_{13}$NO$_8$]Na$^+$ MeOH ([M+Na+MeOH]$^+$): 390.0796.

693.1176; calculated [C$_{30}$H$_{26}$N$_2$O$_{16}$]$_2$Na$^+$ ([2M+Na])$^+$): 693.1175.

725.1435; calculated [C$_{30}$H$_{26}$N$_2$O$_{16}$]$_2$Na$^+$·MeOH ([2M+Na+MeOH]$^+$): 693.1175.

757.1693; calculated [C$_{30}$H$_{26}$N$_2$O$_{16}$]$_2$Na$^+$·2MeOH ([2M+Na+2MeOH]$^+$): 757.1699.

2-Acetyl-6-nitrobenzoic acid

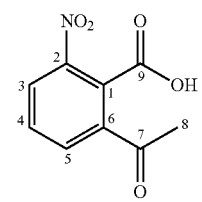

Hydrochloric acid (32% w/v; 351 mL), water (38 mL) and toluene (7.5 mL) were charged in a round bottom flask and diethyl 2-(4-nitro-3-oxo-3H-isobenzofuran-1-ylidene)malonate (147 g, 438 mmol) was added. The mixture was stirred and warmed to 95° C. over 2 h. At 70° C. evolution of carbon dioxide started. Stirring was continued for 20 h at 95° C., and the mixture then cooled to 10° C. The solid product was filtered off, washed with water and dried at 65° C. in vacuo. Yield: 84.5 g (404 mmol; 92%).

mp.: 169° C. (toluene)

$^1$H NMR (400 MHz, NaOD, 0.1M in deuterium oxide)

δ [ppm]=8.26 (dd, $^3J_{H,H}$=8.3, $^4J_{H,H}$=1.1 Hz, 1H, 3-CH), 8.17 (dd, $^3J_{H,H}$=7.8, $^4J_{H,H}$=1.1 Hz, 1H, 5-CH), 7.64 (dd, $^3J_{H,H}$=8.3, 7.8 Hz, 1H, 4-CH).

$^{13}$C NMR (101 MHz, NaOD, 0.1M in deuterium oxide)

δ [ppm]=202.5 (s, C-7), 173.0 (s, C-9), 145.3 (s, C-2), 135.9 (s, C-6), 135.0 (d, C-5), 134.5 (s, C-1), 128.6 (d, C-4), 127.9 (d, C-3), 27.9 (m, C-8).

MS (ESI$^+$): m/z=

232.0220; calculated [C$_{10}$H$_9$NO$_3$]Na$^+$ ([M+Na]$^+$): 232.0216.

245.0038; calculated [C$_{10}$H$_8$NNaO$_3$]2Na$^+$ ([M−H+ 2Na]$^+$): 254.0036.

2-amino-6-ethylbenzoic acid

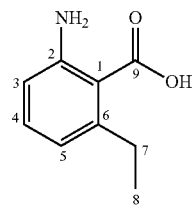

Sodium hydroxide (1M, 50 mL) and water (50 mL) were charged in a steel tube for high pressure hydrogenations and 2-acetyl-6-nitrobenzoic acid (10 g, 48 mmol) was added (resulting pH: 12.3). After adding Platinum(IV)oxide (200 mg) the reaction vessel was flushed with hydrogen three times and the mixture was stirred at 90° C. for 3 h at 20 bar (H$_2$). Then Raney-Nickel suspension (3.6 g) was added and after further stirring (3 h, 110° C., 20 bar H$_2$) the resulting mixture was filtrated through Celite®. The filtrate was adjusted to pH 3.5 with concentrated hydrochloric acid and extracted with ethyl acetate (3×200 mL). After removing the solvent and drying in vacuo a white solid was obtained. Yield: 6.1 g (37 mmol; 77%).

mp.: 105° C. (ethyl acetate)

$^1$H NMR (400 MHz, DMSO-d$_6$)

δ [ppm]=8.04 (s, 2H, NH$_2$), 7.02 (dd, $^3J_{H,H}$=8.2, 7.5 Hz, 1H, 4-CH), 6.59 (dd, $^3J_{H,H}$=8.2, $^4J_{H,H}$=1.2 Hz, 1H, 3-CH), 6.42 (dd, $^3J_{H,H}$=7.5 Hz, $^4J_{H,H}$=1.2 Hz, 1H, 5-CH), 2.71 (q, $^3J_{H,H}$=7.6 Hz, 2H, 7-CH), 1.12 (t, $^3J_{H,H}$=7.6 Hz, 3H, 8-CH).

$^{13}$C NMR (101 MHz, DMSO-d$_6$)

δ [ppm]=170.5 (s, C-9), 148.8 (s, C-2), 144.6 (s, C-6), 131.2 (d, C-4), 117.2 (d, C-5), 114.7 (s, C-1), 114.0 (d, C-3), 27.9 (t, C-7), 16.3 (q, C-8).

MS (ESI): m/z=

166.0864; calculated [C$_9$H$_{11}$NO$_2$]H$^+$ ([M+H]$^+$): 166.0864.

186.0689; calculated [C$_6$H$_{11}$NO$_2$]Na$^+$ ([M+Na]$^+$): 188.0682.

5-Ethyl-1H-benzo[d][1,3]oxazine-2,4-dione

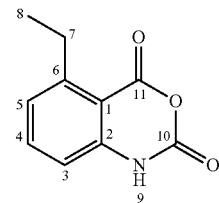

A solution of phosgene in toluene (20%, 14.7 mL, 28 mmol) was added dropwise to a slurry of 2-amino-6-ethylbenzoic acid (3.7 g, 22.4 mmol) in absolute THF (20 mL) keeping the temperature below 20° C. (ice cooling). After the mixture was stirred for 1h at room temperature, the reaction mixture was poured onto ice water (110 mL) and the resulting precipitate was collected, washed with water, and dried in vacuo to yield the isatoic anhydride: yield 3.73 g (87%).

mp.: 204° C. (H$_2$O).

$^1$H NMR (400 MHz, DMSO-d$_6$)

δ [ppm]=11.59 (s, 1H, 9-NH), 7.54 (dd, $^3J_{H,H}$=8.2, 7.6 Hz, 1H, 4-CH), 7.00 (dd, $^3J_{H,H}$=7.6 Hz, $^4J_{H,H}$=1.1 Hz, 1H, 5-CH), 6.95 (dd, $^3J_{H,H}$=8.2, $^4J_{H,H}$=1.2 Hz, 1H, 3-CH), 2.97 (q, $^3J_{H,H}$=7.4 Hz, 2H, 7-CH$_2$), 1.11 (t, $^3J_{H,H}$=7.4 Hz, 3H, 8-CH$_3$).

$^{13}$C NMR (101 MHz, DMSO-d$_6$)

δ [ppm]=158.5 (s, C-11), 148.5 (s, C-6), 147.1 (s, C-10), 142.7 (s, C-2), 136.1 (d, C-4), 124.5 (d, C-5), 113.5 (d, C-3), 107.8 (s, C-1), 27.1 (t, C-7), 15.0 (q, C-8).

MS (ESI$^+$): m/z=

192.0655; calculated [C$_{10}$H$_9$NO$_3$]H$^+$ ([M+H]$^+$): 192.0655.

214.0475; calculated [C$_{10}$H$_9$NO$_3$]Na$^+$ ([M+Na]$^+$): 214.0475.

405.1056; calculated [C$_{20}$H$_{18}$N$_2$O$_6$]$_2$Na$^+$ ([2M+Na]$^+$): 405.1057.

5-Ethyl-4-hydroxy-1-methyl-2-oxo-1,2-dihydroquinoline-3-carboxylic acid

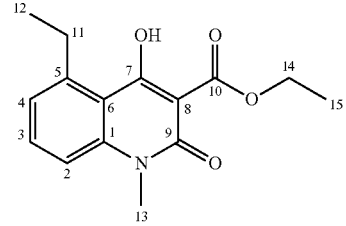

The isatoic anhydride (10 g, 52.3 mmol) was dissolved in DMF (100 mL) and cooled on an ice bath, and sodium hydride (95%, 1.58 g, 62.8 mmol) followed by methyl iodide (4.2 mL, 9.6 g, 68 mmol) was added at a rate to keep the temperature below 5° C. After stirring at room temperature overnight, excess methyl iodide was removed by evacuating for 30 min at approximately 30 mbar. Sodium hydride (95%, 1.58 g, 62.8 mmol) followed by diethylmalonate (9.5 mL, 10.06 g, 62.8 mmol) was added, and the mixture was heated at 85° C. for 2 h, then cooled, and quenched with water (500 mL). The aqueous solution was acidified with 1 M HCl, and the resulting precipitate was collected by filtration, washed with water, and dried to afford a light brown solid. Yield: 7.54 g (27.4 mmol; 52%).

mp.: 73° C. (H$_2$O).

$^1$H NMR (400 MHz, chloroform-d)

δ [ppm]=14.98 (s, 1H, 7-OH), 7.47 (dd, $^3J_{H,H}$=8.6, 7.5 Hz, 1H, 3-CH), 7.12 (dd, $^3J_{H,H}$=8.6 Hz, $^4J_{H,H}$=1.1 Hz, 1H, 2-CH), 6.98 (dd, $^3J_{H,H}$=7.5 Hz, $^4J_{H,H}$=1.1 Hz, 1H, 4-CH), 4.46 (q, $^3J_{H,H}$=7.1 Hz, 2H, 14-CH$_2$), 3.58 (s, 3H, 13-CH$_3$), 3.18 (q, $^3J_{H,H}$=7.4 Hz, 2H, 11-CH$_2$), 1.44 (t, $^3J_{H,H}$=7.1 Hz, 3H, 15-CH$_3$), 1.23 (t, $^3J_{H,H}$=7.4 Hz, 3H, 12-CH$_3$).

$^{13}$C NMR (101 MHz, chloroform-d)

δ [ppm]=174.5 (s, C-7), 173.5 (s, C-10), 159.2 (s, C-9), 147.0 (s, C-5), 142.9 (s, C-1), 133.6 (d, C-3), 124.7 (d, C-4), 113.3 (s, C-6), 112.6 (d, C-2), 97.5 (s, C-8), 62.3 (t, C-14), 30.3 (t, C-11), 29.9 (q, C-13), 16.4 (q, C-12), 14.2 (q, C-15).

MS (ESI$^+$): m/z=

276.1234; calculated [C$_{15}$H$_{17}$NO$_4$]H$^+$ ([M+H]$^+$): 276.1230.

298.1049; calculated [C$_{15}$H$_{17}$NO$_4$]Na$^+$ ([M+Na]$^+$): 298.1050.

573.2207; calculated [C$_{30}$H$_{34}$N$_2$O$_8$]$_2$Na$^+$ ([2M+Na]$^+$): 573.2207.

5-ethyl-4-hydroxy-1-methyl-2-oxo-1,2-dihydroquinoline-3-carboxylic acid

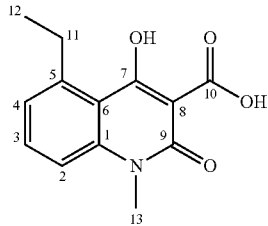

The ethyl ester (7.15 g, 26 mmol) was heated at 60° C. for six hours in a mixture of hydrochloric acid and acetic acid (80 mL, 2.8M HCl in AcOH). Afterwards, the reaction mixture was poured on iso-Propanol (200 mL). The formed precipitate washed with iso-Propanol (10 mL) and the product was obtained as a white solid. Yield: 3.18 g (12.9 mmol; 50%).

mp.: decomposition at 220° C. (iso-Propanol).

1H NMR (400 MHz, chloroform-d)

δ [ppm]=16.12 (s, 1H, OH), 15.60 (s, 1H, OH), 7.66 (dd, 3JH-H=8.6, 7.5 Hz, 1H, 3-CH), 7.33 (dd, 3JH-H=8.7 Hz, 4JH-H=1.1 Hz, 1H, 2-CH), 7.20 (dd, 3JH-H=7.5, 4JH-H=1.1 Hz, 1H, 4-CH), 3.72 (s, 3H, 13-CH3), 3.24 (q, 3JH-H=7.4 Hz, 2H, 11-CH2), 1.26 (t, 3JH-H=7.4 Hz, 3H, 12-CH3).

13C NMR (101 MHz, chloroform-d)

δ [ppm]=174.6 (s, C-10), 174.4 (s, C-7), 164.4 (s, C-9), 147.8 (s, C-5), 141.4 (s, C-1), 134.5 (d, C-3), 126.4 (d, C-4), 114.3 (s, C-6), 113.4 (d, C-2), 94.7 (s, C-8), 30.4 (q, C-13), 30.0 (t, C-11), 16.3 (q, C-12).

MS (ESI+): m/z=

248.0917; calculated [C13H13NO4]H+ ([M+H]+): 248.0917.

270.0735; calculated [C13H13NO4]Na+ ([M+Na]+): 270.0737.

517.1581; calculated [C26H26N2O8]2Na+ ([2M+Na]+): 517.1490.

N-(2-(2-(2-(2-azidoethoxy)ethoxy)ethoxy)ethyl)aniline

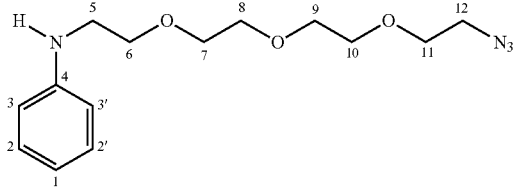

Subsequently the azido-PEG-bromide (7.34 g, 26 mmol) and aniline (4.75 mL, 52 mmol) were emulsified in water (30 mL) and heated to reflux overnight. After cooling to room temperature water (100 mL) was added and the aqueous emulsion was extracted with ethyl acetate (100 mL) four times. The organic phases were dried over magnesium sulphate and concentrated to dryness. The resulting oil was chromatographed on a silica gel column (cyclohexane/EtOAc 2/1 to 1/1) to give a yellow oil. Yield: 3.41 g (11.6 mmol, 45%).

$^1$H NMR (400 MHz, chloroform-d)

δ [ppm]=7.20-7.14 (m, 2H, 2-CH, 2'-CH), 6.73-6.68 (m, 1H, 1-CH), 6.64-6.60 (m, 2H, 3-CH, 3'-CH), 3.71-3.62 (m, 12H, 6-CH$_2$ bis 11-CH$_2$), 3.35 (t, $^3J_{H,H}$=5.1 Hz, 2H, 12-CH$_2$), 2.29 (t, $^3J_{H,H}$=5.1 Hz, 2H, 5-CH$_2$).

$^{13}$C NMR (101 MHz, chloroform-d)

δ [ppm]=148.2 (s, C-4), 129.1 (d, C-2, C-2'), 117.3 (d, C-1), 112.9 (d, C-3, C-3'), 70.6, 70.5, 70.5, 70.2, 69.9 (t, C-7 bis C-11), 69.5 (t, C-6), 50.5 (t, C-12), 43.4 (t, C-5).

MS (ESI$^+$): m/z=

295.1769; calculated [C$_{14}$H$_{22}$N$_4$O$_3$]H$^+$ ([M+H]$^+$): 295.1765.

317.1585; calculated [C$_{14}$H$_{22}$N$_4$O$_3$]Na$^+$ ([M+Na]$^+$): 317.1584.

N-(2-(2-(2-(2-azidoethoxy)ethoxy)ethoxy)ethyl)-5-ethyl-4-hydroxy-1-methyl-2-oxo-N-phenyl-1,2-dihydroquinoline-3-carboxamide

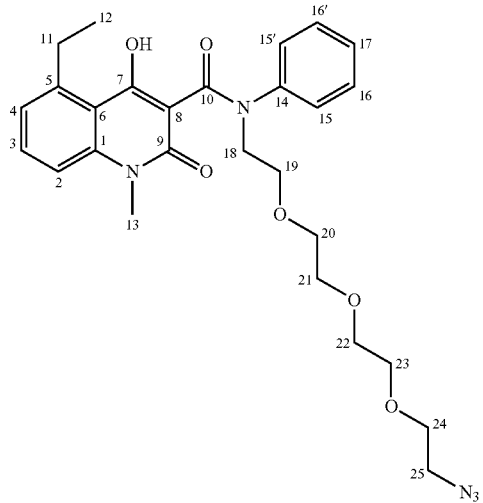 [SMILES: CCc1cccc2c1c(O)c(C(=O)N(CCOCCOCCOCCN=[N+]=[N-])c1ccccc1)c(=O)n2C]

The 1,2-dihydroquinoline-3-carboxylic acid (1 g, 4.05 mmol) was dissolved under argon atmosphere in dichloromethane (10 mL) and triethylamine (2.1 mL, 1.54 g, 15.2 mmol) and the N-PEG-aniline (1.43 g, 4.86 mmol) were added. At 0° C. (ice bath) thionyl chloride (0.38 mL, 0.63 g, 5.3 mmol), dissolved in dichloromethane (0.6 mL), was added dropwise within 30 minutes. The reaction mixture was stirred for 4 h at 0° C. and then overnight at room temperature. After removing the solvent in vacuo the resulting oil was chromatographed on a silica gel column (EtOAc/MeOH 9/1 to 6/1) to give a yellow sticky oil. Yield: 1.73 g (3.3 mmol, 82%).

$^1$H NMR (400 MHz, chloroform-d)

δ [ppm]=7.42-7.37 (m, 1H, 3-CH), 7.23-7.10 (m, 5H, 15-CH bis 17-CH), 7.03-7.00 (m, 1H, 2-CH), 7.00-6.96 (m, 1H, 4-CH), 3.71-3.58 (m, 12H, 19-CH$_2$ bis 24-CH$_2$), 3.62 (s, 3H, 13-CH$_3$), 3.36-3.32 (m, 2H, 25-CH$_2$), 3.29-3.24 (m, 2H, 18-CH$_2$), 3.20 (q, $^3J_{H,H}$=7.4 Hz, 2H, 11-CH$_2$), 1.25 (t, $^3J_{H,H}$=7.4 Hz, 3H, $^{12}$CH$_3$).

$^{13}$C NMR (101 MHz, chloroform-d)

δ [ppm]=174.5 (s, n.z.), 170.1 (s, n.z.), 167.7 (s, n.z.), 148.2 (s, C-14), 145.8 (s, C-5), 142.0 (s, C-1), 131.9 (d, C-3), 129.2, 128.5, 126.3 (d, 15-C bis 17-C), 124.4 (d, C-4), 113.6 (s, C-6), 112.4 (d, C-2), 103.9 (s, C-8), 70.6, 70.6, 70.4, 70.0, 69.6, 67.8 (t, 19-C bis 24-C), 50.6 (t, C-25), 43.5 (t, C-18), 30.0 (t, C-11), 29.6 (q, C-13), 16.7 (q, C-12).

MS (ESI$^+$): m/z=

524.2507; calculated [C$_{27}$H$_{33}$N$_5$O$_6$]H$^+$ ([M+H]$^+$): 524.2504.

546.2326; calculated [C$_{27}$H$_{33}$N$_5$O$_6$]Na$^+$ ([M+Na]$^+$): 546.2323.

N-(2-(2-(2-(2-aminoethoxy)ethoxy)ethoxy)ethyl)-5-ethyl-4-hydroxy-1-methyl-2-oxo-N-phenyl-1,2-dihydroquinoline-3-carboxamide

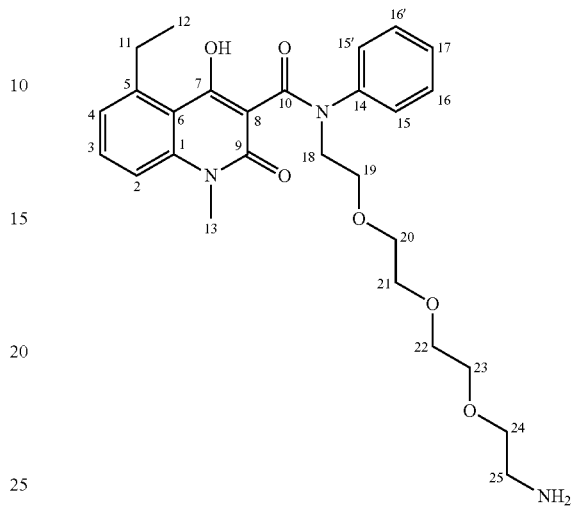

N-(2-{2-[2-(2-Azidoethoxy)ethoxy]ethoxy}ethyl)-5-ethyl-4-hydroxy-1-methyl-2-oxo-N-phenyl-1,2-dihydrochinolin-3-carboxamide (1.128 g, 2.15 mmol, 1.0 eq.) was dissolved under argon in tetrahydrofuran (15 mL) and a few mg of Pd/C were added. The argon atmosphere was changed to hydrogen (balloon) and the reaction mixture was stirred at room temperature for 16 h. After filtration on Celite® and evaporation of the solvent the desired product was obtained as a light brown solid.

yield: 840 mg (1.69 mmol, 79%).

mp.: 53° C. (THF)

$^1$H NMR (400 MHz, methanol-d$_4$)

δ [ppm]=7.42-7.39, 7.15-7.10 (m, 5H, 15-CH bis 17-CH), 7.26-7.21 (m, 1H, 3-CH), 7.10-7.05 (m, 1H, 2-CH), 6.82-6.79 (m, 1H, 4-CH), 3.91-3.86, 3.77-3.74, 3.68-3.52 (m, 12H, 19-CH$_2$ bis 24-CH$_2$), 3.52-3.46 (m, 2H, 11-CH$_2$), 3.40 (s, 3H, 13-CH$_3$), 3.29-3.22 (m, 2H, 18-CH$_2$), 3.21-3.18 (m, 2H, 25-CH$_2$), 1.14 (t, $^3J_{H,H}$=7.4 Hz, 3H, 12-CH$_3$).

$^{13}$CNMR (101 MHz, methanol-d$_4$)

δ [ppm]=174.5 (s, C-7), 174.2 (s, C-10), 162.8 (s, C-9), 147.2 (s, C-5), 143.0 (s, C-1), 142.8 (s, C-14), 130.4 (d, C-3), 129.2, 128.3, 128.2, (d, C-15 bis C-17), 124.4 (d, C-4), 121.7 (s, C-6), 113.5 (d, C-2), 109.2 (s, C-8), 71.3, 71.0, 71.0, 70.9, 70.7, 68.8, 68.1 (t, C-19 bis C-24), 44.7 (t, C-18), 40.7 (t, C-25), 30.3 (t, C-11), 29.8 (q, C-13), 17.8 (t, C-12).

MS (ESI$^+$): m/z=

498.2598; calculated [C$_{27}$H$_{35}$N$_3$O$_6$]H$^+$ ([M+H]$^+$): 498.2599.

520.2420; calculated [C$_{27}$H$_{35}$N$_3$O$_6$]Na$^+$ ([M+Na]$^+$): 520.2418.

995.5115; calculated [C$_{54}$H$_{70}$N$_6$O$_{12}$]$_2$H$^+$ ([2M+H]$^+$): 995.5124.

1017.4920; calculated [C$_{54}$H$_{70}$N$_6$O$_{12}$]$_2$Na$^+$ ([2M+Na]$^+$): 1017.4944.

3-ethyl-2((1E,3E,5E)-5-(3-(1-(5-ethyl-4-hydroxy-1-methyl-2-oxo-1,2-dihydroquinolin-3-yl)-1,15-dioxo-2-phenyl-5,8,11-trioxa-2,14-diazanonadecan-19-yl)-1,1-dimethyl-6,8-disulfonato-1H-benzo[e]indol-2(3H)-ylidene)penta-1,3-dien-1-yl)-1,1-dimethyl-1H-benzo[e]indol-3-ium-6,8-disulfonate (Cy5.5-CES271)

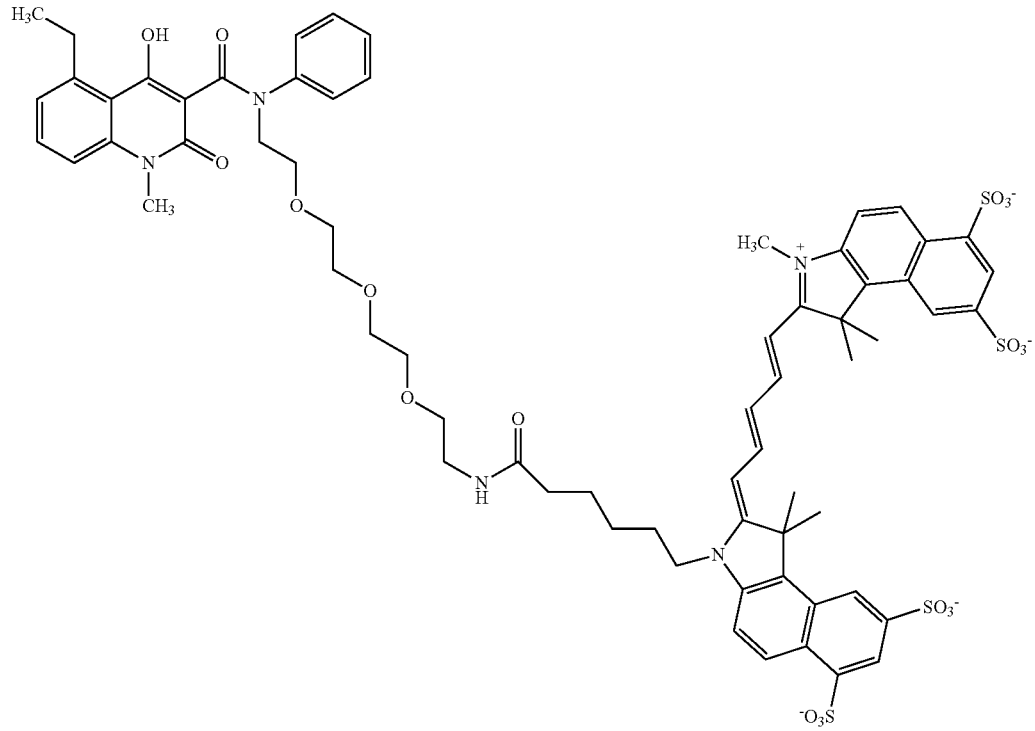

The amino-functionalized precursor (3.0 mg, 4.2 pmol) was dissolved in 400 µL dry dimethylformamide provided with 10 µL triethylamine. To this solution, Cy5.5-NHS ester (GE) (1 mg, 0.9 µmol) was added. The reaction mixture was vortexed for 16 h at room temperature in the dark. Purification of Cy5.5-CES271 was performed by gradient-HPLC using a Knauer system with two K-1800 pumps, an S-2500 UV detector and a RP-HPLC Nucleosil 100-5 C18 column (250 mm×4.6 mm). Eluent A: water (0.1% TFA). Eluent B: Acetonitrile (0.1% TFA). Gradient from 95% A to 40% A over 19 minutes, holding for 5 minutes and back to 95% in one minute at a flow rate of 5.5 ml/min, detection at λ=254 nm. The appropriate fractions ($t_R$=16.5 min) were collected, lyophilized, redissolved in 1 mL water and finally stored at −20° C. The average content of Cy5.5-CES271 was 0.45±0.02 µmol/ml (≈50%) as determined by fluorometer measurements with $\lambda_{abs}$=678 nm and $\varepsilon_{678}$=250000 $M^{-1}\ cm^{-1}$.

MS (ES⁻): m/e=464.1 (100%), 464.5, 464.8 $[M]^{3-}$; 696.7, 697.2, 697.7 $[M+H]^{2-}$.

Experimental Details for the Synthesis of fac-[$^{99m}$Tc(CO)₃(5-ethyl-4-hydroxy-1-methyl-N-{1-(1-methyl-1H-imidazol-2-yl)-2-[1-methyl-1H-imidazol-2-yl)methyl]-5,8,11-trioxa-2-azatridecan-13-yl}2-oxo-N-phenyl-1,2-dihydroquinoline-3-carboxamide)]⁺ ($^{99m}$Tc-FEB054)

2-{2-[2-(2-Azidoethoxy)ethoxy]ethoxy}-N,N-bis[(1-methyl-1H-imidazole-2-yl)methyl]ethylazide

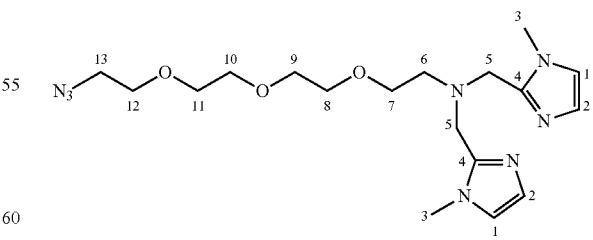

1-Methyl-1H-imidazole-2-carboxaldehyde (1.32 g, 12.0 mmol, 2.6 eq.) was added to a stirred solution of 2-{2-[2-(2-azidoethoxy)ethoxy]ethoxy}ethan-1-amine (1.00 g, 4.6 mmol, 1.0 eq.) in 1,2-dichloroethane (50 mL) under an Argon atmosphere and was heated for 30 minutes at 75° C.

Afterwards, the solution was cooled to 0° C., Sodium triacetoxyborohydride (3.22 g, 15.2 mmol, 3.3 eq.) was added, and the resulting mixture was allowed to stir at room temperature overnight. Upon completion, a saturated solution of NaHCO$_3$ (20 mL) was added and the reaction mixture extracted with ethyl acetate (2×50 mL). The combined organic layers were washed with brine, dried over MgSO$_4$ and concentrated under reduced pressure. The residue was purified by column chromatography over silica gel (ethyl acetate/methanol) to give the product as a yellow oil. Yield: 1.37 g (3.4 mmol, 74%).

$^1$H NMR (400 MHz, chloroform-d)

δ [ppm]=6.73 (d, $^3J_{H,H}$=1.3 Hz, 2H, 2-CH), 6.67 (d, $^3J_{H,H}$=1.3 Hz, 2H, 1-CH), 3.60 (s, 4H, 5-CH$_2$), 3.46-3.41 and 3.33-3.30 (m, 12H, 7-CH$_2$ to 12-CH$_2$), 3.32 (s, 6H, 3-CH$_3$), 3.18 (t, $^3J_{H,H}$=5.0 Hz, 2H, 13-CH$_2$), 2.60 (t, $^3J_{H,H}$=5.0 Hz, 2H, 6-CH$_2$).

$^{13}$C NMR (101 MHz, chloroform-d)

δ [ppm]=145.2 (s, C-4), 126.5 (s, C-2), 121.2 (s, C-1), 70.4, 70.3, 70.3, 69.8, 69.7, 69.7 (s, C-7 to C-12), 52.7 (s, C-6), 50.3 (s, C-13 and C-5), 32.1 (s, C-3).

MS (ESI$^+$): m/z=

407.2517; calculated for [C18H30N8O3]H+ ([M+H]+): 407.2514.

429.2331; calculated for [C18H30N8O3]Na+ ([M+Na]+): 429.2333.

2-{2-[2-(2-Azidoethoxy)ethoxy]ethoxyl}-N,N-bis[(1-methyl-1H-imidazole-2-yl)methyl]ethylamine

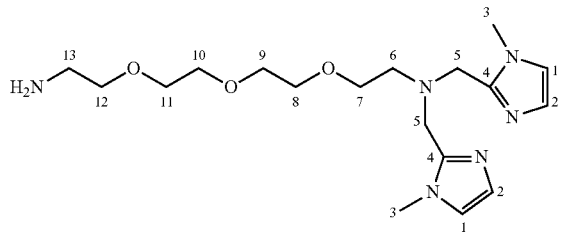 [SMILES: Cn1ccnc1CN(CCOCCOCCOCCN)Cc1nccn1C]

2-{2-[2-(2-Azidoethoxy)ethoxy]ethoxyl}-N,N-bis[(1-methyl-1H-imidazole-2-yl)methyl]ethylazide (1.12 g, 2.8 mmol, 1.0 eq.) was dissolved in tetrahydrofuran (10 mL), was treated with palladium on activated charcoal and stirred under a hydrogen atmosphere over night at room temperature. The reaction mixture was filtered over Celite® and concentrated under reduced pressure to give the product as a yellow oil. Yield: 1.02 g (2.7 mmol, 96%).

$^1$H NMR (400 MHz, chloroform-d)

δ [ppm]=6.81 (d, $^3J_{H,H}$=1.2 Hz, 2H, 2-CH), 6.73 (d, $^3J_{H,H}$=1.3 Hz, 2H, 1-CH), 3.68 (s, 4H, 5-CH$_2$), 3.53-3.48 and 3.43-3.38 (m, 12H, 7-CH$_2$ to 12-CH$_2$), 3.40 (s, 6H, 3-CH$_3$), 2.77 (t, $^3J_{H,H}$=5.2 Hz, 2H, 13-CH$_2$), 2.70 (t, $^3J_{H,H}$=5.2 Hz, 2H, 6-CH$_2$).

$^{13}$C NMR (101 MHz, chloroform-d)

δ [ppm]=145.5 (s, C-4), 127.0 (s, C-2), 121.4 (s, C-1), 72.8, 70.5, 70.4, 70.2, 69.9, 69.9 (s, C-7 bis C-12), 52.9 (s, C-6), 50.5 (s, C-5), 41.4 (s, C-13), 32.3 (s, C-3).

MS (ESI$^+$): m/z=

381.2607; calculated for [C18H32N6O3]H+ ([M+H]+): 381.2609.

403.2425; calculated for [C18H32N6O3]Na+ ([M+Na]+): 403.2428.

N-{1-(1-methyl-1H-imidazol-2-yl)-2-[(1-methyl-1H-imidazol-2-yl)methyl]-5,8,11-trioxa-2-azatridecan-13-yl}aniline

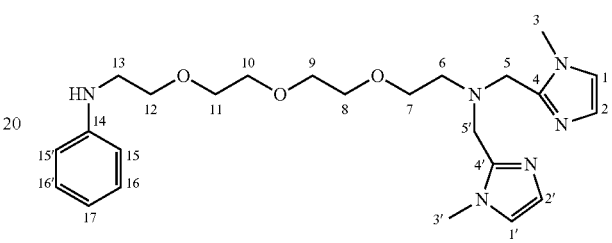

2-{2-[2-(2-Azidoethoxy)ethoxy]ethoxy}-N,N-bis[(1-methyl-1H-imidazole-2-yl)methyl]ethylamine (139 mg, 0.37 mmol, 1.2 eq.) was dissolved in 2-propanol (5 mL), followed by the addition of copper(I) iodide (6 mg, 0.03 mmol, 0.1 eq.), K$_3$PO$_4$ (132 mg, 0.62 mmol, 2.0 eq.), ethylene glycol (35 µL, 0.62 mmol, 2.0 eq.) and Iodobenzene (35 µL, 0.31 mmol, 1.0 eq.). The reaction vessel was flushed with argon and stirred at 80° C. for 23 hours. Water (10 mL) was added, the reaction mixture extracted with ethyl acetate (2×15 mL) and the solvent of the combined organic phases removed under reduced pressure. The crude product was purified by column chromatography over silica gel (chloroform/methanol) to give the product as a yellow oil. Yield: 84 mg (0.18 mmol, 58%).

$^1$H NMR (400 MHz, methanol-d$_4$)

δ [ppm]=7.10 d (d, $^3J_{H,H}$=8.7 Hz, 7.3 Hz, 2H, 16-CH, 16'-CH), 6.98 (d, $^3J_{H,H}$=1.3 Hz, 2H, 2-CH, 2'-CH), 6.83 (d, $^3J_{H,H}$=1.3 Hz, 2H, 1-CH, 1'-CH), 6.66-6.60 (m, 3H, 17-CH, 15-CH, 15'-CH), 3.71 (s, 4H, 5-CH$_2$, 5'-CH$_2$), 3.64-3.55 and 3.46-3.40 (m, 12H, 7-CH$_2$ to 12-CH$_2$), 3.51 (s, 6H, 3-CH$_3$, 3'-CH$_3$), 3.22 (t, $^3J_{H,H}$=5.5 Hz, 2H, 13-CH$_2$), 2.66 (t, $^3J_{H,H}$=5.3 Hz, 2H, 6-CH$_2$).

$^{13}$C NMR (101 MHz, chloroform-d)

δ [ppm]=150.0 (s, C-14), 146.4 (s, C-4, C-4'), 130.1 (d, C-16, C-16'), 126.9 (d, C-1, C-1'), 123.4 (d, C-2, C-2'), 118.3 (d, C-17), 114.2 (d, C-15, C-15'), 71.6, 71.6, 71.4, 71.1, 70.7, 70.6 (t, C-7 bis C-12), 54.2 (t, C-6), 51.6 (t, C-5), 44.7 (t, c-13), 33.1 (q, C-3, C-3').

MS (ESI$^+$): m/z=

457.2921; calculated for [C$_{24}$H$_{36}$N$_6$O$_3$]H$^+$ ([M+H]$^+$): 457.2933.

479.2743; calculated for [C$_{24}$H$_{36}$N$_6$O$_3$]Na$^+$ ([M+Na]$^+$): 479.2752.

5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-1-2-oxo-N-phenyl-1,2-dihydroquinoline-3-carboxamide

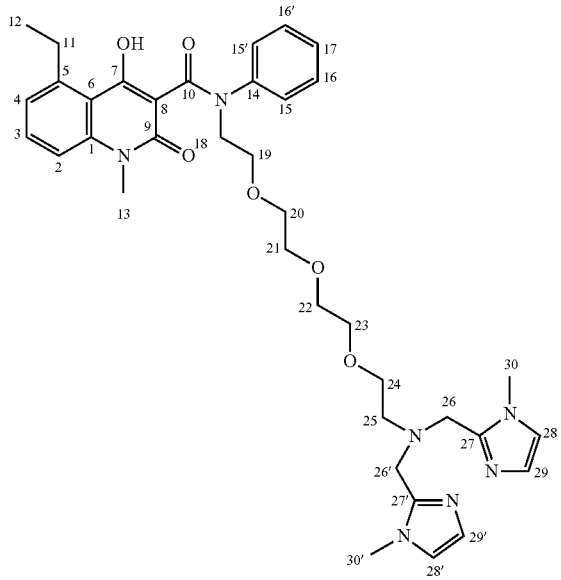 [SMILES: CCc1cccc2c1c(O)c(C(=O)N(CCOCCOCCOCCN(Cc1nccn1C)Cc1nccn1C)c1ccccc1)c(=O)n2C]

5-ethyl-4-hydroxy-1-methyl-2-oxo-1,2-dihydroquinoline-3-carboxylic acid (319 mg, 1.29 mmol, 1.0 eq.) was dissolved in tetrahydrofuran (5 mL), cooled to 0° C. under an argon atmosphere and triethylamine (679 μL, 4.90 mmol, 3.8 eq.) was added dropwise. The resulting solution was treated with N-{1-(1-methyl-1H-imidazol-2-yl)-2-[(1-methyl-1H-imidazol-2-yl)methyl]-5,8,11-trioxa-2-azatridecan-13-yl}aniline (578 mg, 1.29 mmol, 1.0 eq.) in tetrahydrofuran (2 mL) followed by the drop wise addition of thionyl chloride (112 μL, 1.55 mmol, 1.2 eq.) in tetrahydrofuran (488 μL) over 15 minutes at 0° C. After 20 h at room temperature the reaction mixture was washed with saturated NaHCO$_3$ solution, extracted with chloroform (2×10 mL) and the solvent of the combined organic layers was removed under reduced pressure. After column chromatography over silica gel (ethyl acetate/methanol), the product was obtained as a brown solid. Yield: 600 mg (0.88 mmol, 68%).

mp.: 73° C. (methanol).

$^1$H NMR (400 MHz, acetone-d$_6$)

δ [ppm]=7.42 (t, $^3J_{H,H}$=8.0 Hz, 1H, 3-CH), 7.38-7.34 and 7.21-7.09 (m, 5H, 15CH to 17-CH), 7.21-7.26 (m, 1H, 2-CH), 7.01 (d, $^3J_{H,H}$=1.3 Hz, 2H, 29-CH, 29'-CH), 7.01-6.96 (m, 1H, 4-CH), 6.87 (d, $^3J_{H,H}$=1.3 Hz, 2H, 28-CH, 28'-CH), 3.83 (s, 4H, 26-CH$_2$), 3.57 (s, 3H, 30-CH$_3$), 3.56-3.41 (m, 14H, 18-CH$_2$ to 24-CH$_2$), 3.37 (s, 3H, 13-CH$_3$), 3.26 (q, $^3J_{H,H}$=7.2 Hz, 2H, 11-CH$_2$), 2.74 (t, $^3J_{H,H}$=5.2 Hz, 2H, 25-CH$_2$), 1.22 (t, $^3J_{H,H}$=7.2 Hz, 1H, 12-CH$_3$).

$^{13}$C NMR (101 MHz, acetone-d$_6$)

δ [ppm]=174.2 (NA), 168.9 (NA), 159.7 (NA), 146.2 (s, C-27, C-27'), 145.8 (s, C-5), 144.0 (s, C-14), 142.7 (s, C-1), 131.9 (d, C-3), 129.0, 128.0, 127.6 (d, C-15 to 17C), 127.0 (d, C-28, C-28'), 125.1 (d, C-4), 122.5 (d, C-29, C-29'), 115.2 (s, C-8), 113.5 (d, C-2), 71.3, 71.2, 71.2, 70.9, 70.7, 70.6, 68.8 (t, C-18 to C-24), 53.6 (t, C-25), 51.4 (t, C-26), 32.8 (q, C-30), 30.7 (t, C-11), 29.5 (q, C-13), 17.6 (t, C-12).

C-6 could not be identified.

MS (ESI$^+$): m/z=

686.3660; calculated for [C$_{37}$H$_{47}$N$_7$O$_6$]H$^+$ ([M+H]$^+$): 686.3661.

708.3480; calculated for [C$_{37}$H$_{47}$N$_7$O$_6$]Na$^+$ ([M+Na]$^+$): 708.3480.

747.2795; calculated for [C$_{37}$H$_{46}$N$_7$O$_6$]Na$^+$ ([M+Cu−H]$^+$): 747.2800.

fac-[Re(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$

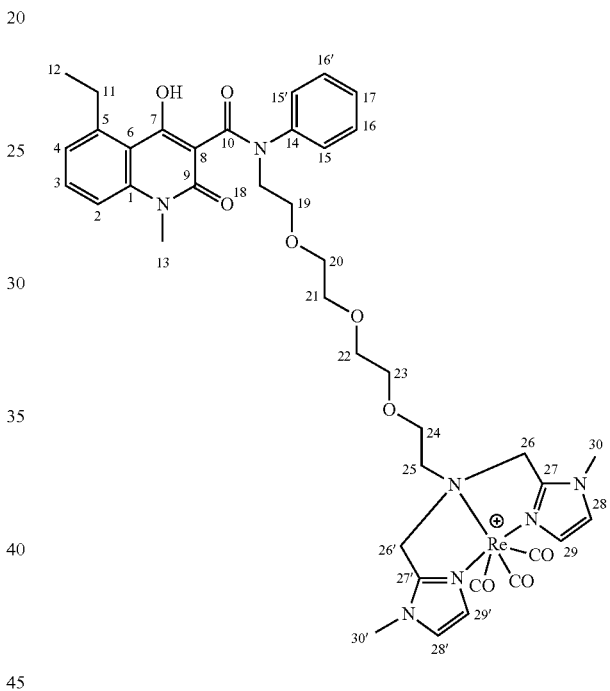

[ReBr$_3$(CO)$_3$][NEt$_4$]$_2$ (56 mg, 0.07 mmol, 1.0 eq.) was dissolved in Water (1 mL), added to a solution of 5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide (50 mg, 0.07 mmol, 1 eq.) in methanol (4 mL) and stirred over night at room temperature. The solvent was removed under reduced pressure and the product purified by column chromatography over C-18 reversed phase silica gel (water/methanol) to give a brown solid. Yield: 41 mg (0.04 mmol, 60%).

mp.: 115 (methanol)

MS (ESI$^+$): m/z=

956.2972; calculated for [C$_{40}$H$_{47}$N$_7$O$_9$Re]$^+$ ([M]$^+$): 956.2989.

HPLC: (Nucleosil 100-5 C18 (4×250 mm))

t$_{Ret}$: 17.65 min fac-[$^{99m}$Tc(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ ([$^{99m}$Tc]FEB054)

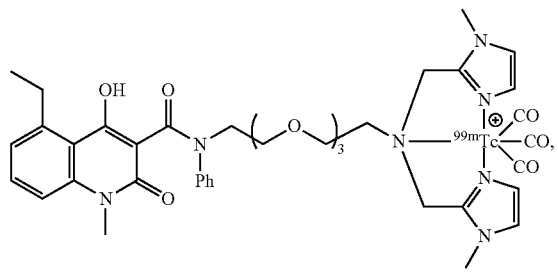

To a mixture of K$_2$[H$_3$BCO$_2$] (4.5 mg, 33 µmol), KNa-tartrate*4H$_2$O (7 mg, 25 µmol) and Na$_2$B$_4$O$_7$*10 H$_2$O (7 mg, 18 µmol) under argon atmosphere was added freshly eluated $^{99m}$TcO$_4$ (3950 MBq) in isotonic NaCl solution (1 mL). The reaction mixture was heated 20 minutes at 110° C. yielding fac-[$^{99m}$Tc(CO)$_3$(OH$_2$)$_3$]$^+$. Then 5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide (1 mg, 1.4 µmol) in isotonic NaCl solution (200 µL) was added and the mixture heated for 15 minutes at 50° C. Purification of fac-[$^{99m}$Tc(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ was performed by gradient-HPLC using a Knauer system with a K-500 pump, a K-501 pump, a K-2000 UV detector, a NaI(Tl) Scintibloc 51 SP51 γ-detector and a reversed phase C$_{18}$ column (ACE-126-2510, 10 mm×250 mm). Eluent A: water (0.1% TFA). Eluent B: methanol (0.1% TFA). Gradient from 70% A to 0% A over 30 minutes, holding for 8 minutes and back to 70% A over 5 minutes at a flow rate of 5.5 ml min$^{-1}$, detection at λ=254 nm. After collection of the product fraction, the solvent was removed under reduced pressure. The resulting residue was resolved in ethanol (10 µL) and a solution of Tween® 80 (190 µL, 1.6% in isotonic NaCl solution). Quality control of the solution was performed with co injection of the faci-[Re(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-3-yl}-2-oxo-N-phenyl-1,2-dihydroquinoline-3-carboxamide)]$^+$ (0.1 mg, 0.1 µmol) in methanol (15 µL) by gradient-HPLC using a Knauer system with two Smartline 1000 pumps, Smartline UV detector 2500 (Herbert Knauer GmbH), a GabiStar γ-detector (Raytest Isotopenmessgerate GmbH) and a reversed phase C$_{18}$ column (Nucleosil 100-5 C-18 column 4.6 mm×250 mm). Eluent A: water (0.1% TFA). Eluent B: methanol (0.1% TFA). Gradient from 70% A to 0% A over 15 minutes, holding for minutes and back to 70% A over 5 minutes at a flow rate of 5.5 ml min$^{-1}$, detection at λ=254 nm.

Experimental Details for the Synthesis of fac-[$^{99m}$Tc(bathophenanthrolinedisulfonic acid)(CO)$_3$(5-ethyl-4-hydroxy-1-methyl-2-oxo-N-phenyl-N-[1-(pyridin-3-yl)-2,5,8,11-tetraoxatridecan-13-yl]1,2-dihydroquinoline-3-carboxamide)]$^{99m}$Tc-FEB105)

3-(13-azido-2,5,8,11-tetraoxatridecyl)pyridine

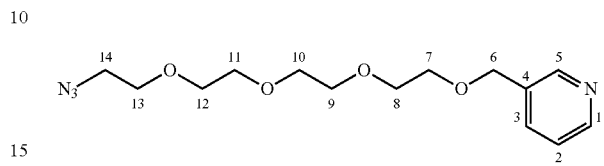

Under an argon atmosphere, 2-{2-[2-(2-azidoethoxy)ethoxy]ethoxy}ethan-1-ol (4.47 g, 20.4 mmol, 1.2 eq) was dissolved in DMF (80 mL), cooled to 0° C. and stepwise treated with NaH (95%, 945 mg, 37.4 mmol, 2.2 eq.). After 30 minutes a solution of 3-(bromomethyl)pyridine hydrobromide (4.30 g, 17.0 mmol, 1.0 eq.) in DMF (60 mL) was added dropwise at 0° C. After three hours, the solvent was removed under reduced pressure, the residue redissolved in water (50 mL) and extracted with DCM (3×50 mL). The combined organic layers were washed with brine, dried over MgSO$_4$ and concentrated under reduced pressure. The residue was purified by column chromatography over silica gel (chloroform/methanol) to give the product as a yellow oil. Yield: 2.94 g (9.4 mmol, 55%).

$^1$H NMR (400 MHz, methanol-d$_4$)

δ [ppm]=8.56-8.53 (m, 1H, 5-CH), 8.48-8.45 (m, 1H, 1-CH), 7.88-7.84 (m, 1H, 3-CH), 7.45-7.41 (m, 1H, 2-CH), 4.62 (s, 2H, 6-CH2), 3.70-3.62 (m, 14H, 7-CH2 to 13-CH2), 3.35 (t, 3JH,H=5.0 Hz, 2H, 14-CH2).

$^{13}$C NMR (101 MHz, methanol-d$_4$)

δ [ppm]=149.4 (d, C-5), 149.2 (d, C-1), 137.7 (d, C-3), 136.3 (s, C-4), 125.1 (d, C-2), 71.6, 71.6, 71.6, 71.6, 71.5, 71.1, 71.1 (t, C-7 to C-12), 71.3 (t, C-6), 51.8 (t, C-14).

MS (ESI$^+$): m/z=

311.1712; calculated for [C$_{14}$H$_{22}$N$_4$O$_4$]H$^+$ ([M+H]$^+$): 311.1714.

333.1532; calculated for [C$_{14}$H$_{22}$N$_4$O$_4$]Na$^+$ ([M+Na]$^+$): 333.1533.

1-(pyridin-3-yl)-2,5,8,11-tetraoxatridecan-13-amine

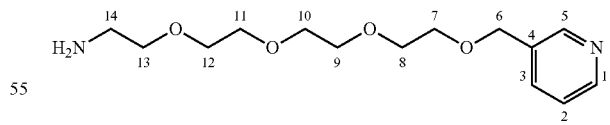

3-(13-azido-2,5,8,11-tetraoxatridecyl)pyridine (1.23 g, 4.15 mmol, 1.0 eq.) was dissolved in THF (20 mL) and PPh$_3$ (3.27 g, 12.45 mmol, 3.0 eq) was added. After gas evolution stopped, H$_2$O (5 mL) was added and the reaction mixture stirred at 40° C. for 16 hours. Afterwards, the solvent was removed under reduced pressure and the residue was purified by column chromatography over silica gel (ethyl acetate/methanol) to give the product as a yellow oil. Yield: 845 mg (3.0 mmol, 71%).

¹H NMR (400 MHz, methanol-d₄)

δ [ppm]=8.55-8.53 (m, 1H, 5-CH), 8.48-8.45 (m, 1H, 1-CH), 7.88-7.84 (m, 1H, 3-CH), 7.45-7.41 (m, 1H, 2-CH), 4.62 (s, 2H, 6-CH₂), 3.70-3.59 (m, 12H, 7-CH₂ to 12-CH₂), 3.50 (t, $^3J_{H,H}$=5.3 Hz, 2H, 13-CH), 2.75 (t, $^3J_{H,H}$=5.3 Hz, 2H, 14-CH₂).

¹³C NMR (101 MHz, methanol-d₄)

γ [ppm]=149.4 (d, C-5), 149.3 (d, C-1), 137.7 (d, C-3), 136.3 (s, C-4), 125.1 (d, C-2), 73.5 (t, C-13), 71.6, 71.6, 71.6, 71.3, 71.3, 71.1 (t, C-7 to C-12), 71.3 (t, C-6), 42.1 (t, C-14).

MS (ESI⁺): m/z=

285.1808; calculated for [C₁₄H₂₂N₂O₄]H⁺ ([M+H]⁺): 285.1809.

307.1628; calculated for [C₁₄H₂₂N₂O₄]Na⁺ ([M+Na]⁺): 307.1628.

N-phenyl-1-(pyridin-3-yl)-2,5,8,11-tetraoxatridecan-13-amine

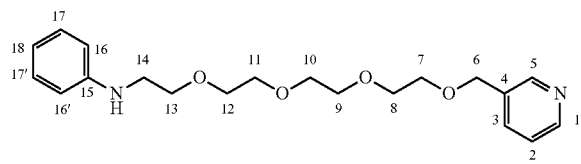

To a solution of 1-(pyridin-3-yl)-2,5,8,11-tetraoxatridecan-13-amine (400 mg, 1.41 mmol, 1.1 eq.) in i-propanol (10 mL), iodobenzene (143 μL, 1.28 mmol, 1.0 eq.), CuI (48 mg, 0.26 mmol, 0.2 eq.), K₃PO₄ (543 mg, 2.56 mmol, 2.0 eq.) and ethylene glycol (143 μml, 2.56 mmol, 2.0 eq.) were added and the reaction mixture was stirred at 80° C. for 40 hours. Afterwards, the reaction mixture was filtered over Celite®, the solvent was removed under reduced pressure and the residue was purified by column chromatography over silica gel (cyclohexane/ethyl acetate) to give the product as a yellow oil. Yield: 155 mg (0.43 mmol, 34%).

¹H NMR (400 MHz, chloroform-d)

δ [ppm]=8.58-8.55 (m, 1H, 5-CH), 8.53-8.50 (m, 1H, 1-CH), 7.69-7.65 (m, 1H, 3-CH), 7.27-7.23 (m, 1H, 2-CH), 7.16-7.12 (m, 2H, 17-CH, 17'-CH), 6.70-6.65 (m, 1H, 18-CH), 6.62-6.59 (m, 2H, 16-CH, 16'-CH), 4.56 (s, 2H, 6-CH₂), 3.68-3.63 (m, 14H, 7-CH₂ to 13-CH₂), 3.27 (t, $^3J_{H,H}$=5.3 Hz, 2H, 14-CH).

¹³C NMR (101 MHz, chloroform-d)

δ [ppm]=149.2 (d, C-5), 149.1 (d, C-1), 148.3 (s, C-15), 135.5 (d, C-3), 133.8 (s, C-4), 129.2 (d, C-17, C-17'), 123.5 (d, C-2), 117.5 (d, C-18), 113.1 (s, C-16, C-16'), 70.8 (t, C-6), 70.8, 70.7, 70.7, 70.6, 70.4, 69.9, 69.7, 69.7 (t, C-7 to C-13), 43.6 (t, C-14).

MS (ESI⁺): m/z=

361.2120; calculated for [C₂₀H₂₈N₂O₄]H⁺ ([M+H]⁺): 361.2122.

383.1936; calculated for [C₂₀H₂₈N₂O₄]Na⁺ ([M+Na]⁺): 383.1941.

5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide

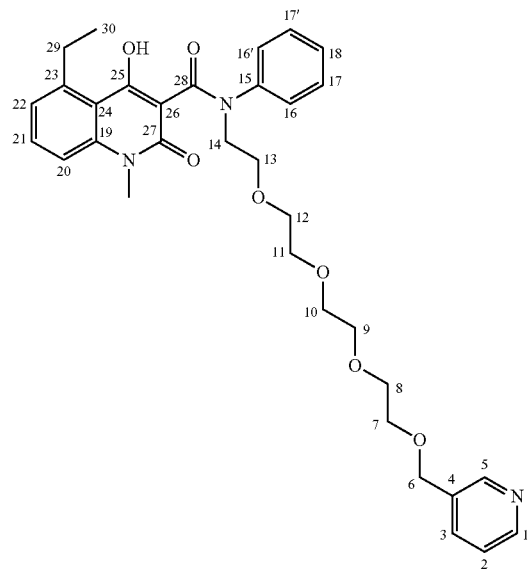 [SMILES: CCc1cccc2c1c(O)c(C(=O)N(CCOCCOCCOCCOCc1cccnc1)c1ccccc1)c(=O)n2C]

5-ethyl-4-hydroxy-1-methyl-2-oxo-1,2-dihydroquinoline-3-carboxylic acid (81 mg, 0.33 mmol, 1.0 eq.) was dissolved in tetrahydrofuran (4 mL), cooled to 0° C. under an argon atmosphere and triethylamine (173 μL, 1.25 mmol, 3.8 eq.) was added dropwise. The resulting solution was treated with N-phenyl-1-(pyridin-3-yl)-2,5,8,11-tetraoxatridecan-13-amine (118 mg, 0.33 mmol, 1.0 eq.) in tetrahydrofuran (2 mL) followed by the dropwise addition of thionyl chloride (29 μL, 0.40 mmol, 1.2 eq.) in tetrahydrofuran (471 μL) over 15 minutes at 0° C. After 20 h at room temperature the reaction mixture was washed with saturated NaHCO₃ solution, extracted with chloroform (2×10 mL) and the solvent of the combined organic layers was removed under reduced pressure. After column chromatography over silica gel (ethyl acetate/methanol), the product was obtained as a brown solid. Yield: 40 mg (0.07 mmol, 21%).

¹H NMR (600 MHz, methanol-d₄)

δ [ppm]=8.52-8.50 (m, 1H, 5-CH), 8.44-8.41 (m, 1H, 1-CH), 7.83-7.81 (m, 1H, 3-CH), 7.44-7.40, 7.25-7.22 and 7.02-6.99 (m, 3H, 24-CH to 26-CH), 7.35-7.31 and 7.21-7.11 (m, 5H, 16-CH to 18-CH), 4.58 (s, 2H, 6-CH₂), 3.69-3.59 (m, 14H, 7-CH₂ to 13-CH₂), 3.48-3.45 (m, 3H, 29-CH₃), 3.25-3.22 (m, 2H, 14-CH₂), 3.20-3.15 (m, 2H, 30-CH₂), 1.19-1.15 (m, 3H, ³¹-CH₃).

¹³C NMR (151 MHz, methanol-d₄)

δ [ppm]=147.9 (d, C-5), 147.9 (d, C-1), 136.2 (d, C-3), 131.0, 124.8 and 112.5 (d, C-24 to C-26), 128.2, 127.5, 126.8 (d, C-16 to C-18), 123.7 (d, C-2), 145.0 (s, C-23), 141.1 (s, C-27), 134.8 (s, C-4), 125.2 (s, C-22), 112.9 (s, C-20), 69.7 (t, C-6), 70.2, 70.1, 70.1, 70.0, 69.9, 69.7, 67.4 (t, C-7 to C-13), 43.3 (t, C-14), 29.8 (C-30), 28.9 (q, C-29), 16.1 (q, C-31).

MS (ESI⁺): m/z=

590.2854; calculated for [C₃₃H₃₉N₃O₇]H⁺ ([M+H]⁺): 590.2861.

612.2670; calculated for [C₂₀H₂₈N₂O₄]Na⁺ ([M+Na]⁺): 612.2680.

ACE-126-2510, 10 mm×250 mm

HPLC: (ACE-126-2510, (10 mm×250 mm)), Eluent A: water (0.1% TFA). Eluent B: methanol (0.1% TFA). Gradient from 70% A to 0% A over 30 minutes, holding for 8 minutes and back to 70% A over 5 minutes at a flow rate of 5.5 ml min⁻¹, detection at λ=254 nm.

$t_{Ret}$: 23.68 min fac-[$^{99m}$Tc(bathophenanthrolinedisulfonic acid)(CO)$_3$(5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide)]$^-$ ($^{99m}$Tc-FEB105)

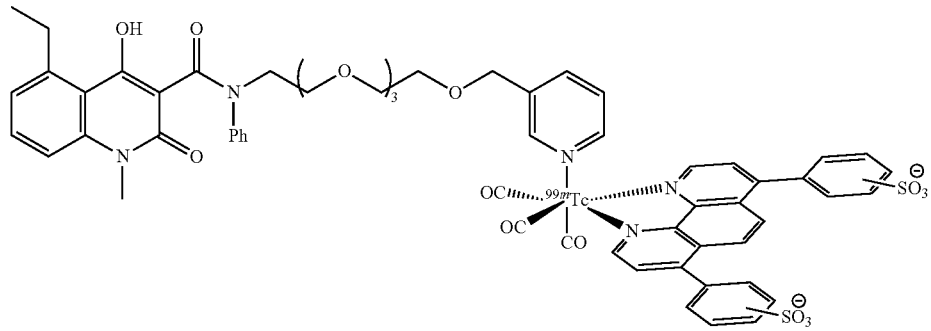

To a mixture of K$_2$[H$_3$BCO$_2$] (4.5 mg, 33 μmol), KNa-tartrate*4H$_2$O (7 mg, 25 μmol) and Na$_2$B$_4$O$_7$*10 H$_2$O (7 mg, 18 μmol) under argon atmosphere was added freshly eluated $^{99m}$TcO$_4$ in isotonic NaCl solution (1 mL). The reaction mixture was heated 20 minutes at 110° C. yielding fac-[$^{99m}$Tc(CO)$_3$(OH$_2$)$_3$]$^+$. Then 5-ethyl-4-hydroxy-1-methyl-2-oxo-N-phenyl-N-[1-(pyridin-3-yl)-2,5,8,11-tetraoxatridecan-13-yl]-1,2-dihydroquinoline-3-carboxamide (0.5 mg, 0.8 μmol) in isotonic NaCl solution (150 μL) and bathophenanthrolinedisulfonic acid disodium salt hydrate (0.7 mg, 1.3 μmol) in isotonic NaCl solution (150 μL) were added and the mixture heated for 15 minutes at 50° C. Analysis was performed by gradient-HPLC using a Knauer system with two Smartline 1000 pumps, Smartline UV detector 2500 (Herbert Knauer GmbH), a GabiStar γ-detector (Raytest Isotopenmessgeräte GmbH) and a reversed phase C$_{18}$ column (Nucleosil 100-5 C-18 column 4.6 mm×250 mm). Eluent A: water (0.1% TFA). Eluent B: methanol (0.1% TFA). Gradient from 70% A to 0% A over 25 minutes, holding for 5 minutes and back to 70% A over 5 minutes at a flow rate of 1 ml min$^{-1}$, detection at λ=254 nm.

Experimental Details for the Synthesis of 1-[4-(5-ethyl-4-hydroxy-N,1-dimethyl-2-oxo-1,2-dihydroquinoline-3-carboxamido)phenyl]-fluoro-1-oxobutane-2-sulfonic acid Methyl 4-[(tert-butoxycarbonyl)(methyl)amino]benzoate

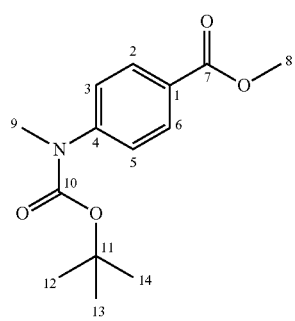

Methyl 4-(methylamino)benzoate (1.0 g, 6.1 mmol, 1.0 eq.) was dissolved in THF (40 mL). Then NEt$_3$ (3.9 mL, 18.2 mmol, 3.0 eq.) and di-tert-butyl dicarbonate (1.2 mL, 9.1 mmol, 1.5 eq.) were added and the reaction mixture was refluxed for 16 hours. The solvent was removed under reduced pressure and the residue was purified by column chromatography over silica gel (cyclohexane/ethyl acetate) to give the product as a colorless oil. Yield: 780 mg (2.9 mmol, 49%).

$^1$H NMR (400 MHz, chloroform-d)

δ [ppm]=7.99 (m, 2H, 2-CH/6-CH), 7.32 (m, 2H, 3-CH/5-CH), 3.90 (s, 3H, 8-CH3), 3.29 (s, 3H, 9-CH3), 1.46 (s, 9H, 12-CH3 to 14-CH3).

$^{13}$C NMR (101 MHz, chloroform-d)

δ [ppm]=166.8 (C-7), 154.3 (C-10), 148.1 (C-4), 130.1 (C-2/C-6), 126.4 (C-1), 124.5 (C-3/C-5), 81.2 (C-11), 52.2 (C-8), 37.0 (C-9), 28.4 (C-12 to C-14).

MS (ESI$^+$): m/z=

288.1214; calculated for [C$_{14}$H$_{19}$NO$_4$]Na$^+$ ([M+Na]$^+$): 288.1206.

tert-Butyl [4-(2,2-dioxido-1,2-oxathiolane-3-carbonyl)phenyl](methyl)carbamate

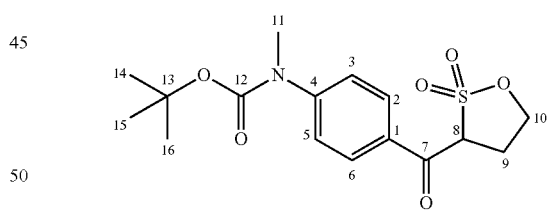

In a flame dried schlenk flask under argon atmosphere, 1,3-propane sultone (123 mg, 1.01 mmol, 1.35 eq.) was dissolved in dry THF (15 mL) and cooled to −78° C. Over 30 minutes, n-buthyl lithium (0.63 mL, 1.6 M in hexane, 1.01 mmol, 1.35 eq.) was added dropwise. After 1 hour, methyl 4-[(tert-butoxycarbonyl)(methyl)amino]benzoate (200 mg, 0.754 mmol, 1.0 eq.) in THF (10 mL) was added dropwise at −78° C. After two hours at −78° C., acetic acid (500 μL) was added and the reaction mixture was allowed to warm to room temperature. The reaction mixture was washed with water (50 mL) and extracted with dichloromethane (3×100 mL). The combined organic fractions were dried over MgSO$_4$, the solvent was removed under reduced pressure and the residue was purified by column chromatography over silica gel (cyclohexane/ethyl acetate) to give the product as a colorless oil. Yield: 110 mg (0.31 mmol, 41%).

$^1$H NMR (400 MHz, chloroform-d)

δ [ppm]=8.05 (m, 2H, 2-CH/6-CH), 7.47 (m, 2H, 3-CH/5-CH), 5.08 (dd, $^3J_{H,H}$=8.9, 5.7 Hz, 1H, 8-CH), 4.65 (ddd, $^3J_{H,H}$=8.9, 7.4, 6.1 Hz, 1H, 10-CHa), 4.55 (ddd, $^3J_{H,H}$=8.9, 7.4, 6.1 Hz, 1H, 10-CHb), 3.33 (s, 3H, 11-CH3), 3.30 (dddd, $^3J_{H,H}$=13.2, 7.4, 6.1, 5.7 Hz, 1H, 9-CHa), 2.72 ((dddd, $^3J_{H,H}$=13.2, 8.9, 7.4, 6.1 Hz, 1H, 9-CHb), 1.50 (s, 9H, 14-CH3 to 16-CH3).

$^{13}$C NMR (101 MHz, chloroform-d)

δ [ppm]=186.2 (C-7), 154.0 (C-12), 149.8 (C-4), 131.1 (C-1), 129.9 (C-2/C-6), 124.5 (C-3/C-5), 81.8 (C-13), 68.3 (C-10), 59.8 (C-8), 36.8 (C-11), 28.4 (C-14 bis C-16), 27.0 (C-9).

MS (ESI$^+$): m/z=

378.0985; calculated for [C$_{16}$H$_{21}$NO$_6$S]Na$^+$ ([M+Na]$^+$): 378.0982.

733.2051; calculated for [C$_{16}$H$_{21}$NO$_6$S]$_2$Na$^+$ ([2M+Na]$^+$): 733.2071.

(2,2-dioxido-1,2-oxathiolan-3-yl)(4-(methylamino) phenyl)methanone

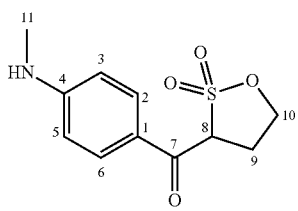 [SMILES: CNc1ccc(C(=O)C2CCOS2(=O)=O)cc1]

tert-butyl [4-(2,2-dioxido-1,2-oxathiolane-3-carbonyl) phenyl](methyl)carbamate (305 mg, 0.86 mmol, 1.0 eq.) was cooled to 0° C. and HCl (2 mL, 4 M in dioxane, 8.0 mmol, 9.3 eq.) was added dropwise. After 30 minutes, a saturated solution of NaHCO$_3$ (2 mL) was added. Water (10 mL) was added and the reaction mixture was extracted with ethyl acetate (3×50 mL). The combined organic fractions were dried over MgSO$_4$, and the solvent was removed under reduced pressure. The product was obtained as a brownish solid without further purification. Yield: 180 mg (0.71 mmol, 82%).

MS (ESI$^+$): m/z=

256.0636; calculated for [C$_{11}$H$_{13}$NO$_4$S]Na$^+$ ([M+Na]$^+$): 256.0638.

278.0458; calculated for [C$_{11}$H$_{13}$NO$_4$S]Na$^+$ ([M+Na]$^+$): 278.0457.

N-[4-(2,2-dioxido-1,2-oxathiolane-3-carbonyl)phenyl]-5-ethyl-4-hydroxy-N,1-dimethyl-2-oxo-1,2-dihydroquinoline-3-carboxamide

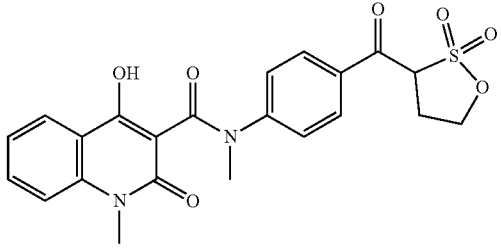 [SMILES: CN(C(=O)c1c(O)c2ccccc2n(C)c1=O)c1ccc(C(=O)C2CCOS2(=O)=O)cc1]

5-ethyl-4-hydroxy-1-methyl-2-oxo-1,2-dihydroquinoline-3-carboxylic acid (190 mg, 0.77 mmol 1.1 eq.) and NEt$_3$ (368 μL, 2.65 mmol, 3.8 eq.) were dissolved in dry THF (5 mL) under an argon atmosphere and cooled to 0° C. Over a period of five minutes SOCl$_2$ (66 μL, 0.91 mmol, 1.3 eq.) in dry THF (454 μL) was added dropwise and stirred for 30 minutes. Afterwards, (2,2-dioxido-1,2-oxathiolan-3-yl)(4-(methylamino)phenyl)methanone (178 mg, 0.70 mmol, 1.0 eq.) in dry THF (5 mL) was added and the reaction mixture was allowed to warm to room temperature. After 90 minutes, a saturated solution of NaHCO$_3$ (1 mL) and water (20 mL) were added and the reaction mixture was extracted with ethyl acetate (3×50 mL). The combined organic fractions were dried over MgSO$_4$, and the solvent was removed under reduced pressure.

Binding of S100A9 protein TLR-4/MD2

Cy5.5-CES271 was successfully synthesized as described in the previous example. Studies were then conducted to verify that Cy5.5-CES271 maintained strong binding affinity for S100A9. In this regard, a specific ELISA (Enyme-linked Immunosorbent Assay) was developed to analyse S100A9 binding to TLR4. In this newly developed assay, the binding of S100A9 to TLR4 can be measured.

Briefly, TLR4/MD2 (3146-TM-050/CF, R&D Systems) was coupled to the wells of a 96-well plate and served as capturing molecule. After blocking of the unspecific binding sites by PBS/5% skim milk powder, plates were washed three times. S100A9 protein was added at a concentration of 2 μg/ml in the presence or absence of 100 μM CES271-Cy5.5 and incubated for two hours at room temperature. Unbound S100 protein was removed by washing the plates for three times, followed by the addition of a primary anti-S100A9-antibody (1 μg/ml, polyclonal, rabbit). After a washing step, the secondary anti-rabbit-IgG-antibody coupled to HRP (1 μg/ml, Cell Signalling) was added. TMB was used as substrate for HRP to quantify binding efficiency by absorbance readings at 450 nm in an ELISA reader (Anthos Mikrosysteme).

Figure 1:
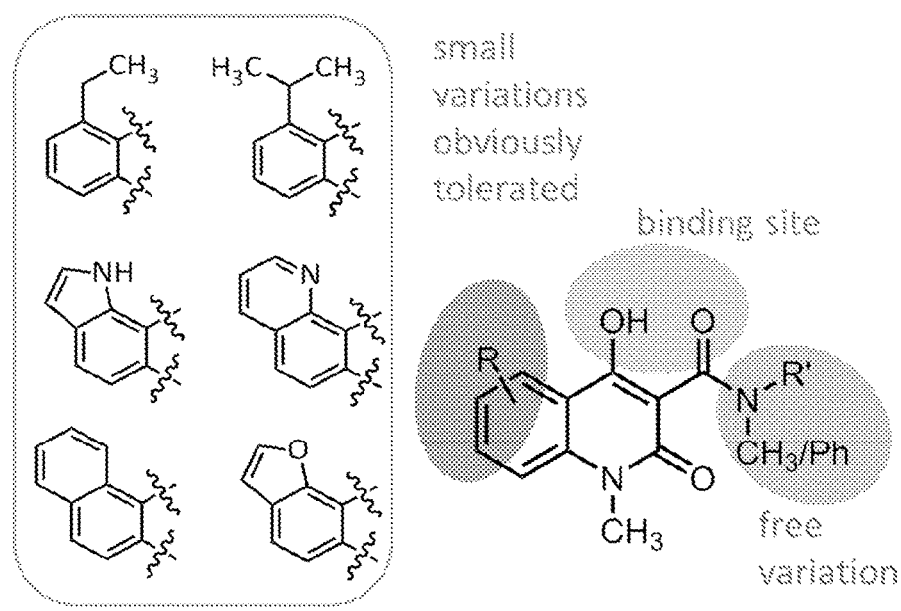
FIG. 1: Overview of quinoline-3-carboxamide compound variations.
Figure 2:
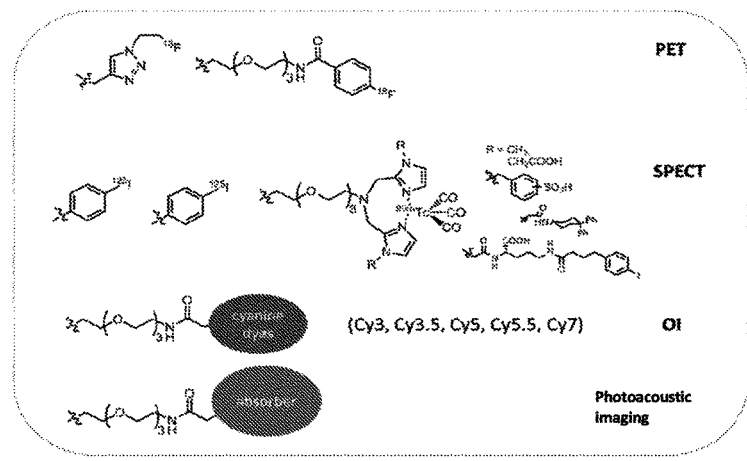
FIG. 2: Examples of labels for use in molecular imaging applications.
Figure 2:
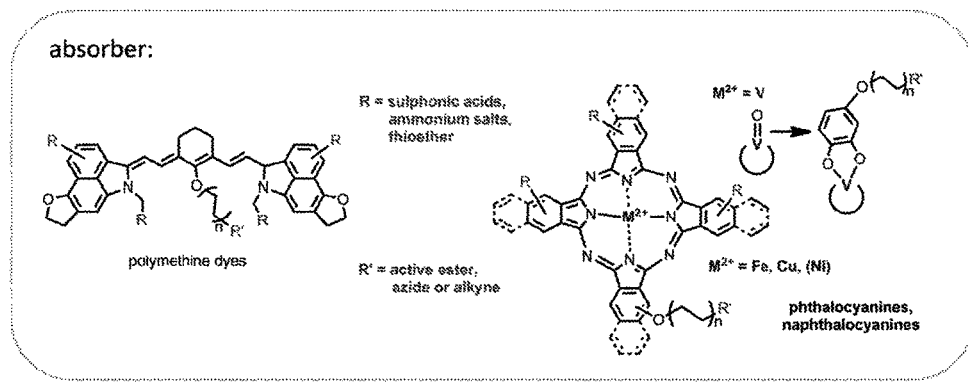
Figure 3:
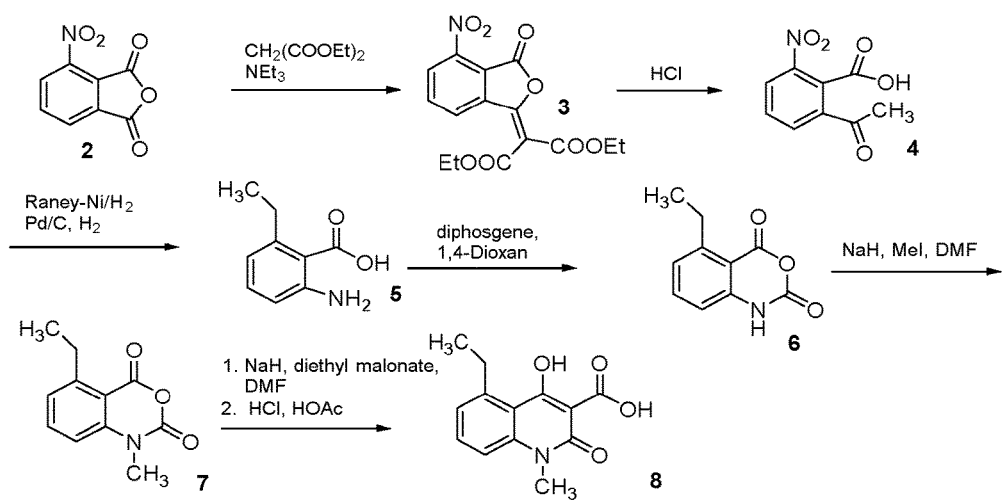
FIG. 3: Overview of the synthesis of 3-quinoline carboxylic acid 8 as an intermediate for the preparation of quinoline-3-carboxamide compounds covalently linked to a label.
Figure 4:
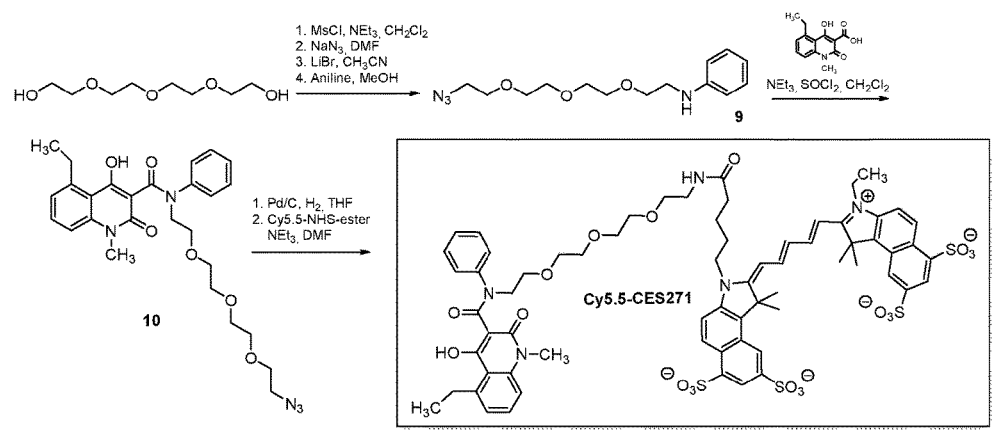
FIG. 4: Overview of the synthesis of the cyanine 5.5-conjugated quinoline-3-carboxamide (Cy5.5-CES271) as a S100A9 ligand for fluorescence-based optical imaging.
Figure 5:
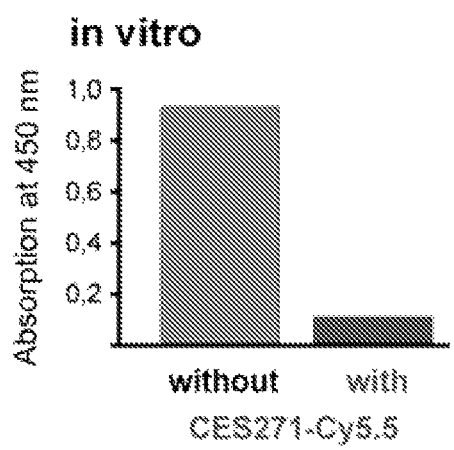
FIG. 5: ELISA-based blocking study showing binding of S100A9 protein to TLR4/MD2 in the presence or absence of quinoline-3-carboxamide compounds covalently linked to a label, in this case Cy5.5-CES271.

The addition of novel non-peptidic S100A9 ligand (i.e. Cy5.5-CES271) was shown to markedly block binding of S100A9 to TLR4, as indicated by a decrease of signal given by the TLR4-S100A9 ELISA. The results, which are shown in FIG. 5, confirm that Cy5.5-CES271 binds to S100A9. This blocking study proves target specificity of Cy5.5-CES271, and shows that binding of S100A9 to TLR4/MD2 (which produces high absorption) can be efficiently blocked in the presence of Cy5.5-CES271 (resulting in low absorption).

Binding of Cy5.5-CES271 to Human and Murine S100A9

The binding constant of Cy5.5-CES271 to murine and human S100A9 was determined by fluorimetric measurements. 0.3788 µM S100A9 (5 µg ml$^{-1}$ of homodimer S100A9) solved in 50 µl PBS was coated to the bottom of a 96-well plate and served as capturing molecule. For each S100A9 coated well a control well was used with 50 µl PBS alone. After a washing step, unspecific binding sites were blocked by PBS/5% skim milk powder. Cy5.5-CES271 was added at increasing concentrations. After 1 h incubation at 4° C., the supernatants were removed and the fluorescence intensity was measured with a fluorimeter. Non-linear regression analysis was performed with a one site saturation model, to calculate the binding constant of Cy5.5-CES271 to either murine or human S100A9. The $K_d$-values of 2.66 µM (murine) and 2.06 µM (human) confirm that Cy5.5-CES271 is eligible for imaging purposes (FIG. 15). A strong binding affinity of the tracer to S100A9 could be observed that is not affected by the attachment of Cy5.5 to CES271.

Mice

Balb/c mice (Harlan Laboratories) and S100A9-deficient mice (S100A9$^{-/-}$), backcrossed from C57BL/6 to Balb/c background (F10 generation) were used at the age of 10- to 14 weeks, sex and age matched for each set of experiments and housed under specific pathogen-free conditions.

Biodistribution of Cy5.5-CES271

The biodistribution of Cy5.5-CES271 and [$^{99m}$Tc]FEB054 injected to healthy Balb/c mice was analysed by the measurement of fluorescence intensity in various organs. FIG. 16 shows the tracer accumulation 1 and 3 h after injection. The tracer was injected at a dose of 2 nmol per mouse. We could observe a good tissue availability of Cy5.5-CES271 and an elimination that was mainly driven by renal excretion, as indicated by the high renal uptake and the increasing concentrations of the tracer in the urinary bladder urine in comparison to the relatively low hepatic uptake. This kinetics, that is different to previously published antibody based tracer anti-S100A9-Cy5.5[7] kinetics favors Cy5.5-CES271 for imaging of organs neighboring the liver like the lung or the heart.

Human Serum Blood Stability of [$^{99m}$Tc]FEB054

Blood serum stability was tested in freshly prepared human blood serum at 37° C. (FIG. 17). Samples were taken after 10, 20, 30, 60, 90 and 120 minutes and analysed using a gradient HPLC system. 5 MBq of [$^{99m}$Tc]FEB054 in 20 µl PBS buffer was added to 200 µl of a freshly prepared human blood serum sample and incubated at 37° C. After 10, 20, 30, 60, 90 and 120 minutes, 20 µl were separated and diluted with 50 µl dichloromethane and 50 µl methanol. After centrifugation, 10 µl of the solution were analysed via gradient-HPLC using a Knauer system with two Smartline1000 pumps, Smartline UV-detector 2500 (Herbert Knauer GmbH), a GabiStar γ-detector (Raytest Isotopenmessgeräte GmbH) and a reverse phase $C_{15}$ column 4.6 mm×250 mm). Eluent A: water (0.1% TFA). Eluent B: methanol (0.1% TFA). Gradient from 70% A to 0% A over 15 minutes, holding four minutes and bad to 70% A over 5 minutes at a flow rate of 5.5 ml min$^{-1}$, detection at λ=254 nm.

Biodistribution of [$^{99m}$Tc]FEB054

Mice were injected and scanned under isoflurane/oxygen inhalation anaesthesia (1.4-1.8% isoflurane, 0.5 l O$_2$/min). All animals were injected with a target dose of 2.5 MBq/g body weight) and a total injection volume ≤150 µl. For the image acquisition we used a NanoSPECT/CT-Plus preclinical camera (Mediso Medical Imaging Systems; Hungary), a 4-head gamma camera equipped with multi-pinhole collimators and a cone beam CT imaging system. In the shown studies we employed 9 pinholes/head with a diameter of 1.0 mm and a field of view of 30 mm×16 mm. 10 projections/scan and 60 seconds/projection resulting in a minimum of 100 kcounts/projection (in order to achieve high quality images with high statistics) were acquired. At the end of the SPECT measurement a CT scan was performed (same FOV as the SPECT scan) (55 kVp; 180 projections/rotation; 500 ms exposure time and 1 mm pitch with constant statistics). Data analysis was performed by CT based definitions of regions-of-interest and quantitative mesurements are expressed as kBq/mL.

In vivo Near-Infrared Optical Imaging (FRI)

In vivo fluorescence reflectance imaging was performed with an IVIS Spectrum small-animal imaging system (Xenogen). Images were acquired and analyzed using Living Image 4.X software (Xenogen). For the measurements the Cy5.5® filter set was used. Identical excitation/emission settings were used for all experiments. Fluorescence emission was measured by Fluorescence emission radiance per incident excitation irradiance (p/sec/cm2/sr/µW/cm2).

Irritant Contact Dermatitis (ICD)

Figure 6:
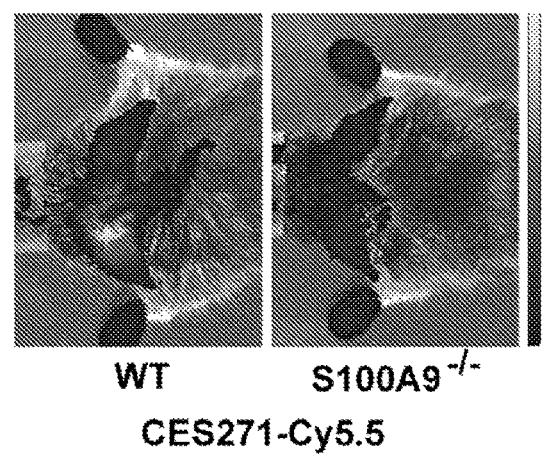
FIG. 6: Accumulation of Cy5.5-CES271 in a mouse model of contact dermatitis (ICD). (A) FRI images showing accumulation of a quinoline-3-carboxamide compound covalently linked to a label (Cy5.5-CES271) in a mouse model of contact dermatitis of the left ear in WT (left) and S100A9 deficient (right) mice. (B) FRI images and S100A9 staining showing accumulation of a quinoline-3-carboxamide compound covalently linked to a label (Cy5.5-CES271) in a mouse model of contact dermatitis.
Figure 6:
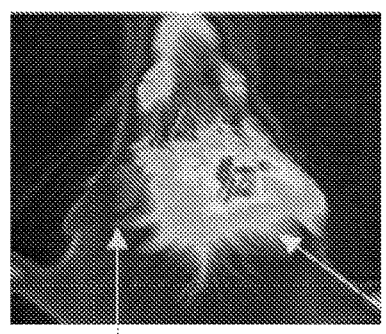
Figure 6:
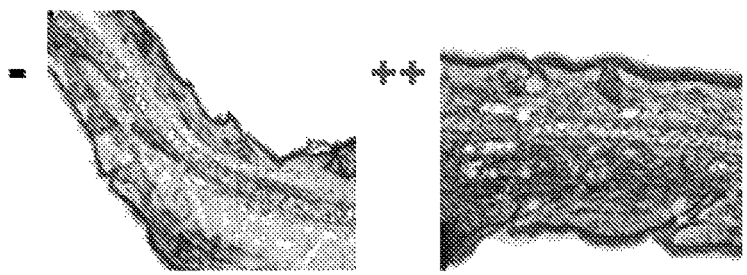

ICD was induced by the application of 20 µl 1% croton oil in olive oil-acetone (1:4) to the ventral surface of the left ear of mice for 24 h (n=5 per group), whereas the right ear served as a control. FRI was performed 3 h after tracer application, corresponding to 27 h after croton oil treatment. The dermatitis mouse model showed significant accumulation of a quinoline-3-carboxamide compound covalently linked to a label at sites of inflammation. As shown in the results of imaging experiments depicted in FIG. 6, Cy5.5-CES271 showed significant accumulation in the inflamed ear of a dermatitis mouse model, which was not observed in S100A9$^{-/-}$ deficient mouse model. FIG. 6 shows preliminary FRI images of Cy5.5-CES271 in a mouse model of contact dermatitis of the left ear (WT vs. S100A9 deficient mice). Moreover, FRI images of Cy5.5-CES271 and Cy7-CES271 comparing the Total Radiant Efficiency in inflamed and control ears reveals highly significant correlation between the Cy7-CES271 and Cy5.5-aS100A9 signal in a mouse model of contact dermatitis (ICD), (FIG. 21). The comparison of Cy7-CES271 to the well characterized aS100A9-Cy5.5 was performed by parallel injection of the tracers. As we could not compare two tracers linked with the identical dye Cy5.5, CES271 was labeled with Cy7. This dye has distinct excitation and emission wavelengths and allows for a direct comparison of Cy7-CES271 to aS100A9-Cy5.5 by parallel injection of the tracers. FIG. 21 shows two images of the identical mouse recorded in the Cy5.5 (antibody) and Cy7 channel. In the direct comparison of Cy7-CES271 and aS100A9-Cy5.5 we observed an excellent correlation between the signal recorded from each tracer (FIG. 21B; $R^2$=0.96; n=8; p<0.001). This shows, that the binding of CES271 to S100A9 has the same dependency on local S100A9 expression as the S100A9 specific antibody based tracer aS100A9-Cy5.5. In the Cy7 channel the quantum yield is much lower compared to the Cy5.5 channel, which means that the recorded signal with Cy5.5-CES271 is higher than compared to Cy5.5-CES271 (right image; FIG. 21). The difference was qualified by a direct comparison CES271-Cy5.5 with its Cy7 derivate. Any significant differences between the relative accumulation of these tracers in the target tissue (n=6; p=0.33; data not shown) could not be observed while the absolute radiant efficiency obtained with Cy7-CES271 was lower than the one obtained with -Cy5.5-CES271 by a ratio of 0.199±0.013 (n=6; p<0.001; data not shown). In addition, it could be observed that the tracers have different kinetics which means that at the ideal imaging time points and their specific signal differ, which means that they have different ideal time point for imaging (data not shown). CES271-Cy5.5 was synthesized according to our published procedure (Faust et al. 2015). Cy5.5-NHS ester and Cy7-NHS ester was purchased from GE Healthcare at the highest purity grade available. Antibodies and antibody labeling (from Nat Com). Rabbit-derived antibodies addressing S100A9 were purified via protein G-sepharose and labelled with the fluorochrome Cy5.5 according to the manufacturer's instructions (GE Healthcare), as described previously. Briefly, 5 mg of the antibody was dialysed towards 100 mM $Na_2CO_3$ buffer, pH 8.0 and a 20-fold excess of the fluorochrome was added for 90 min at RT. The resulting tracer was purified from unbound dye using size exclusion chromatography (PD10 column). The labelling efficacy (dye/antibody ratio) was determined on the basis of ultraviolet-spectra of the purified dye-antibody compound using PBS as a reference buffer. Typically, the labelling resulted in 2.5-3.0 fluorochrome molecules per antibody, irrespective of the precursors.

Additionally, hybrid nuclear imaging (SPECT) and computed tomography (CT) was performed in the mouse model of contact dermatitis of the left ear. FIG. 19 shows a significant uptake of the 99mTc-labeled quinoline-3-carboxamide compound in the inflamed ear in contrast to the healthy control ear. Quantitative image analysis of the dynamic imaging 0-60 minutes post injection shows increasing uptake ratios of tracer in the inflamed ear versus blood and muscle, respectively. This improve in image contrast is of utmost importance for imaging based diagnostics.

These results demonstrate that tracer-tagged quinoline-3-carboxamide compounds provided herein show significant accumulation at sites of inflammation and/or inflammatory active diseases.

Collagen Induced Arthritis

Induction and imaging of CIA: Arthritis was induced in DBA/1j mice by injection of bovine collagen type II. Bovine collagen type II (bCII, MD Biosciences) was dissolved in 0.05 M acetic acid at a concentration of 2 mg/ml. DBA/1j mice were injected subcutaneously at the tail base with 100 µg bCII emulsified in CFA (Difco) and boostered on day 21 with 100 µg bCII in IFA at the same location. Mice were regularly inspected from day 14 after disease induction and scored for swelling, erythema and deformation of each joint three times a week. Imaging was performed after arthritis was clinically detectable in the majority of treated animals at indicated time points after tracer application of either Cy5.5-CES271 or [99mTc]FEB054.

SPECT/CT imaging of inflamed joints was recorded 1 h after iv injection of [99mTc]FEB054 (55 MBq of [99mTc] FEB054 per mouse). Individual feet of the mice were analysed separately according to the histological score. S100A9-expression as depicted by SPECT was in excellent correlation with clinical scoring, clearly discriminating clinically mild from severe joint inflammation with high SNR (FIG. 20). Even single affected joints could be clearly identified.

Myocardial Infarction

Figure 7:
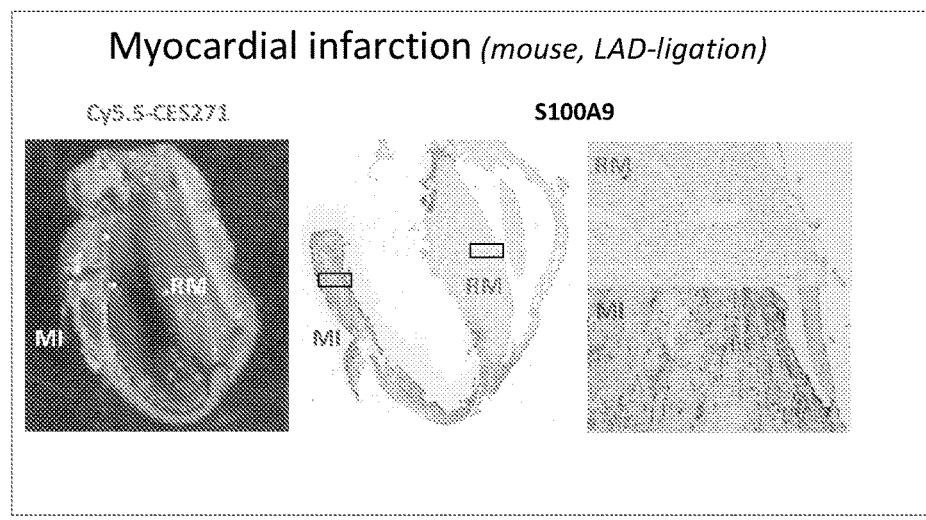
FIG. 7: Accumulation of Cy5.5-CES271 in a mouse model of myocardial infarction. One day post occlusion of the LAD in a C57Bl/6 mouse: FRI of the explanted heart (longitudinal mid-infarction cut) two hours after i.v. injection of 2 nmol Cy5.5-CES271. The tracer accumulates in the myocardial infarction (MI) in concordance to the presence of S100A9 shown by histological staining. Furthermore, absence of S100A9 in the remote myocardium (RM) is accompanied by the lack of Cy5.5-CES271.

Myocardial infarction was induced by opening the chest of a mouse and transient ligation of the left coronary artery for 60 minutes. The ischemic event triggers acute inflammatory response to the tissue injury in the first hours/days followed by a remodeling process (involving less intense inflammatory processes) after about one week. FRI was performed one day after the surgical intervention to assess the intense acute inflammatory response and the images in FIG. 7 were acquired two hours after injection of 2 nmol Cy5.5-CES-271. FRI experiments in mouse models of myocardial infarction and atherosclerosis show significant accumulation of quinoline-3-carboxamide compound covalently linked to a label at sites of inflammation. FIG. 7 shows the accumulation of Cy5.5-CES271 at one day post occlusion of the LAD in a C57BI/6 mouse. FRI of the explanted heart (longitudinal mid-infarction cut) two hours after i.v. injection of 2 nmol Cy5.5-CES271 is shown. These results demonstrate that the tracer accumulates in the myocardial infarction (MI) in accordance with the presence of S100A9 as shown by histological staining. The absence of S100A9 in the remote myocardium (RM) is accompanied by a lack of Cy5.5-CES271 accumulation.

Atherosclerosis, Histology and Immunohistochemistry

Atherosclerosis is an inflammatory disease of the vessel wall. $SR-BI^{-/-}/apoE^{R61\ h/h}$-mice (HypoE) are known to develop atherosclerotic lesions especially when set on a high fat and high choleresterol diet (HFC). Typical predeliction site is the aortic arch. 12-14 week old mice were set on HFC diet for 10 days. At day 10 of HFC diet Cy5.5-CES271 was injected i.v., the mice were sacrificed two hours p.i., the aortic arches were explanted, and measured ex-vivo by FRI.

The hearts and aorta were fixed overnight in 4% paraformaldehyde and embedded in paraffin. Sections measuring 4 µm in thickness were analyzed. For immunohistochemistry, paraffin skin sections (4 µm) were dewaxed, blocked with 10% fetal bovine serum, and incubated with rabbit anti-S100A9 or MAC-3 antibodies for 1 h at room temperature followed by a goat-anti-rabbit biotinylated antibody and 3,3' diaminobenzidine (DAB).

Figure 8:
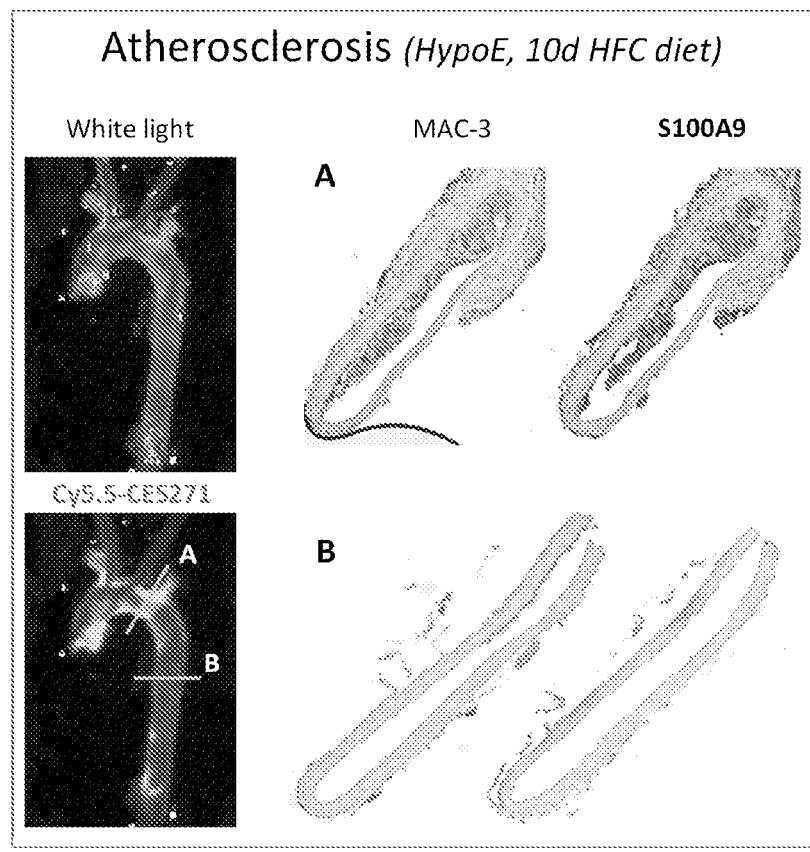
FIG. 8: Accumulation of Cy5.5-CES271 in a mouse model of atherosclerosis in a HypoE mouse, 10 days on HFC diet. FRI of the explanted aorta (2h p.i.) shows accumulation of the Cy5.5-CES271 (yellow) in plaque lesions (white patches, bright light). Systematic histological analysis of the aorta shows high levels of S100A9 in high uptake areas of Cy5.5-CES271 (A) and absence/very low levels of S100A9 in low uptake areas (B) of the tracer.
Figure 9:
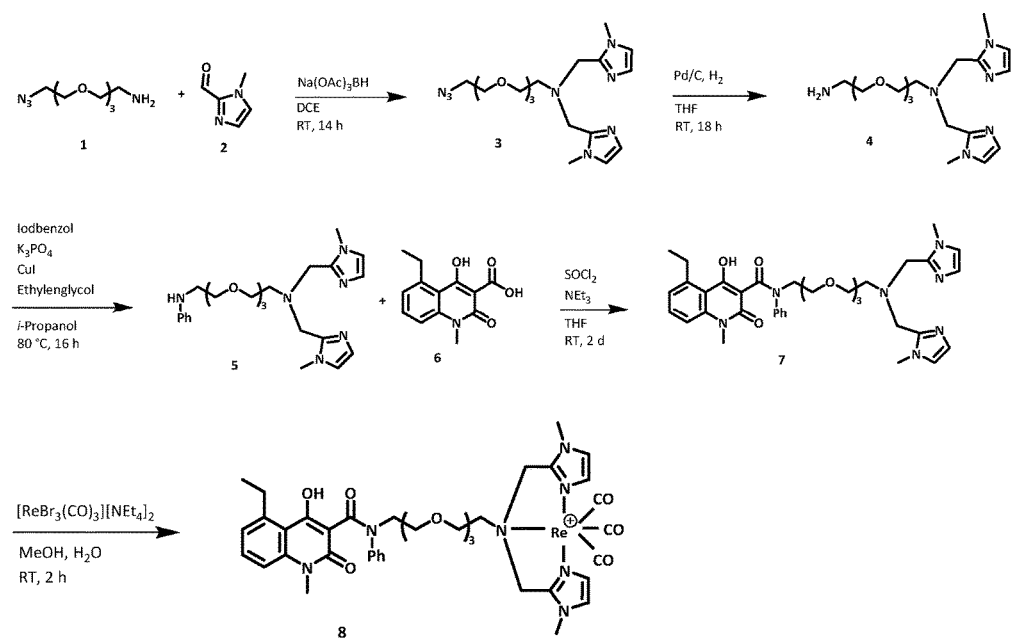
FIG. 9: Overview of the synthesis of 5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide and the corresponding Re-complex fac-[Re(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$.
Figure 10:
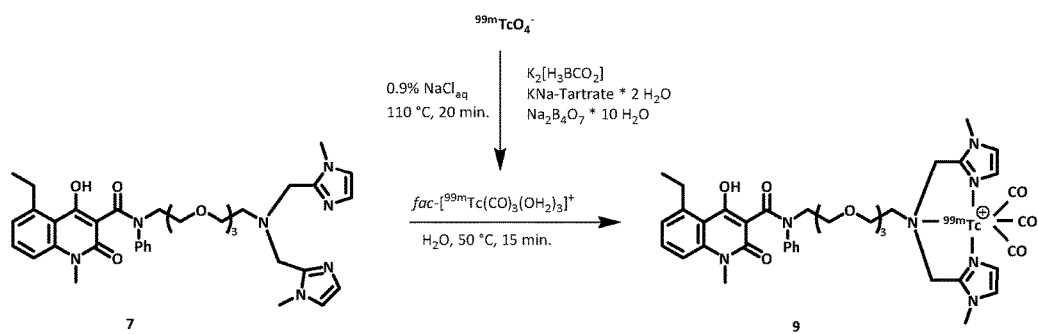
FIG. 10: Overview of the synthesis of fac-[$^{99m}$Tc(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ ($^{99m}$Tc-FEB054) as a S100A9 ligand for single photon emission tomography (SPECT).
Figure 11:
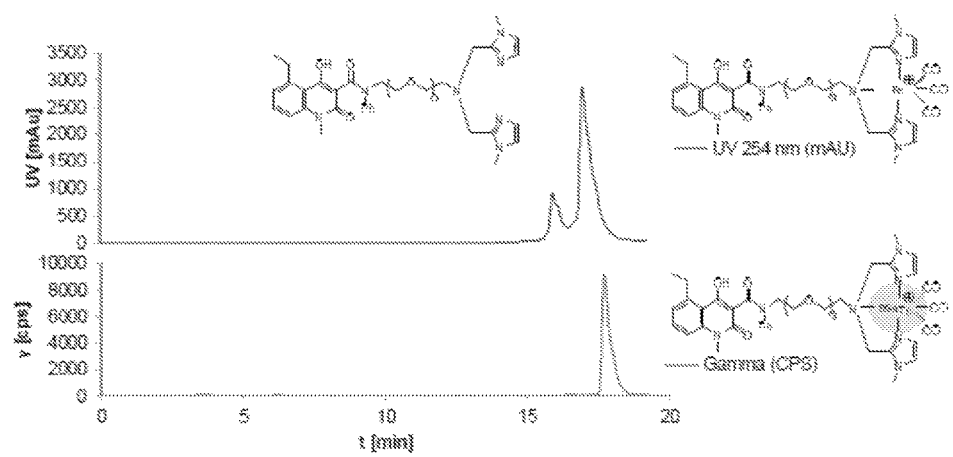
FIG. 11: Characterisation of fac-[$^{99m}$Tc(CO)$_3$(5-ethyl-4-hydroxy-1-methyl-N-{1-(1-methyl-1H-imidazol-2-yl)-2-[(1-methyl-1H-imidazol-2-yl)methyl]-5,8,11-trioxa-2-azatridecan-13-yl}-2-oxo-N-phenyl-1,2-dihydroquinoline-3-carboxamide)]$^+$ ($^{99m}$Tc-FEB054).
Figure 11:
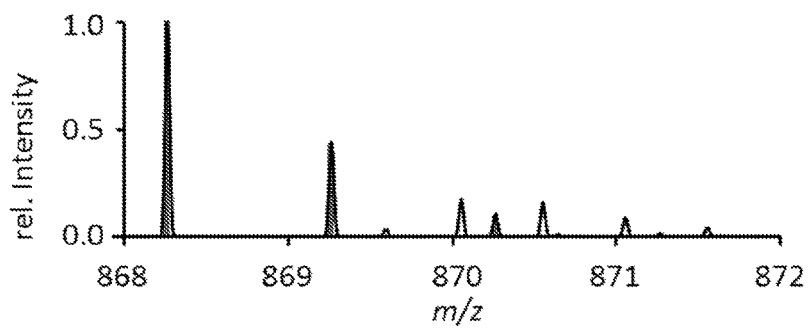

FRI imaging of the explanted aorta (2 h p.i.) shows accumulation of Cy5.5-CES271 (yellow) in plaque lesions (white patches, bright light), FIG. 8. Systematic histological analysis of the aorta shows high levels of S100A9 in high uptake areas of Cy5.5-CES271 (A) and absence/very low levels of S100A9 in low uptake areas (B) of the tracer.

Acute Lung Injury (ALI)

LPS-induced lung inflammation was elicited via intranasal application of 50 pg or 10 pg of LPS. LPS from *Escherichia coli* 055:B5 was obtained from Sigma-Aldrich. Directly after the administration of LPS 2 nmol of tracer were injected intravenously. Glycine saturated Cy5.5 served as a perfusion control for CES271-Cy5.5, while Cy5.5-labelled rabbit IgG without relevant specificity served as a control for aS100A9-Cy5.5. Mice were either assigned to fluorescence mediated tomography (FMT) to fluorescence reflectance imaging (FRI). For FRI imaging, the mice were sacrificed at the indicated time points. Afterwards, BALF was obtained and the lungs were fixed with 1% low melt aggarose.

2D FRI lung imaging was performed using the Bruker FX Pro Imaging Station (Bruker Corporation). Excitation light was set to 630 nm using an appropriate bandpass filter. Emission at 700 nm was recorded using a filtre-equipped high-sensitivity (4-million-pixel) cooled charge-coupled device camera. Acquisition time was 5 s for each image.

Mice were intravenously injected with Cy5.5-labelled CES271 (CES271-Cy5.5). The animals underwent optical imaging at various time points after injection. In our blocking experiments each mouse received 2 pmol CES271 1 h before 2 nmol of CES271-Cy5.5 were injected. Control mice received the same volume PBS. Imaging was performed at identical time points. 2D FRI lung imaging was performed using the Bruker FX Pro Imaging Station (Bruker Corporation). Excitation light was set to 630 nm using an appropriate bandpass filter.

Emission at 700 nm was recorded using a filtre-equipped high-sensitivity (4-million-pixel) cooled charge-coupled device camera. Acquisition time was 5 s for each image.

Immunohistochemistry of ear sections (cryo) was performed as described earlier using purified rabbit anti-sera against murine S100A9 (Petersen et al. 2013). Briefly, after inhibition of endogenous peroxidase activity in frozen tissue sections Fc receptors were blocked by incubating in PBS/1% BSA including 50% normal goat serum (NGS). Slides were immunostained in a two-step procedure of incubation of primary antibody or isotype control followed by a horseradish peroxidase-conjugated secondary antibody using AEC as chromogen. Images were acquired by using an upright microscope (Axioskop, Zeiss). Statistical analysis (from Nat Com). Results are presented throughout as mean values±standard deviation (s.d.). P-values are given in the figure legends and values of p>0.05 were considered not to be significant. Statistical analyses were performed by parametric tests.

Cy5.5-CES271 enables imaging of LPS-induced lung inflammation with high sensitivity. Acute lung inflammation is frequently accompanied by extraordinary high levels of S100A8/A9 in BALF and serum. To evaluate whether visualizing S100A9-expression with CES271-Cy5.5 could facilitate early diagnosis of acute lung injury we tested a model of acute LPS-induced lung injury in mice in a pronounced, high dose and a milder, low dose setting. Systemic and local S100A8/A9 expression levels showed a dose and time dependent increase (FIG. 22A). The concentration of S100A8/S100A9 was especially high in the bronchoalveolar fluid (BALF) early after LPS application. Expression changes were confirmed by immunohistochemical analysis (FIG. 22A). Limited access of OI to the deep tissue target region on the one hand and continuous movement of the target region on the other hand are known challenges for imaging in this model. Therefore ex vivo analysis of the explanted lungs of affected animals was performed. At 3 and 6 hours after parallel LPS-/Cy5.5-CES271-application specific tracer accumulation could clearly be delineated. Unaffected lungs of animals that received LPS free saline as a control (FIG. 22B; n=3; p<0.01) did not show a similar tracer accumulation. As a control for possible early perfusion changes or tissue swelling in LPS treated animals, which could by themselves cause an increase in the recorded signal, we introduced an additional control. Glycine saturated Cy5.5 was injected into either LPS or saline treated mice. The recorded signal was comparable to the Cy5.5-CES271 control signal and significantly lower than Cy5.5-CES271 signal in LPS treated mice (FIG. 22B; n=3; p<0.01). This shows that Cy5.5-CES271 enables the detection of ALI early on in the disease course. S100A8/S100A9 serum levels were then measured by ELISA and correlated with the mean fluorescence intensity over the explanted lungs. We observed a good correlation between the systemic S100A8/S100A9 levels and the local inflammatory activity represented by the tracer uptake (FIG. 22C, $R^2=0.69$; n=19; p<0.001).

A very interesting finding regarding the disease model was that the perfusion control did not show any significant differences in the tracer uptake between LPS treated and saline treated animals, which means that perfusion changes could be a late event in the development of an acute lung injury. This could be an explanation why to date perfusion based contrast agents fail to visualize ALI early on. Accordingly, these results aim to provide a new developmental option for the early diagnosis of ALI in the clinical setting.

The new tracer Cy5.5-CES271 represents the first approach with the potential of easy and quick translation of inflammation imaging in a broad range of clinical settings. It is based on a proven S100A9-binding Q-compound (Faust et al. 2015) that has already passed phase III trials. The linked indocyanine green derivate has separately found its way into clinical use as an optical imaging perfusion marker. Despite the limitations of this perfusion based contrast agent, the introduction of an optical scanner for visualization of the disease activity in rheumatoid arthritis proves that optical imaging is finding its way into clinical practice. In fact, Cy5.5-CES271 could readily be used for optical imaging of epithelial lesions. It enables monitoring of cutaneous inflammation and could find general use in the growing field of clinical fluorescence endoscopy. Monitoring of inflammatory bowel disease patients could be a first application, because this disease shows a burst of local expression of S100A8/S100A9 (calprotectin) early on and calprotectins proven prognostic potential makes it an attractive target in this setting.

The proven biocompatibility of its basic elements makes it presumable that Cy5.5-CES271 also displays good biocompatibility and could pave the way for quick and successful introduction into clinical inflammation imaging. Compared to antibody based tracers Cy5.5-CES271 has much faster kinetics. This is especially important after radiolabelling for potential PET or SPECT usage of the tracer, which allows for inflammation monitoring in the whole body of the patient. For this purpose, a faster clearance of the radioactive tracer from the blood would reduce the effective dose that the patient receives under imaging purposes. In addition, antibodies are mainly cleared via the liver while our tracer is excreted via the Ren and adds an alternative route of elimination for patients that are compromised in either of the eliminating organs.

It will be clear that the invention may be practiced otherwise than as particularly described in the foregoing description and examples. Numerous modifications and variations of the present invention are possible in light of the above teachings and, therefore, are within the scope of the appended claims.

REFERENCES

Angelo J. Amoroso, Michael P. Coogan, Jennifer E. Dunne, Vanesa Fernández-Moreira, Jacob B. Hess, Anthony J. Hayes, David Lloyd, Coralie Millet, Simon J. A. Pope and Craig Williams, Rhenium fac tricarbonyl bisimine complexes: biologically useful fluorochromes for cell imaging applications. Chem. Commun 2007, 3066-3068.

Björk, P., Björk, A., Vogl, T., Stenstrom, M., Liberg, D., Olsson, A., Roth, J., Ivars, F., Leanderson, T. Identification of Human S100A9 as a Novel Target for Treatment of Autoimmune Disease via Binding to Quinoline-3-Carboxamides. PloS Biology 2009, 7(4): e1000097.

Chan J., Roth J., Oppenheim J., Tracey K., Vogl T., Feldmann M., Horwood N., Nanchahal, J. Alarmins: Awaiting a Clinical Response. J. Clin. Invest. 2012; 122: 2711-2719.

Faust A., Völler, T., Busch, F., Schäfers, M., Roth, J., Hermann, S., Vogl, T.: Development and evaluation of a non-peptidic ligand for the molecular imaging of inflammatory processes using S100A9 (MRP14) as a novel target. Chem. Comm. 2015.

Foell, D., Roth, J. Proinflammatory S100 proteins in arthritis and autoimmune disease. Arthritis Reum. 2004, 50: 3762-3771.

Hessian, P. A., Edgeworth, J., Hogg, N. MRP-8 and MRP-14, two abundant Ca(2+)-binding proteins of neutrophils and monocytes. J. Leukoc. Biol. 1993, 53: 197-204.

Jansson, K. EP2316818A1; Mar. 11, 2009

Jönsson, S., Andersson, G., Fex, T., Fristedt, T., Hedlund, G., Jansson, K., Abramo, L., Fritzson, L., Pekarski, A., Runstrom, A., Sandin, H., Thuvesson, I., Bjork, A. J. Med. Chem. 2004, 47: 2075-2088.

Loser K., Vogl T., Voskort M., Lueken A., Kupas V., Nacken W., Klenner L., Kuhn A., Foell D., Sorokin L., Luger T. A., Roth J., Beissert S. The toll-like receptor 4 ligands Mrp8 and Mrp14 are crucial in the development of autoreactive CD8+ T cells. Nat Med. 2010; 16: 713-717.

Lüthy, C., Zondler, H., Rapold, T., Seifert, G., Urwyler, B., Heinis, T., Steinrücken, C., Allen, *J. Pest Manag. Sci.* 2001, 57: 205-227.

Thomas Priem, Cédric Bouteiller, David Camporese, Anthony Romieu and Pierre-Yves Renard, Synthesis and reactivity of a bis-sultone cross-linker for peptide conjugation and [$^{18}$F]-radiolabelling via unusual "double click" approach, Org. Biomol. Chem., 10, 1068-1078.

Petersen, B. Et al. The alarmin Mrp8/14 as regulator of the adaptive immune response suring allergic contact dermatitis. *Embo. J.* 2013, 32: 100-111.

Preiningerova, J. Oral laquinimod therapy in relapsing multiple sclerosis. *Exp. Opin. Investig. Drugs,* 2009; 18(5): 985-989.

Vogl T., Tenbrock K., Ludwig S., Leukert N., Ehrhardt C., van Zoelen M. A., Nacken W., Foell D., van der Poll T., Sorg C., Roth J. Mrp8 and Mrp14 are endogenous activators of toll-like receptor 4, promoting lethal, endotoxin-induced shock. *Nat Med.* 2007, 13: 1042-1049.

Vogl T., Eisenblätter, M., Völer, T., Zenker, S., Hermann, S., van Lent, P., Faust, A., Geyer, C., Petersen, B., Roebrock, K., Schäfers, M., Bremer, C., Roth, J. Alarmin S100A8/S100A9 as a biomarker for molecular imaging of local inflammatory activity. *Nature Comm.* 5: 4593.2014.

The invention claimed is:

1. A compound having formula (I)

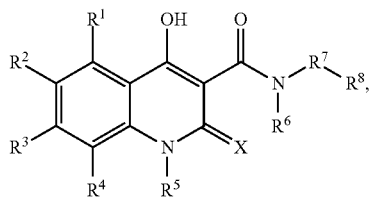

(I)

wherein $R^1$ is linear or branched C1-C6 alkyl;
$R^2$, $R^3$, and $R^4$ are H;
$R^5$ is C1-C6 alkyl;
$R^6$ is aryl;
$R^7$ is an optional linker;
X is O or S; and
$R^8$ is a label;
or a salt, or tautomer thereof; wherein the compound is not:

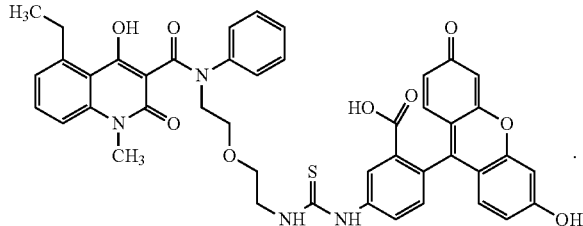 [SMILES: CCc1cccc2c1c(O)c(C(=O)N(CCOCCNC(=S)Nc1ccc(-c3c4ccc(=O)cc-4oc4cc(O)ccc34)c(C(=O)O)c1)c1ccccc1)c(=O)n2C]

2. The compound according to claim 1, wherein $R^1$ is selected from the group consisting of —CH$_3$, —CH$_2$CH$_3$, —CH$_2$CH$_2$CH$_3$, and —CH(CH$_3$)$_2$.

3. The compound according to claim 1, wherein X is O.

4. The compound according to claim 1, wherein $R^7$ is a linker comprising

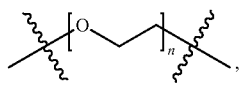

wherein n is an integer from 0 to 20.

5. The compound according to claim 1, wherein the label is any one of a single photon emission tomography (SPECT) label, a positron emission tomography (PET) label, an optical imaging label, a magnetic resonance imaging (MRI) label, an ultrasound label or a photoacoustic imaging label.

6. The compound according to claim 1, wherein the compound is selected from the group consisting of
a compound having formula (IV)

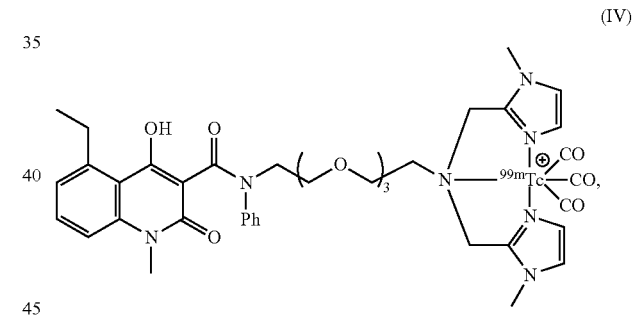

(IV)

a compound having formula (V)

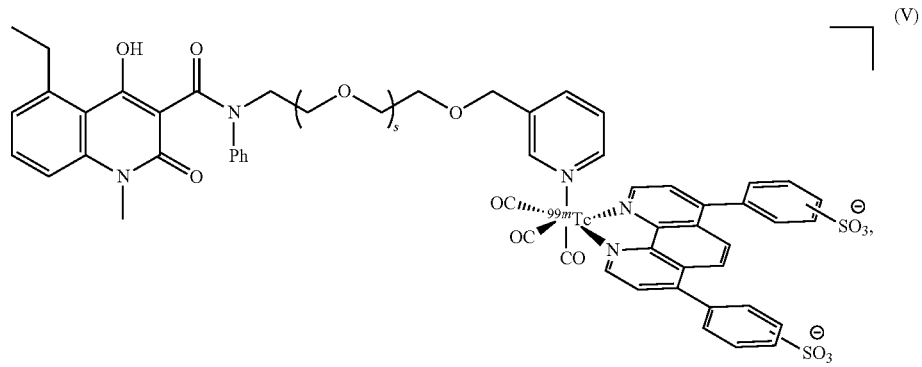

(V)

a compound having formula (II)
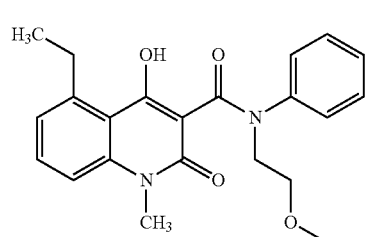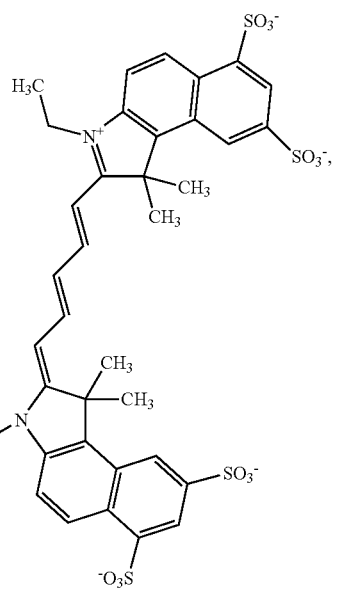
(II)
and
a compound having formula VIII
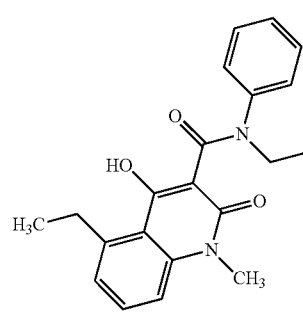
(VIII)
or a salt, hydrate, or tautomer thereof.

7. A process for the preparation of a compound of the formula (I) or its salts, tautomers or solvates thereof, as claimed in claim 1, comprising reacting a compound of the formula (VI) with a compound of the formula (VII) to give a compound of the formula I,

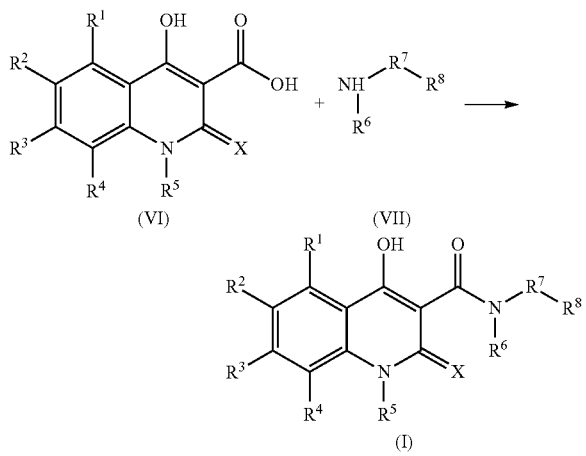

wherein $R^1$, $R^2$, $R^3$, $R^4$, $R^5$, $R^6$, $R^7$, $R^8$ and X are defined as in claim 1.

8. A compound having formula (I)

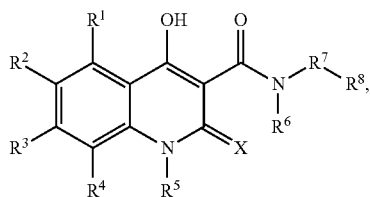

wherein $R^1$ is linear or branched C1-C6 alkyl;

$R^2$, $R^3$, and $R^4$ are H;

$R^5$ is C1-C6 alkyl;

$R^6$ is alkyl;

$R^7$ is an optional linker;

X is O or S; and $R^8$ is a label, wherein the label is any one of a single photon emission tomography (SPECT) label, a positron emission tomography (PET) label, an optical imaging label, a magnetic resonance imaging (MRI) label selected from the group consisting of a perfluorinated $^{19}F$ label and Gd(DOTA), an ultrasound label or a photoacoustic imaging label;

or a salt or tautomer thereof.

9. The compound according to claim 8, wherein the compound has formula (IIIb):

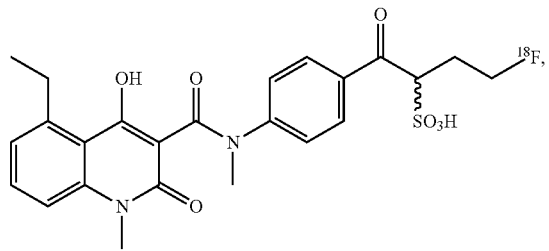

or a salt or tautomer thereof.

* * * * *